US007329649B2

(12) United States Patent
Fisher et al.

(10) Patent No.: US 7,329,649 B2
(45) Date of Patent: Feb. 12, 2008

(54) COMBINATORIAL METHODS FOR INDUCING CANCER CELL DEATH

(75) Inventors: Paul B. Fisher, Scarsdale, NY (US); Zao-Zhong Su, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 261 days.

(21) Appl. No.: 10/783,571

(22) Filed: Feb. 20, 2004

(65) Prior Publication Data

US 2004/0191223 A1     Sep. 30, 2004

Related U.S. Application Data

(63) Continuation of application No. PCT/US02/26454, filed on Aug. 19, 2002, which is a continuation-in-part of application No. 09/933,115, filed on Aug. 20, 2001.

(51) Int. Cl.
*A61K 48/00* (2006.01)
(52) U.S. Cl. .................. 514/44; 536/23.5; 536/24.5
(58) Field of Classification Search ............. 536/23.5, 536/24.5; 514/44
See application file for complete search history.

(56) References Cited

U.S. PATENT DOCUMENTS

| | | | |
|---|---|---|---|
| 5,093,246 A | 3/1992 | Cech et al. | |
| 5,539,082 A | 7/1996 | Nielsen et al. | |
| 5,543,327 A | 8/1996 | Yen-Maguire et al. | |
| 5,710,137 A * | 1/1998 | Fisher ..................... | 514/44 |
| 5,714,331 A | 2/1998 | Buchardt, deceased et al. | |
| 5,719,262 A | 2/1998 | Buchardt, deceased et al. | |
| 6,025,192 A | 2/2000 | Beach et al. | |
| 6,229,006 B1 | 5/2001 | Wu | |
| 6,235,310 B1 | 5/2001 | Wang et al. | |
| 6,242,589 B1 | 6/2001 | Cook et al. | |
| 6,245,520 B1 | 6/2001 | Wang et al. | |
| 6,245,747 B1 | 6/2001 | Porter et al. | |
| 6,255,071 B1 | 7/2001 | Beach et al. | |
| 6,255,111 B1 | 7/2001 | Bennett et al. | |

FOREIGN PATENT DOCUMENTS

| | | |
|---|---|---|
| WO | WO9716547 A1 * | 5/1997 |
| WO | WO99/47709 | 9/1999 |
| WO | WO99/49898 | 10/1999 |
| WO | WO 01/05437 | 1/2001 |
| WO | WO 02/45737 | 6/2002 |
| WO | WO 2004/060269 | 7/2004 |

OTHER PUBLICATIONS

Saison-Behmoaras et al. (EMBO J., 1991; 10(5):1111-1118).*
Sarkar et al., 2002. mda-7 (IL-24) mediates selective apoptosis in human melanoma cells by inducing the coordinated overexpression of the GADD family of genes by means of p38 MAPK Proc. Natl Acad Sci USA 99(15):10054-10059.
Cancer Facts and Figures, 2001. Atlanta GA. American Cancer Society.
Clarke GA, Ryan E, Crowe JP, O'Keane JC, MacMathuna P (2001). Tumour-derived mutated K-ras codon 12 expression in regional lymph nodes of stage II colorectal cancer patients is not associated with increased risk of cancer-related death. Int. J. Colorectal Dis. 16(2):108-111.
Demunter A, Ahmadian MR, Libbrecht L, Stas M, Baens M, Scheffzek K, Degreed H, De Wolf-Peeters C, van Den Oord JJ (2001). A novel N-ras mutation in malignant melanoma is associated with excellent prognosis. Cancer Res. 61(12):4916-4922.
Ding XZ, Adrian TE (2001). MEK-ERK-mediated proliferation is negatively regulated by P38 map kinase in the human pancreatic cancer cell line, PANC-1. Biochem. Biophys. Res. Commun. 282(2):447-453.
Ellenrieder V, Hendler SF, Boeck W, Seufferlein T, Menke A, Ruhland C, Adler G, Gress TM (2001). Transforming growth factor beta1 treatment leads to an epithelial-mesenchymal transdifferentiation of pancreatic cancer cells is mediated by matrix metalloproteinase-2 and the urokinase plasminogen activator system. Int. J. Cancer 93(2):204-211.
Ellenrieder V, Hendler, SF, Ruhland C, Boeck W, Adler G, Gress TM (2001). TGF-beta-induced invasiveness of pancreatic cancer cells is mediated by matrix metalloproteinase-2 and the urokinase plasminogen activator system. Int. J. Cancer 93(2):204-211.
El-Hariry I, Pignatelli M, Lemoine NR (2001). FGF-1 and FGF-2 modulate the E-cadherin/catenin system in pancreatic adenocarcinoma cell lines. Br. J. Cancer 84(12):1656-1663.
Evans DB, Wolff RA, Crane CH (2001). Neoadjuvant strategies for pancreatic cancer. Oncology (Huntingt) 15(6):727-737.
Gazdar et al., (2001) "targeted therapies for killing tumor cells", PNAS 98: 10028-10030.
Glazyrin AL, Adsay VN, Vaitkevicius VK, Sarkar FH (2001). CD95-related apoptotic machinery is functional in pancreatic cancer cells. Pancreas 22(4):357-365.
Gunzburg WH, Salmons B. (2001). Novel clinical strategies for the treatment of pancreatic carcinoma. Trends Mol. Med. 7(1):30-37.
Hashimoto K, Nio Y, Sumi S, Toga T, Omori H, Itakura M, Yano S (2001). Correlation between TGF-beta1 and p21 (WAF1/CIP1) expression and prognosis in resectable invasive ductal carcinoma of the pancreas. Pancreas 22(4):341-347.

(Continued)

*Primary Examiner*—Jon E. Angell
(74) *Attorney, Agent, or Firm*—Baker Botts L.L.P.

(57) ABSTRACT

The present invention relates to methods and compositions for inhibiting proliferation and inducing cell death in a population of cancer cells by (i) increasing the amount of the differentiation associated protein MDA-7, and (ii) decreasing RAS activity within the population. It is based, at least in part, on the discovery that decreasing expression of a mutated, activated K-ras gene, together with introducing an expressible mda-7 gene, in pancreatic cells had a synergistic growth-inhibitory and anti-survival effect, and abolished tumorigenicity of the cells in athymic nude mice. The methods of the invention may be directed to the therapy of pancreatic cancer and other malignancies.

1 Claim, 31 Drawing Sheets

OTHER PUBLICATIONS

Figure 1:
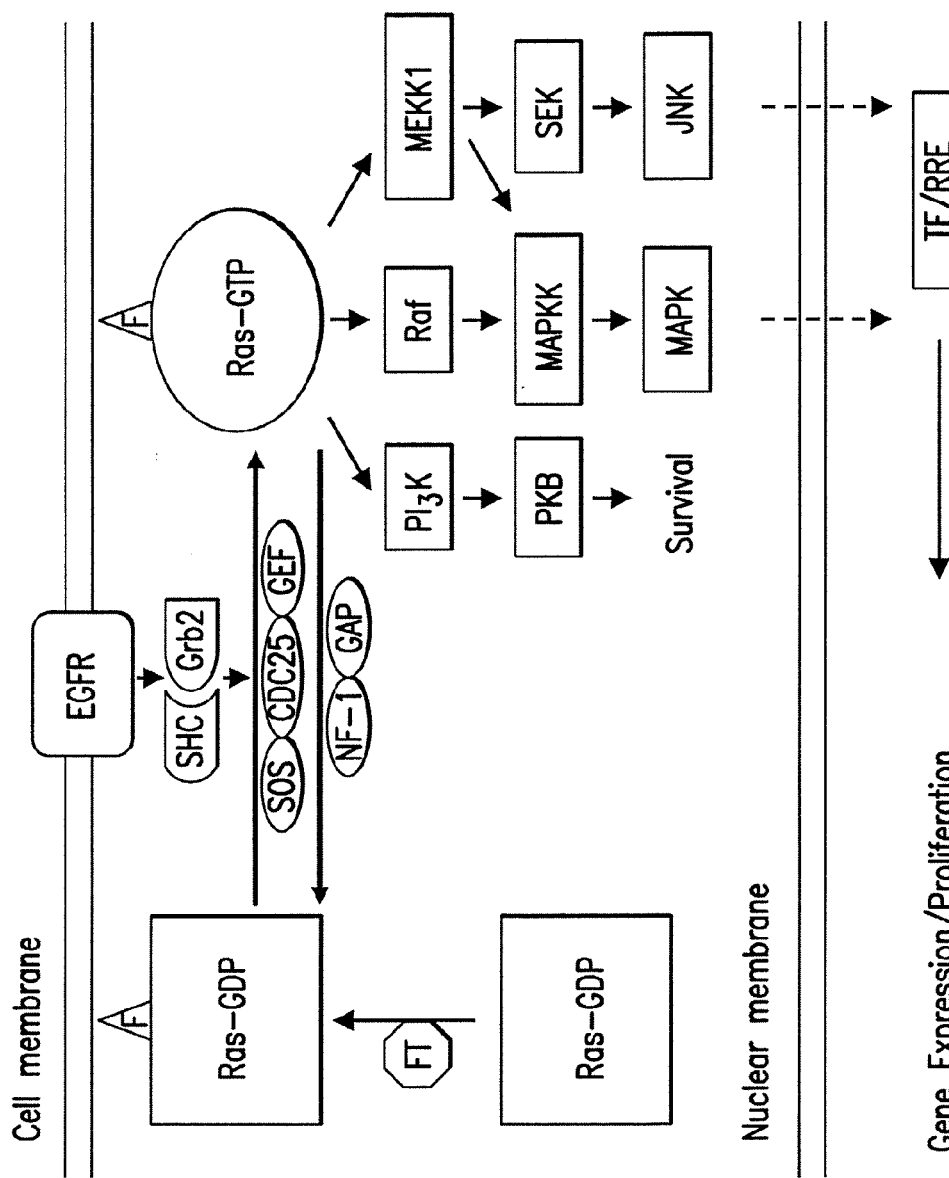

Kim YT, Kim J, Jang YH, Lee WJ, Ryu JK, Park YK, Kim SW, Kim WH, Yoon YB, Kim CY (2001). Genetic alterations in gallbladder adenoma, dysplasia and carcinoma. Cancer Lett. 169(1):59-68.

Mhashilkar AM, Schrock RD, Hindi M, Liao J, Sieger K, Kourouma F, Zou-Yang XH, Onishi E, Takh O, Vedvick TS, Fanger G, Stewart L, Watson GJ, Snary D, Fisher PB, Saeki T, Roth JA, Ramesh R, Chada S (2001). Melanoma differentiation associated gene-7 (mda-7): a novel anti-tumor gene for cancer gene therapy. Mol. Med. 7(4):271-282.

Nakano M, Aoki K, Matsumoto N, Ohnami S, Hatanaka K, Hibi T, Terada M, Yoshida T (2001). Suppression of colorectal cancer growth using an adenovirus vector expressing an antisense K-ras RNA. Mol. Ther. 3(4):491-499.

Noda N, Matsuzoe D, Konno T, Kawahara K, Yamashita Y, Shirakusa T (2001). K-ras gene mutations in non-small cell lung cancer in Japanese. Oncol. Rep. 8(4):889-92.

Peng XY, Won JH, Rutherford T, Fujii T, Zelterman D, Pizzorno G, Sapi E, Leavitt J, Kacinski B, Crystal R, Schwartz P, Deisseroth A (2001). The use of the L-plastin promoter for adenoviral-mediated, tumor-specific gene expression in ovarian and bladder cancer cell lines. Cancer Res. 61(11):4405-4413.

Perrais M, Pigny P, Ducourouble MP, Petitprez D, Porchet N, Aubert JP, Van Seuningen I (2001). Characterization of human mucin gene MUC4 promoter: importance of growth factors and proinflammatory cytokines for its regulation in pancreatic cancer cells. J. Biol. Chem. 276(33):30923-30933.

Rekasi Z, Varga JL, Schally AV, Plonowski A, Halmos G, Csernus B, Armatis P, Groot K (2001). Antiproliferative actions of growth hormone-releasing hormone antagonists on MiaPaCa-2 human pancreatic cancer cells involve cAMP independent pathways. Peptides 22(6):879-886.

Sakamoto A, Odo Y, Adachi T, Oshiro Y, Tamiya S, Tanaka K, Matsuda S, Iwamoto Y, Tsuneyoshi M (2001). H-ras oncogene mutation in dedifferentiated chondrosarcoma: polymerase chain reaction-restriction fragment length polymorphism analysis. Mod. Pathol. 14(4):343-349.

Shah SA, Potter MW, McDade TP, Ricciardi R, Perugini RA, Elliott PJ, Adams J, Callery MP (2001). 26S proteasome inhibition induces apoptosis and limits growth of human pancreatic cancer. J. Cell. Biochem. 82(1):110-122.

Sherman WH, Fine RL (2001). Combination gemcitabine and docetaxel therapy in advanced adenocarcinoma of the pancreas. Oncology 60(4):316-321.

Su et al., (2001) "A combinatorial approach for selectively inducing programmed cell death in human pancreatic cancer cells", PNAS 98: 10332-10337.

Tanaka M, Inase N, Miyake S, Yoshizawa Y (2001). Neuron specific enolase promoter for suicide gene therapy in small cell lung carcinoma. Anticancer Res. 21(1A):291-294.

Weihrauch M, Benicke M, Lehnert G, Wittekind C, Wrbitzky R, Tannapfel A (2001). Frequent k-ras-2 mutations and p16(INK4A) methylation in hepatocellular carcinomas in workers exposed to vinyl chloride. Br. J. Cancer 84(7):982-989.

Xie X, Zhao X, Liu Y, Young CY, Tindall DJ, Slawin KM, Spencer DM (2001). Robust prostate-specific expression for targeted gene therapy based on the human kallikrein 2 promoter. Human Gene Ther. 12(5):549-61.

Adachi, Y. Reynolds PN, Yamamoto M, Grizzle WE, Overturf K, Matsubara S, Muramatsu T, Curiel DT (2000). Midkine promoter-based adenoviral vector gene delivery for pediatric solid tumors. Cancer Res. 60(16):4305-4310.

Adjei AA, Davis JN, Erlichman C, Svingen PA, Kaufmann SH (2000). Comparison of potential markers of farnesyltransferase inhibition. Clin. Cancer Res. 6(6):2318-2325.

Almeida EA, Ilic D, Han Q, Hauck CR, Jin F, Kawakatsu H, Schlaepfer DD, Damsky CH (2000). Matrix survival signaling: from fibronectin via focal adhesion kinase to c-Jun NH(2)-terminal kinase. J. Cell Biol. 149(3):741-754.

Basolo F, Pisaturo F, Pollina LE, Fontanini G, Elisei R, Molinaro E, Iacconi P, Miccoli P, Pacini F (2000). N-ras mutation in poorly differentiated thyroid carcinomas: correlation with bone metastases and inverse correlation to thyroglobulin expression. Thyroid 10(1):19-23.

Crespo P, León J (2000). Ras proteins in the control of the cell cycle and cell differentiation. Cell. Mol. Life Sci. 57(11):1613-1636.

Curran MA, Kaiser SM, Achacoso PL, Nolan GP (2000). Efficient transduction of nondividing cells by optimized feline immunodeficiency virus vectors. Mol. Ther. 1(1):31-38.

Eggerding FA (2000). Fluorescent oligonucleotide ligation technology for identification of ras oncogene mutations. Mol. Biotechnol. 14(3):223-233.

Garcia JM, Gonzalez R, Silva JM, Dominguez G, Vegazo IS, Gamallo C, Provencio M, Espana P, Bonilla F (2000). Mutational status of K-ras and TP53 genes in primary sarcomas of the heart. Br. J. Cancer 82(6):1183-1185.

Giehl K, Seidel B, Gierschik P, Adler G, Menke A (2000). TGFbeta1 represses proliferation of pancreatic carcinoma cells which correlates the Smad4-independent inhibition of ERK activation. Oncogene 19(39):4531-4541.

Gire V, Marshall C, Wynford-Thomas D (2000). PI-3-kinase is an essential anti-apoptotic effector in the proliferative response of primary human epithelial cells to mutant RAS. Oncogene 19(19):2269-2276.

Inase N, Horita K, Tanaka M, Miyake S, Ichioka M, Yoshizawa Y (2000). Use of gastrin-releasing peptide promoter for specific expression of thymidine kinase gene in small-cell lung carcinoma cells. Int. J. Cancer 85(5):716-719.

Kolch W (2000). Meaningful relationships: the regulation of the Ras/Raf/MEK/ERK pathway by protein interactions. Biochem. J. 351(Pt 2):289-305.

Komata et al., (2000) "Combination therapy of malignant glioma cells with 2-5A antisense telomerase RNA and recombinant adenovirus p53", Gene Ther. 7(24): 2071-2079.

Lantry LE, Zhang Z, Yao R, Crist KA, Wang Y, Ohkanda J, Hamilton AD, Sebti SM, Lubet RA, You M (2000). Effect of farnesyltransferase inhibitor FTI-276 on established lung adenomas from A/J mice induced by 4-(methylnitrosamino)-1-(3-pyridyl)-1-butanone.Carcinogenesis 21(1):113-116.

Lebedeva I, Rando R, Ojwang J, Cossum P, Stein CA (2000). Bcl-xL in prostate cancer cells: effects of overexpression and down-regulation on chemosensitivity. Cancer Res. 60(21):6052-6060.

Lorenz M, Heinrich S, Staib-Sebler E, Kohne CH, Wils J, Nordlinger B, Encke A (2000). Regional chemotherapy in the treatment of advanced pancreatic cancer—is it relevant. Eur. J. Cancer 36(8):957-965.

Madireddi MT, Su ZZ, Young CS, Goldstein NI, Fisher PB (2000). Mda-7, a novel melanoma differentiation associated gene with promise for cancer gene therapy. Adv. Exptl. Med. Biol. 465:239-261.

Nakao M, Janssen JW, Seriu T, Bartram CR (2000). Rapid and reliable detection of N-ras mutations in acute lymphoblastic leukemia by melting curve analysis using LightCycler technology. Leukemia 14(2):312-315.

O'Keefe DS, Uchida A, Bacich DJ, Watt FB, Martorana A, Molloy PL, Heston WD (2000). Prostate-specific suicide gene therapy using the prostate-specific membrane antigen promoter and enhancer. Prostate 45(2):149-157.

Park JS, Qiao L, Gilfor D, Yang MY, Hylemon PB, Benz C, Darlington G, Firestone G, Fisher PB, Dent P (2000). A role for both Ets and C/EBP transcription factors and mRNA stabilization in the MAPK-dependent increase in p21 (Cip-1/WAF1/mda6) protein levels in primary hepatocytes. Mol. Biol. Cell. 11(9):2915-2932.

Pawlak W, Zolnierek J, Sarosiek T, Szczylik C (2000). Antisense therapy in cancer. Cancer Treat Rev. 26(5):333-350.

Reed JC (2000). Mechanisms of apoptosis. Am J. Pathol. 157(5):1415-1430.

Reuther GW, Der CJ (2000). The Ras branch of small GTPases: Ras family members don't fall far from the tree. Curr. Opin. Cell Biol. 12(2):157-165.

Rosenberg L (2000). Pancreatic cancer: a review of emerging therapies. Drugs 59(5):1071-1089.

Saeki T, Mhashilkar A, Chada S, Brnach C, Roth JA, Ramesh R (2000). Tumor-suppressive effects by adenovirus-mediated mda-7 gene transfer in non-small cell lung cancer cell in vitro. Gene Ther. 7(23):2051-2057.

Schlitzer M, Sattler I (2000). Non-thiol farnesyltransferase inhibitors: the concept of benzophenone-based bisubstrate analogue farnesyltransferase inhibitors. Eur J Med Chem 35(7-8):721-726.

Somia N, Verma IM (2000). Gene therapy: trials and tribulations. Nat. Rev. Genet. 1(2):91-99.

Takeuchi M, Shichinohe T, Senmaru N, Miyamoto M, Fujita H, Takimoto M, Kondo S, Katoh H, Kuzumaki N (2000). The dominant negative H-ras mutant, N116Y, suppresses growth of metastatic human pancreatic cancer cells in the liver of nude mice. Gene Ther. 7(6):518-526.

Watanabe T, Sakamoto A, Tamiya S, Oda Y, Masuda K, Tsuneyoshi M (2000). H-ras-1 point mutation in malignant peripheral nerve sheath tumors: polymerase chain reaction restriction fragment length polymorphism analysis and direct sequencing from paraffin-embedded tissues. Int. J. Mol. Med. 5(6):605-608.

Case SS, Price MA, Jordan CT, Yu XJ, Wang L, Bauer G, Haas DL, Xu D, Stripecke R, Naldini L, Kohn DB, Crooks GM (1999). Stable transduction of quiescent CD34(+)CD38(-) human hematopoietic cells by HIV-1-based lentiviral vectors. Proc. Natl. Acad. Sci. U.S.A. 96(6): 2988-2993.

Connelly S (1999). Adenoviral vectors for liver-directed gene therapy. Curr. Opin. Mol. Ther. 1(5):565-572.

Friess H, Kleeff J, Korc M, Buchler MW (1999). Molecular aspects of pancreatic cancer and future perspectives. Dig. Surg. 16(4):281-290.

Hardcastle IR, Rowlands MG, Barber AM, Grimshaw RM, Mohan MK, Nutley BP, Jarman M (1999). Inhibition of protein prenylation by metabolites of limonene. Biochem. Pharm. 57(7):801-809.

Hilgers W, Kern SE (1999). Molecular genetic basis of pancreatic adenocarcinoma. Genes Chromosomes Cancer 26(1):1-12.

Katabi MM, Chan HL, Karp SE, Batist G (1999). Hexokinase type II: a novel tumor-specific promoter for gene-targeted therapy differentially expressed and regulated in human cancer cells. Human Gene Ther. 10:155-164.

Kita K, Saito S, Morioka CY, Watanabe A (1999). Growth inhibition of human pancreatic cancer cell lines by anti-sense oligonucleotides specific to mutated K-ras genes. Intl. J. Cancer 80(4):553-558.

International Patent Application No. PCT/US99/05996, Publication No. WO 99/47709, by Maki et al, published in English on Sep. 23, 1999. Methods for identifying anticancer agents.

Morral N, O'Neal W, Rice K, Leland M, Kaplan J, Piedra PA, Zhou H, Parks RJ, Velji R, Aguilar-Cordova E, Wadsworth S, Graham FL, Kochanek S, Carey KD, Beaudet AL (1999). Administration of helper-dependent adenoviral vectors and sequential delivery of different vector serotype for long-term liver-directed gene transfer in baboons. Proc. Natl. Acad. Sci. U.S.A. 96(22):12816-12821.

Pan CX, Koeneman KS (1999). A novel tumor-specific gene therapy for bladder cancer. Med. Hypotheses 53(2):130-135.

Polo JM, Belli BA, Driver DA, Frolov I, Sherrill S, Hariharan MJ, Townsend K, Perri S, Mento SJ, Jolly DJ, Chang SM, Schlesinger S, Dubensky TW Jr (1999). Stable alphavirus packaging cell lines for Sindbis virus and Semliki Forest virus-derived vectors. Proc. Natl. Acad. Sci. U.S.A. 96(8):4598-4603.

Stackhouse MA, Buchsbaum DJ, Kancharla SR, Grizzle WE, Grimes C, Laffoon K, Pederson LC, Curiel DT (1999). Specific membrane receptor gene expression targeted with radiolabeled peptide employing the erbB-2 and DF3 promoter elements in adenoviral vectors. Cancer Gene Ther. 6(3):209-219.

Varras MN, Sourvinos G, Diakomanolis E, Koumantakis E, Flouris GA, Lekka-Katsouli J, Michalas S, Spandidos DA (1999). Detection and clinical correlations of ras gene mutations in human ovarian tumors. Oncology 56(2):89-96.

Zhang WW (1999). Development and application of adenoviral vectors for gene therapy of cancer. Cancer Gene Ther. 6(2):113-138.

Blaszkowsky L (1998). Treatment of advanced and metastatic pancreatic cancer. Front. Biosci. 3:E214-E225.

Campbell SL, Khosravi-Far R, Rossman KL, Clark GJ, Der CJ (1998). Increasing complexity of Ras signaling. Oncogene 17(11):1395-1413.

Ding et al., (1998) "Co-packaging of sense and antisense RNAs: a novel strategy for blocking HIV-1 replication", Nucl. Acids Res. 26(13): 3270-3278.

Green DR, Reed JC (1998). Mitochondria and apoptosis. Science 281(5381):1309-1312.

Hao Y, Zhang J, Lu Y, Yi C, Qian W, Cui J (1998). The role of ras gene mutation in gastric cancer and precancerous lesions. J. Tongji Med. Univ. 18(3):141-144.

Longnecker DS, Terhune PG (1998). What is the true rate of K-ras mutation in carcinoma of the pancreas? Pancreas 17(4):323-324.

Miyakis S, Sourvinos G, Spandidos DA (1998). Differential expression and mutation of the ras family genes in human breast cancer. Biochem. Biophys. Res. Commun. 251(2):609-612.

Olsen JC (1998). Gene transfer vectors derived from equine infectious anemia virs. Gene Ther. 5(11):1481-1487.

Perugini RA, McDade TP, Vittimberga FJ Jr, Callery MP (1998). The molecular and cellular biology of pancreatic cancer. Crit. Rev. Eukaryotic Gene Express. 8(3-4):377-393.

Regine WF, John WJ, Mohiuddin M (1998). Adjuvant therapy for pancreatic cancer: current status. Front. Biosci. 3:E186-E192.

Su ZZ, Madireddi MT, Lin JJ, Young CS, Kitada S, Reed JC, Goldstein NI, Fisher PB (1998). The cancer growth suppressor gene mda-7 selectively induces apoptosis in human breast cancer cells and inhibits tumor growth in nude mice. Proc. Natl. Acad. Sci. U.S.A. 95(24):14400-14405.

Advani et al. (1997) Radiogenic therapy: on the interaction of viral therapy and ionizing radiation for improving local control of tumors. Semin Oncol. 24(6): 633-638.

Aoki K, Yoshida T, Matsumoto N, Ide H, Sugimura T, Terada M (1997). Suppression of Ki-ras p21 levels leading to growth inhibition of pancreatic cancer cell lines with Ki-ras mutation but not those without Ki-ras mutation. Mol. Carcinogen. 20(2):251-258.

Grendys EC Jr, Barnes WA, Weitzel J, Sparkowski J, Schlegel R (1997). Identification of H, K, and N-ras point mutations in stage IB cervical carcinoma. Gynecol. Oncol. 65(2):343-347.

Maltzman TH, Mueller BA, Schroeder J, Rutledge JC, Patterson K, Preston-Martin S, Faustman EM (1997). Ras oncogene mutations in childhood brain tumors. Cancer Epidemio. Biomarkers Prev. 6(4):239-243.

Rampino N, Yamamoto H, Ionov Y, Li Y, Sawai H, Reed JC, Perucho M (1997). Somatic frameshift mutations in the BAX gene in colon cancers of the microsatellite mutator phenotype. Science 275(5302):967-969.

Saito S, Hata M, Fukuyama R, Sakai K, Kudoh J, Tazaki H, Shimizu N (1997). Screening of H-ras gene point mutations in 50 cases of bladder carcinoma. Int. J. Urol. 4(2):178-185.

Takakuwa K, Fujita K, Kikuchi A, Sugaya S, Yahata T, Aida H, Kurabayashi T, Hasegawa I, Tanaka K (1997). Direct intratumoral gene transfer of the herpes simplex virus thymidine kinase gene with DNA-liposome complexes: growth inhibition of tumors and lack of localization in normal tissues. Jpn. J. Cancer Res. 88(2):166-175.

Boyce FM, Bucher NL (1996). Baculovirus-mediated gene transfer into mammalian cells. Proc. Natl. Acad. Sci. U.S.A. 93(6):2348-2352.

Jiang H, Su ZZ, Lin JJ, Goldstein NI, Young CS, Fisher PB (1996). The melanoma differentiation associated gene mda-7 suppresses cancer cell growth. Proc. Natl. Acad. Sci. U.S.A. 93(17):9160-9165.

Lan KH, Kanai F, Shiratori Y, Okabe S, Yoshida Y, Wakimoto H, Hamada H, Tanaka T, Ohashi M, Omata M (1996). Tumor-specific gene expression in carcinoembryonic antigen-producing gastric cancer cells using adenovirus vectors. Gastroenterol. 111(5):1241-1251.

Shichinohe T, Senmaru N, Furuuchi K, Ogiso Y, Ishikura H, Yoshiki T, Takahashi T, Kato H, Kuzumaki N (1996). Suppression of pancreatic cancer by the dominant negative ras mutant, N116Y. J. Surg Res. 66(2):125-130.

Stein CA (1996). Phosphorothioate antisense oligodeoxynucleotides: questions of specificity. Trends Biotechnol. 14(5):147-149.

Strayer DS, Milano J (1996). SV40 mediates stable gene transfer in vivo. Gene Ther. 3(7):581-587.

Aoki K, Yoshida T, Sugimura T, Terada M (1995). Liposome-mediated in vivo gene transfer of antisense K-ras construct inhibits pancreatic tumor dissemination in the murine peritoneal cavity. Cancer Res. 55(17):3810-3816.

Huard J, Lochmuller H, Acsadi G, Jani A, Massie B, Karpati G (1995). The route of administration is a major determinant of the transduction efficiency of rat tissues by adenoviral recombinants. Gene Ther. 2(2):107-115.

Ido A, Nakata K, Kato Y, Nakao K, Murata K, Fujita M, Ishii N, Tamaoki T, Shiku H, Nagataki S (1995). Gene therapy for hepatoma cells using a retrovirus vector carrying herpes simplex virus thymidine kinase gene under the control of human alpha-fetoprotein gene promoter. Cancer Res. 55(14):3105-3109.

Jiang H, Lin JJ, Su ZZ, Goldstein NI, Fisher PB (1995). Subtraction hybridization identifies a novel melanoma differentiation associated gene, mda-7, modulated during human melanoma differentiation, growth and progression. Oncogene 11(12):2477-2486.

Lebowitz PF, Davide JP, Prendergast GC (1995). Evidence that farnesyltransferase inhibitors suppress Ras transformation by interfering with Rho activity. Mol Cell Biol 15(12):6613-6622.

Martin SJ, Reutelingsperger CP, McGahon AJ, Rader JA, van Schie RC, LaFace DM, Green DR (1995). Early redistribution of plasma membrane phosphatidylserine is a general feature of apoptosis regardless of the initiating stimulus: inhibition by overexpression of Bcl-2 and Abl. J. Exp. Med. 182(5:1545-1556.

Sakakura C, Hagiwara A, Tsujimoto H, Ozaki K, Sakakibara T, Oyama T, Ogaki M, Imanishi T, Yamazaki J, Takahashi T (1995). Inhibition of colon cancer cell proliferation by antisense oligonucleotides targeting the messenger RNA of the Ki-ras gene. Anticancer Drugs 6(4):553-561.

Su ZZ, Lin J, Prewett M, Goldstein NI, Fisher PB (1995). Apoptosis mediates the selective toxicity of caffeic acid phenethyl ester (CAPE) toward oncogene-transformed rat embryo fibroblast cells. Anticancer Res. 15:1841-1848.

Su ZZ; Yemul S; Estabrook A; Friedman RM; Zimmer SG; Fisher PB (1995). Transcriptional switching model for the regulation of tumorigenesis and metastasis by the Ha-ras oncogene: transcriptional changes in the Ha-ras tumor suppressor gene lysyl oxidase. Intl. J. Oncol. 7(6):1279-1284.

Bett AJ, Haddara W, Prevec L, Graham FL (1994). An efficient and flexible system for construction of adenovirus vectors with insertions or deletions in early regions 1 and 3. Proc. Natl. Acad. Sci. U.S.A. 91(19):8802-8806.

Falck-Pedersen E, Heinflink M, Alvira M, Nussenzveig DR, Gershenorn MC (1994). Expression of thyrotropin-releasing hormone receptors by adenovirus-mediated gene transfer reveals that thyrotropin-releasing hormone desensitization is cell specific. Mol. Pharmacol. 45(4):684-689.

Hayashi Y, DePaoli AM, Burant CF, Refetoff S (1994). Expression of a thyroid hormone-responsive recombinant gene introduced into adult mice livers by replication-defective adenovirus can be regulated by endogenous thyroid hormone receptor. J. Biol. Chem. 269(39):23872-23875.

Kohl NE, Wilson FR, Mosser SD, Giuliani E, deSolms SJ, Conner MW, Anthony NJ, Holtz WJ, Gomez RP, Lee TJ, et al. (1994). Protein farnesyltransferase inhibitors block the growth of ras-dependent tumors in nude mice. Proc. Natl. Acad. Sci. U.S.A. 91(19):9141-9145.

Rossi JJ (1994) Practical Ribozymes, Making Ribozymes Work In Cells. Curr. Biol. 4(5):469-471.

Jiang H, Fisher PB (1993). A sensitive and efficient subtraction hybridization protocol for the identification of genes differentially regulated during the induction of differentiation in human melanoma cells. Mol. Cell. Different. 1(3):285-299.

Kohl NE, Mosser SD, deSolms SJ, Giuliani EA, Pompliano DL, Graham SL, Smith RL, Scolnick EM, Oliff A, Gibbs JB (1993). Selective inhibition of ras-dependent transformation by a farnesyltransferase inhibitor. Science 260(5116):1934-1937.

Li Q, Kay MA, Finegold M, Stratford-Perricaudet LD, Woo SL (1993). Assessment of recombinant adenoviral vectors for hepatic gene therapy. Hum. Gene Ther. 4(4):403-409.

Mastrangeli A, Danel C, Rosenfeld MA, Stratford-Perricaudet L, Perricaudet M, Pavirani A, Lecocq JP, Crystal RG (1993). Diversity of airway epithelial cell targets for in vivo recombinant adenovirus-mediated gene transfer. J. Clin. Invest. 91(1):225-234.

Ragot T, Vincent N, Chafey P, Vigne E, Gilgenkrantz H, Couton D, Cartaud J, Briand P, Kaplan JC, Perricaudet M, et al. (1993). Efficient adenovirus-mediated transfer of a human minidystrophin gene to skeletal muscle of mdx mice. Nature 361(6413):647-650.

Stein CA, Cheng YC (1993). Antisense oligonucleotides as therapeutic agents—is the bullet really magic? Science 261(5124):1004-1012.

Dent P, Haser W, Haystead TA, Vincent LA, Roberts TM, Sturgill TW (1992). Activation of mitogen-activated protein kinase kinase by v-Raf in NIH 3T3 cells and in vitro. Science 257(5075):1404-1407.

Gavrieli Y, Sherman Y, Ben-Sasson SA (1992). Identification of programmed cell death in situ via specific labeling of nuclear DNA fragmentation. J. Cell Biol. 119(3):493-501.

Helene C, Thuong NT, Harel-Bellan A (1992). Control of gene expression by triple helix-forming oligonucleotides. The antigene strategy. Ann. N.Y. Acad. Sci. 660:27-36.

Jaffe HA, Danel C, Longenecker G, Metzger M, Setoguchi Y, Rosenfeld MA, Gant TW, Thorgeirsson SS, Stratford-Perricaudet LD, Perricaudet M, et al. (1992). Adenovirus-mediated in vivo gene transfer and expression in normal rat liver. Nat. Gen. 1(5):372-378.

Legendre JY, Szoka FC Jr. (1992). Delivery of plasmid DNA into mammalian cell lines using pH-sensitive liposomes: comparison with cationic liposomes. Pharmaceutical Research 9(10):1235-1242.

Lemoine NR, Jain S, Hughes CM, Staddon SL, Maillet B, Hall PA, Kloppel G (1992). Ki-ras oncogene activation in preinvasive pancreatic cancer. Gastroenterol. 102(1):230-236.

Maher LJ 3rd. (1992). DNA triple-helix formation: an approach to artificial gene repressors? Bioessays 14(12):807-815.

Ozaki H (1992). Improvement of pancreatic cancer treatment from the Japanese experience in the 1980s. Int. J. Pancreatol. 12(1):5-9.

Quantin B, Perricaudet LD, Tajbakhsh S, Mandel JL (1992). Adenovirus as an expression vector in muscle cells in vivo. Proc. Natl. Acad. Sci. U.S.A. 89(7):2581-2584.

Rosenfeld MA, Yoshimura K, Trapnell BC, Yoneyama K, Rosenthal ER, Dalemans W, Fukayama M, Bargon J, Stier LE, Stratford-Perricaudet L, et al. (1992). In vivo transfer of the human cystic fibrosis transmembrane conductance regulator gene to the airway epithelium. Cell 68(1):143-155.

Sutter G, Moss B (1992). Nonreplicating vaccinia vector efficiently expresses recombinant genes. Proc. Natl. Acad. Sci. U.S.A. 89(22):10847-10851.

Tanaka K, Takechi M, Asaoku H, Dohy H, Kamada N (1992). A high frequency of N-RAS oncogene mutations in multiple myeloma. Int. J. Hematol. 56(2):119-127.

Walsh CE, Liu JM, Xiao X, Young NS, Nienhuis AW, Samulski RJ (1992). Regulated high level expression of a human gamma-globin gene introduced into erythroid cells by an adeno-associated virus vector. Proc. Natl. Acad. Sci. U.S.A. 89(15):7257-7261.

Warshaw AL, Fernandez-del Castillo C (1992). Pancreatic carcinoma. N. Engl. J. Med. 326(7):455-465.

Helen C (1991). The anti-gene strategy: control of gene expression by triplex-forming-oligonucleotides. Anticancer Drug. Des. 6(6):569-584.

Marion MJ, Froment O, Trepo C (1991). Activation of Ki-ras gene by point mutation in human liver angiosarcoma associated with vinyl chloride exposure. Mol. Carcinog. 4(6):450-454.

Nielsen PE, Egholm M, Berg RH, Buchardt O. (1991). Sequence-selective recognition of DNA by strand displacement with a thymine-substituted polyamide. Science 254(5037):1497-1500.

Rosenfeld MA, Siegfried W, Yoshimura K, Yoneyama K, Fukayama M, Stier LE, Paakko PK, Gilardi P, Stratford-Perricaudet LD, Perricaudet M, et al. (1991). Adenovirus-mediated transfer of a recombinant alpha 1-antitrypsin gene to the lung epithelium in vivo. Science 252(5004):431-434.

Wang Q, Konan V, Taylor MW (1991). Expression of the APRT gene in an adenovirus vector system as a model for studying gene therapy. Adv. Exp. Med. Biol. 309B:61-66.

Wu GY, Wu CH (1991). Delivery systems for gene therapy. Biotherapy 3(1):87-95.

Arbuck SG (1990). Overview of chemotherapy for pancreatic cancer. Int. J. Pancreatol. 7(1-3):209-222.

Cohn I Jr. (1990). Overview of pancreatic cancer, 1989. Int. J. Pancreatol. 7(1-3):1-11.

Geller AI, Freese A (1990). Infection of cultured central nervous system neurons with a defective herpes simplex virus 1 vector results in stable expression of *Escherichia coli* beta-galactosidase. Proc. Natl. Acad. Sci. U.S.A. 87(3):1149-1153.

Stratford-Perricaudet LD, Levrero M, Chasse JF, Perricaudet M, Briand P (1990). Evaluation of the transfer and expression in mice of an enzyme-encoding gene usinga human adenovirus vector. Human Gene Ther. 1(3):241-256.

Wolff JA, Malone RW, Williams P, Chong W, Acsadi G, Jani A, Felgner PL (1990). Direct gene transfer into mouse muscle in vivo. Science 247(4949 Pt1):1465-1468.

Ausubel et al. (1989). Current Protocols in Molecular Biology, vol. I, Green Publishing Associates, Inc., and John Wiley & Sons, Inc. New York, at p. 2.10.1 to 2.10.16 (with page numbers as per Supplement 55, 2001).

Miller AD, Rosman GJ (1989). Improved retroviral vectors for gene transfer and expression. Biotechniques 7(9):981-990.

Yamaguchi K, Enjoji M (1989). Carcinoma of the pancreas: a clinicopathologic study of 96 cases with immunohistochemical observations. Jpn. J. Clin. Oncol. 19(1):14-22.

Almoguera C, Shibata D, Forrester K, Martin J, Arnheim N, Perucho M (1988). Most human carcinomas of the exocrine pancreas contain mutant c-K-ras genes. Cell 53(4):549-554.

Berkner KL (1988). Development of adenovirus vectors for the expression of heterologous genes. Biotechniques 6(7):616-624.

Hambor JE, Hauer CA, Shu HK, Groger RK, Kaplan DR, Tykocinski ML (1988). Use of an Epstein-Barr virus episomal replicon for anti-sense RNA-mediated gene inhibition in a human cytotoxic T-cell clone. Proc. Natl. Acad. Sci. U.S.A. 85(11):4010-4014.

Haseloff J, Gerlach WL (1988). Simple RNA enzymes with new and highly specific endoribonuclease activities. Nature 334(6183):585-591.

McGrory WJ, Bautista DS, Graham FL (1988). A simple technique for the rescue of early region I mutations into infectious human adenovirus type 5. Virology 163(2):614-617.

Nicolau C, Legrand A, Grosse E (1987). Liposomes as carriers for in vivo gene transfer and expression. Methods in Enzymology 149:157-176.

Been MD, Cech TR (1986). One binding site determines sequence specificity of Tetrahymena pre-rRNA self-splicing, trans-splicing, and RNA enzyme activity. Cell 47(2):207-216.

Zaug AJ, Cech TR (1986). The intervening sequence RNA of Tetrahymena is an enzyme. Science 231(4737):470-475.

Zaug AJ, Been MD, Cech TR (1986). The Tetrahymena ribozyme acts like an RNA restriction endonuclease. Nature 324(6096):429-433.

Zaug AJ, Kent JR, Cech TR (1984). A labile phosphodiester bond at the ligation junction in a circular intervening sequence RNA. Science 224(4649):574-578.

Volkert FC, Young CS (1983). The genetic analysis of recombination using adenovirus overlapping terminal DNA fragments. Virol. 125(1):175-193.

Graham FL, Smiley J, Russell WC, Nairn R (1977). Characteristics of a human cell line transformed by DNA from human adenovirus type 5. J. Gen. Virol. 36(1):59-72.

* cited by examiner

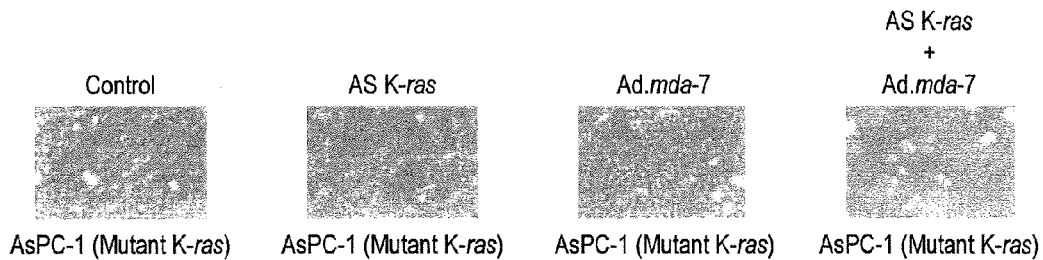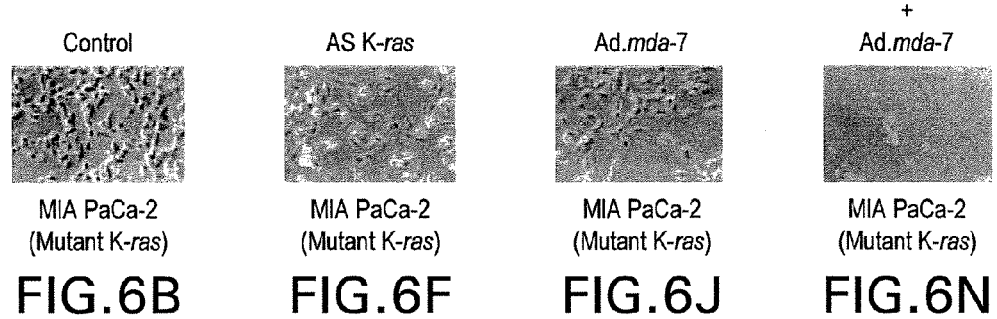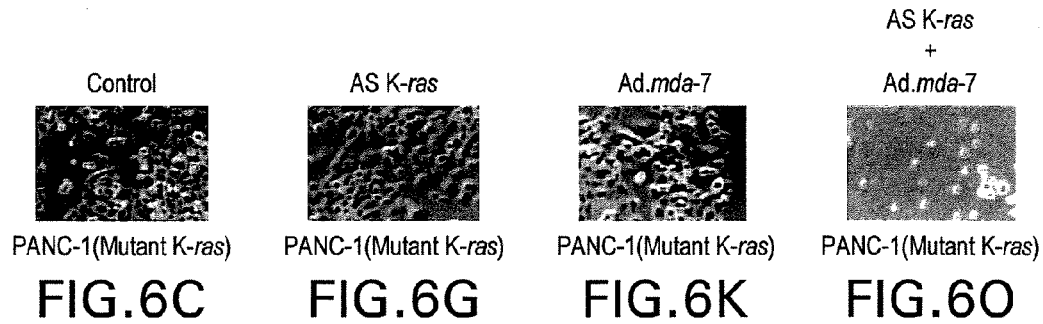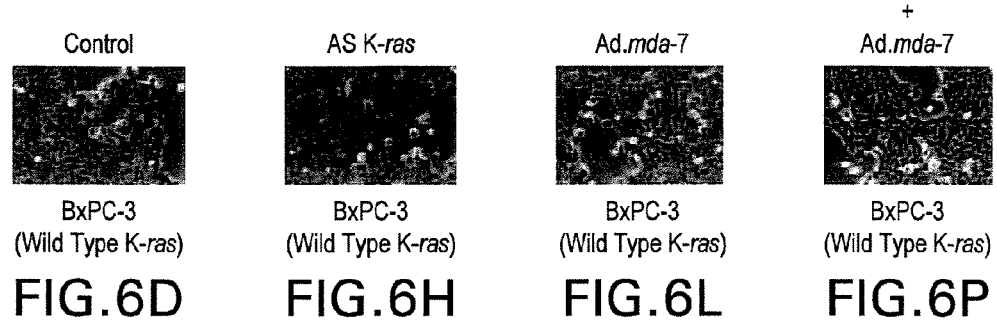

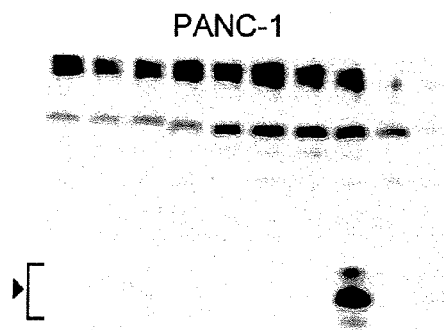
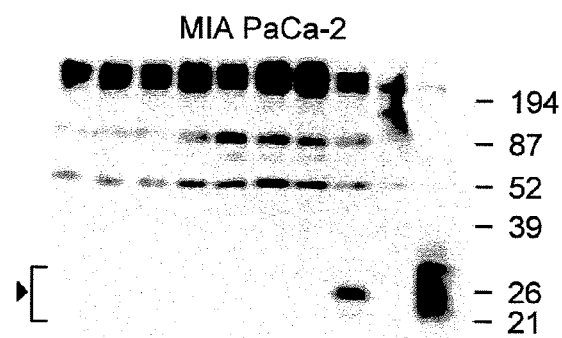
FIG.10A  FIG.10B
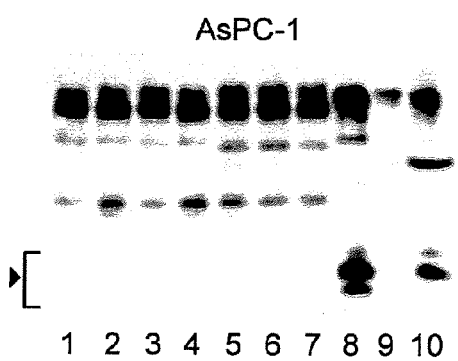
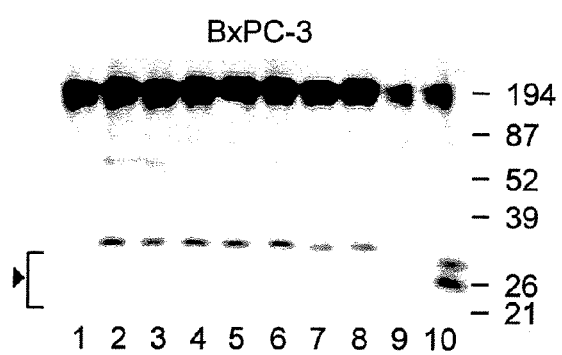
FIG.10C  FIG.10D

SEQUENCE LISTING

```
<160> NUMBER OF SEQ ID NOS: 17

<210> SEQ ID NO 1
<211> LENGTH: 1700
<212> TYPE: DNA
<213> ORGANISM: Homo sapiens
<220> FEATURE:
<221> NAME/KEY: misc_feature
<222> LOCATION: (275)...(895)
<223> OTHER INFORMATION: CDS = 275-895

<400> SEQUENCE: 1
cttgcctgca aacctttact tctgaaatga cttccacggc tgggacggga accttccacc      60
cacagctatg cctctgattg gtgaatggtg aaggtgcctg tctaactttt ctgtaaaaag     120
aaccagctgc ctccaggcag ccagccctca agcatcactt acaggaccag agggacaaga     180
catgactgtg atgaggagct gctttcgcca atttaacacc aagaagaatt gaggctgctt     240
gggaggaagg ccaggaggaa cacgagactg agagatgaat tttcaacaga ggctgcaaag     300
cctgtggact ttagccagac ccttctgccc tcctttgctg gcgacagcct ctcaaatgca     360
gatggttgtg ctcccttgcc tgggttttac cctgcttctc tggagccagg tatcaggggc     420
ccagggccaa gaattccact ttgggccctg ccaagtgaag ggggttgttc cccagaaact     480
gtgggaagcc ttctgggctg tgaaagacac tatgcaagct caggataaca tcacgagtgc     540
ccggctgctg cagcaggagg ttctgcagaa cgtctcggat gctgagagct gttaccttgt     600
ccacaccctg ctggagttct acttgaaaac tgttttcaaa aactaccaca atagaacagt     660
tgaagtcagg actctgaagt cattctctac tctggccaac aactttgttc tcatcgtgtc     720
acaactgcaa cccagtcaag aaaatgagat gttttccatc agagacagtg cacacaggcg     780
gtttctgcta ttccggagag cattcaaaca gttggacgta gaagcagctc tgaccaaagc     840 ccttgggaa gtggacattc ttctgacctg gatgcagaaa ttctacaagc tctgaatgtc      900
tagaccagga cctccctccc cctggcactg gtttgttccc tgtgtcattt caaacagtct     960
cccttcctat gctgttcact ggacacttca cgcccttggc catgggtccc attcttggcc    1020
caggattatt gtcaaagaag tcattctttta agcagcgcca gtgacagtca gggaaggtgc    1080
ctctggatgc tgtgaagagt ctacagagaa gattcttgta tttattacaa ctctatttaa    1140
```

-continued

```
ttaatgtcag tatttcaact gaagttctat ttatttgtga gactgtaagt tacatgaagg    1200
cagcagaata ttgtgcccca tgcttcttta cccctcacaa tccttgccac agtgtggggc    1260
agtggatggg tgcttagtaa gtacttaata aactgtggtg ctttttttgg cctgtctttg    1320
gattgttaaa aaacagagag ggatgcttgg atgtaaaact gaacttcaga gcatgaaaat    1380
cacactgtct gctgatatct gcagggacag agcattgggg tgggggtaag gtgcatctgt    1440
ttgaaaagta aacgataaaa tgtggattaa agtgcccagc acaaagcaga tcctcaataa    1500
acatttcatt tcccacccac actcgccagc tcaccccatc atccctttcc cttggtgccc    1560 tcctttttt tttatcctag tcattcttcc ctaatcttcc acttgagtgt caagctgacc    1620
ttgctgatgg tgacattgca cctggatgta ctatccaatc tgtgatgaca ttccctgcta    1680
ataaaagaca acataactca                                               1700
```

<210> SEQ ID NO 2
<211> LENGTH: 206
<212> TYPE: PRT
<213> ORGANISM: Homo sapiens

<400> SEQUENCE: 2

```
Met Asn Phe Gln Gln Arg Leu Gln Ser Leu Trp Thr Leu Ala Arg Pro
 1               5                  10                  15

Phe Cys Pro Pro Leu Leu Ala Thr Ala Ser Gln Met Gln Met Val Val
                20                  25                  30

Leu Pro Cys Leu Gly Phe Thr Leu Leu Leu Trp Ser Gln Val Ser Gly
            35                  40                  45

Ala Gln Gly Gln Glu Phe His Phe Gly Pro Cys Gln Val Lys Gly Val
        50                  55                  60

Val Pro Gln Lys Leu Trp Glu Ala Phe Trp Ala Val Lys Asp Thr Met
 65                  70                  75                  80

Gln Ala Gln Asp Asn Ile Thr Ser Ala Arg Leu Leu Gln Gln Glu Val
                85                  90                  95

Leu Gln Asn Val Ser Asp Ala Glu Ser Cys Tyr Leu Val His Thr Leu
            100                 105                 110

Leu Glu Phe Tyr Leu Lys Thr Val Phe Lys Asn Tyr His Asn Arg Thr
        115                 120                 125

Val Glu Val Arg Thr Leu Lys Ser Phe Ser Thr Leu Ala Asn Asn Phe
130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
                165                 170                 175

Phe Lys Gln Leu Asp Val Glu Ala Ala Leu Thr Lys Ala Leu Gly Glu
            180                 185                 190

Val Asp Ile Leu Leu Thr Trp Met Gln Lys Phe Tyr Lys Leu
        195                 200                 205
```

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: (0)...(0)
<223> OTHER INFORMATION: primer for mda-7

<400> SEQUENCE: 3

-continued

```
atgctctgtc cctgcagata                                                    20

<210> SEQ ID NO 4
<211> LENGTH: 20
<212> TYPE: DNA
<213> ORGANISM: Homo sapiens
<220> FEATURE:
<221> NAME/KEY: misc_feature
<222> LOCATION: (0)...(0)
<223> OTHER INFORMATION: primer for MDA-7

<400> SEQUENCE: 4
ctctggatgc tgtgaagagt                                                    20

<210> SEQ ID NO 5
<211> LENGTH: 12
<212> TYPE: PRT
<213> ORGANISM: Homo sapiens
<220> FEATURE:
<223> OTHER INFORMATION: 153-164 of human MDA-7

<400> SEQUENCE: 5

Pro Ser Gln Glu Asn Glu Met Phe Ser Ile Arg Asp
 1               5                  10

<210> SEQ ID NO 6
<211> LENGTH: 5775
<212> TYPE: DNA
<213> ORGANISM: Homo sapiens
<220> FEATURE:
<221> NAME/KEY: misc_feature
<222> LOCATION: (193)...(759)
<223> OTHER INFORMATION: CDS = 193-759

<400> SEQUENCE: 6
tcctaggcgg cggccgcggc ggcggaggca gcagcggcgg cggcagtggc ggcggcgaag        60
gtggcggcgg ctcggccagt actcccggcc cccgccattt cggactggga gcgagcgcgg      120
cgcaggcact gaaggcggcg gcggggccag aggctcagcg gctcccaggt gcggagagag      180
ggcctgctga aaatgactga atataaactt gtggtagttg gagcttgtgg cgtaggcaag      240
agtgccttga cgatacagct aattcagaat cattttgtgg acgaatatga tccaacaata      300
gaggattcct acaggaagca agtagtaatt gatgtgagaaa cctgtctctt ggatattctc      360
gacacagcag gtcaagagga gtacagtgca atgagggacc agtacatgag gactggggag      420
ggctttcttt gtgtatttgc cataaataat actaaatcat ttgaagatat tcaccattat      480
agagaacaaa ttaaaagagt taaggactct gaagatgtac ctatggtcct agtaggaaat      540
aaatgtgatt tgccttctag aacagtagac acaaaacagg ctcaggactt agcaagaagt      600
tatggaattc cttttattga acatcagca aagacaagac agggtgttga tgatgccttc      660
tatacattag ttcgagaaat tcgaaaacat aaagaaaaga tgagcaaaga tggtaaaaag      720
aagaaaaaga agtcaaagac aaagtgtgta attatgtaaa tacaatttgt acttttttct      780
taaggcatac tagtacaagt ggtaattttt gtacattaca ctaaattatt agcatttgtt      840
ttagcattac ctaattttt tcctgctcca tgcagactgt tagcttttac cttaaatgct      900 tatttttaaaa tgacagtgga agtttttttt cctcgaagt gccagtattc ccagagtttt      960 ggttttttgaa ctagcaatgc ctgtgaaaaa gaaactgaat acctaagatt tctgtcttgg     1020 ggttttttggt gcatgcagtt gattacttct tattttttctt accaagtgtg aatgttggtg     1080
tgaaacaaat taatgaagct tttgaatcat ccctattctg tgttttatct agtcacataa     1140
```

-continued

```
atggattaat tactaatttc agttgagacc ttctaattgg ttttttactga aacattgagg    1200 gacacaaatt tatgggcttc ctgatgatga ttcttctagg catcatgtcc tatagtttgt    1260
catccctgat gaatgtaaag ttacactgtt cacaaaggtt ttgtctcctt tccactgcta    1320
ttagtcatgg tcactctccc caaaatatta tattttttct ataaaagaa aaaaatggaa    1380 aaaaattaca aggcaatgga aactattata aggccatttc cttttcacat tagataaatt    1440
actataaaga ctcctaatag cttttttcctg ttaaggcaga cccagtatga atgggattat    1500
tatagcaacc attttggggc tatatttaca tgctactaaa ttttttataat aattgaaaag    1560 attttaacaa gtataaaaaa attctcatag gaattaaatg tagtctccct gtgtcagact    1620
gctctttcat agtataactt taaatctttt cttcaacttg agtctttgaa gatagtttta    1680
attctgcttg tgacattaaa agattatttg ggccagttat agcttattag gtgttgaaga    1740
gaccaaggtt gcaagccagg ccctgtgtga accttgagct ttcatagaga gtttcacagc    1800
atggactgtg tgccccacgg tcatccgagt ggttgtacga tgcattggtt agtcaaaaat    1860
ggggagggac tagggcagtt tggatagctc aacaagatac aatctcactc tgtggtggtc    1920
ctgctgacaa atcaagagca ttgcttttgt ttcttaagaa aacaaactct tttttaaaaa    1980
ttacttttaa atattaactc aaaagttgag attttgggt ggtggtgtgc caagacatta    2040
attttttttt taaacaatga agtgaaaaag ttttacaatc tctaggtttg gctagttctc    2100
ttaacactgg ttaaattaac attgcataaa cacttttcaa gtctgatcca tatttaataa    2160
tgctttaaaa taaaaataaa aacaatcctt ttgataaatt taaaatgtta cttatttttaa    2220 aataaatgaa gtgagatggc atggtgaggt gaaagtatca ctggactagg ttgttggtga    2280
cttaggttct agataggtgt cttttaggac tctgattttg aggacatcac ttactatcca    2340
tttcttcatg ttaaaagaag tcatctcaaa ctcttagttt tttttttttta cactatgtga    2400 tttatattcc atttacataa ggatacactt atttgtcaag ctcagcacaa tctgtaaatt    2460
tttaacctat gttacaccat cttcagtgcc agtcttgggc aaaattgtgc aagaggtgaa    2520
gtttatattt gaatatccat tctcgtttta ggactcttct tccatattag tgtcatcttg    2580
cctccctacc ttccacatgc cccatgactt gatgcagttt taatacttgt aattcccta    2640 accataagat ttactgctgc tgtggatatc tccatgaagt tttcccactg agtcacatca    2700
gaaatgccct acatcttatt ttcctcaggg ctcaagagaa tctgacagat accataaagg    2760
gatttgacct aatcactaat tttcaggtgg tggctgatgc tttgaacatc tctttgctgc    2820
ccaatccatt agcgacagta ggatttttca accctggtat gaatagacag aaccctatcc    2880
agtggaagga gaatttaata aagatagtgc agaaagaatt ccttaggtaa tctataacta    2940
ggactactcc tggtaacagt aatacattcc attgttttag taaccagaaa tcttcatgca    3000
atgaaaaata ctttaattca tgaagcttac tttttttttt ttggtgtcag agtctcgctc    3060
ttgtcaccca ggctggaatg cagtggcgcc atctcagctc actgcaacct tccatcttcc    3120
caggttcaag cgattctcgt gcctcggcct cctgagtagc tgggattaca ggcgtgtgca    3180
ctacactcaa ctaattttttg tattttttagg agagacgggg tttcacctgt tggccaggct    3240
ggtctcgaac tcctgacctc aagtgattca cccaccttgg cctcataaac ctgttttgca    3300
gaactcattt attcagcaaa tatttattga gtgcctacca gatgccagtc accgcacaag    3360
gcactgggta tatggtatcc ccaaacaaga gacataatcc cggtccttag gtactgctag    3420
tgtggtctgt aaatatcttac taaggccttt ggtatacgac ccagagataa cacgatgcgt    3480
```

```
attttagttt tgcaaagaag gggtttggtc tctgtgccag ctctataatt gttttgctac    3540
gattccactg aaactcttcg atcaagctac tttatgtaaa tcacttcatt gttttaaagg    3600
aataaacttg attatattgt tttttattt ggcataactg tgattctttt aggacaatta    3660
ctgtacacat taaggtgtat gtcagatatt catattgacc caaatgtgta atattccagt    3720
tttctctgca taagtaatta aaatatactt aaaaattaat agttttatct gggtacaaat    3780
aaacagtgcc tgaactagtt cacagacaag ggaaacttct atgtaaaaat cactatgatt    3840
tctgaattgc tatgtgaaac tacagatctt tggaacactg tttaggtagg gtgttaagac    3900
ttgacacagt acctcgtttc tacacagaga aagaaatggc catacttcag gaactgcagt    3960
gcttatgagg ggatatttag gcctcttgaa ttttttgatgt agatgggcat ttttttaagg    4020
tagtggttaa ttacctttat gtgaactttg aatggtttaa caaagatttt gttttttgtag    4080 agattttaaa ggggagaat tctagaaata aatgttacct aattattaca gccttaaaga     4140
caaaaatcct tgttgaagtt tttttaaaaa aagactaaat tacatagact taggcattaa    4200
catgtttgtg gaagaatata gcagacgtat attgtatcat ttgagtgaat gttcccaagt    4260
aggcattcta ggctctattt aactgagtca cactgcatag gaatttagaa cctaactttt    4320
ataggttatc aaaactgttg tcaccattgc acaatttgt cctaatatat acatagaaac      4380 tttgtgggc atgttaagtt acagtttgca caagttcatc tcatttgtat tccattgatt     4440 ttttttttc ttctaaacat tttttcttca aaacagtata tataactttt tttaggggat     4500
tttttttaga cagcaaaaaa ctatctgaag atttccattt gtcaaaaagt aatgatttct    4560
tgataattgt gtagtgaatg ttttttagaa cccagcagtt accttgaaag ctgaatttat    4620
atttagtaac ttctgtgtta atactggata gcatgaattc tgcattgaga aactgaatag    4680
ctgtcataaa atgctttctt tcctaaagaa agatactcac atgagttctt gaagaatagt    4740
cataactaga ttaagatctg tgttttagtt taatagtttg aagtgcctgt ttgggataat    4800
gataggtaat ttagatgaat ttaggggaaa aaaaagttat ctgcagttat gttgagggcc    4860
catctctccc cccacacccc cacagagcta actgggttac agtgttttat ccgaaagttt    4920
ccaattccac tgtcttgtgt tttcatgttg aaaatacttt tgcatttttc ctttgagtgc    4980
caatttctta ctagtactat ttcttaatgt aacatgttta cctggcctgt cttttaacta    5040
tttttgtata gtgtaaactg aaacatgcac attttgtaca ttgtgctttc ttttgtgggt    5100
catatgcagt gtgatccagt tgtttttccat catttggttg cgctgaccta ggaatgttgg    5160
tcatatcaaa cattaaaaat gaccactctt ttaatgaaat taacttttaa atgtttatag    5220
gagtatgtgc tgtgaagtga tctaaaattt gtaatatttt tgtcatgaac tgtactactc    5280
ctaattattg taatgtaata aaaatagtta cagtgactat gagtgtgtat ttattcatgc    5340
aaatttgaac tgtttgcccc gaaatggata tggatacttt ataagccata gacactatag    5400
tataccagtg aatctttat gcagcttgtt agaagtatcc ttttattttc taaaaggtgc     5460
tgtggatatt atgtaaaggc gtgtttgctt aaacaatttt ccatatttag aagtagatgc    5520
aaaacaaatc tgcctttatg acaaaaaaat aggataacaa tatttattta tttccttta     5580 tcaataaggt aattgataca caacaggtga cttggtttta ggcccaaagg tagcagcagc    5640
aacattaata atggaaataa ttgaatagtt agttatgtat gttaatgcca gtcaccagca    5700
ggctatttca aggtcagaag taatgactcc atacatatta tttatttcta taactacatt    5760
taaatcatta ccagg                                                     5775
```

```
<210> SEQ ID NO 7
<211> LENGTH: 188
<212> TYPE: PRT
<213> ORGANISM: Homo sapiens

<400> SEQUENCE: 7

Met Thr Glu Tyr Lys Leu Val Val Gly Ala Cys Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
                35                  40                  45

Glu Thr Cys Leu Leu Asp Ile Leu Asp Thr Ala Gly Gln Glu Glu Tyr
         50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                    85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
            130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                    165                 170                 175

Lys Lys Lys Lys Ser Lys Thr Lys Cys Val Ile Met
                180                 185

<210> SEQ ID NO 8
<211> LENGTH: 188
<212> TYPE: PRT
<213> ORGANISM: Homo sapiens
<220> FEATURE:
<221> NAME/KEY: unknown
<222> LOCATION: 12
<223> OTHER INFORMATION: Xaa = any amino acid

<400> SEQUENCE: 8

Met Thr Glu Tyr Lys Leu Val Val Gly Ala Xaa Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
                35                  40                  45

Glu Thr Cys Leu Leu Asp Ile Leu Asp Thr Ala Gly Gln Glu Glu Tyr
         50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                    85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125
```

```
Gln Ala Gln Asp Leu Ala Arg Ser Tyr Gly Ile Pro Phe Ile Glu Thr
            130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 9
<211> LENGTH: 188
<212> TYPE: PRT
<213> ORGANISM: Homo sapiens
<220> FEATURE:
<221> NAME/KEY: unknown
<222> LOCATION: 13
<223> OTHER INFORMATION: Xaa = any amino acid

<400> SEQUENCE: 9

Met Thr Glu Tyr Lys Leu Val Val Val Gly Ala Cys Xaa Val Gly Lys
  1               5                  10                  15

Ser Ala Leu Thr Ile Gln Leu Ile Gln Asn His Phe Val Asp Glu Tyr
             20                  25                  30

Asp Pro Thr Ile Glu Asp Ser Tyr Arg Lys Gln Val Ile Asp Gly
             35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
            130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 10
<211> LENGTH: 188
<212> TYPE: PRT
<213> ORGANISM: Homo sapiens
<220> FEATURE:
<221> NAME/KEY: unknown
<222> LOCATION: 18
<223> OTHER INFORMATION: Xaa = any amino acid

<400> SEQUENCE: 10

Met Thr Glu Tyr Lys Leu Val Val Val Gly Ala Cys Gly Val Gly Lys
  1               5                  10                  15
```

```
Ser Xaa Leu Thr Ile Gln Leu Ile Gln Asn His Phe Val Asp Glu Tyr
        20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
 50                      55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185

<210> SEQ ID NO 11
<211> LENGTH: 188
<212> TYPE: PRT
<213> ORGANISM: Homo sapiens
<220> FEATURE:
<221> NAME/KEY: unknown
<222> LOCATION: 61
<223> OTHER INFORMATION: Xaa = any amino acid

<400> SEQUENCE: 11

Met Thr Glu Tyr Lys Leu Val Val Val Gly Ala Cys Gly Val Gly Lys
 1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Xaa Glu Glu Tyr
 50                      55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140
```

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 12
<211> LENGTH: 17
<212> TYPE: DNA
<213> ORGANISM: Artificial Sequence
<220> FEATURE:
<223> OTHER INFORMATION: artificial human K-ras antisense
      oligonucleotide with phosphorothioate linkages

<400> SEQUENCE: 12
ctacgccaac agctcca                                                  17

<210> SEQ ID NO 13
<211> LENGTH: 17
<212> TYPE: DNA
<213> ORGANISM: Artificial Sequence
<220> FEATURE:
<223> OTHER INFORMATION: artificial human K-ras antisense
      oligonucleotide with phosphorothioate linkages

<400> SEQUENCE: 13
ctacgccacg agctcca                                                  17

<210> SEQ ID NO 14
<211> LENGTH: 17
<212> TYPE: DNA
<213> ORGANISM: Artificial Sequence
<220> FEATURE:
<223> OTHER INFORMATION: artificial human K-ras antisense
      oligonucleotide with phosphorothioate linkages

<400> SEQUENCE: 14
ctacgccatc agctcca                                                  17

<210> SEQ ID NO 15
<211> LENGTH: 18
<212> TYPE: DNA
<213> ORGANISM: Artificial Sequence
<220> FEATURE:
<223> OTHER INFORMATION: artificial antisense K-ras artificial
      oligonucleotide, with phosphorothioate linkages

<400> SEQUENCE: 15
cacaagttta tattcagt                                                 18

<210> SEQ ID NO 16
<211> LENGTH: 18
<212> TYPE: DNA
<213> ORGANISM: Artificial Sequence
<220> FEATURE:
<223> OTHER INFORMATION: artificial mismatched antisense K-ras
      artificial oligonucleotide

<400> SEQUENCE: 16
cacttgcaaa tattcagt                                                 18

<210> SEQ ID NO 17
<211> LENGTH: 18
<212> TYPE: DNA

-continued

```
<213> ORGANISM: Artificial Sequence
<220> FEATURE:
<223> OTHER INFORMATION: artificial scrambled antisense artificial
      oligonucleotide

<400> SEQUENCE: 17
actagctata ctagctat                                                  18
```

COMBINATORIAL METHODS FOR INDUCING CANCER CELL DEATH

CROSS REFERENCE TO RELATED APPLICATIONS

This application is a continuation of International Patent Application Ser. No. PCT/US02/26454, filed Aug. 19, 2002, and published in English as WO03/016499 on Feb. 27, 2003, which claims priority as a continuation-in-part of U.S. patent application Ser. No. 09/933,115, filed Aug. 20, 2001, the contents of which are incorporated by reference herein in their entireties.

The subject matter described herein was supported in part by National Institutes of Health Grants CA35675, CA37670, CA74468 and DK52825, and Department of Defense Grant BC98-0148, so that the United States Government has certain rights herein.

1. INTRODUCTION

The present invention relates to methods and compositions for inhibiting proliferation and inducing cell death in a population of cancer cells by (i) increasing the amount of the differentiation associated protein MDA-7, and (ii) decreasing RAS activity within the population. It is based, at least in part, on the discovery that decreasing expression of a mutated, activated K-ras gene, together with introducing an expressible mda-7 gene, in pancreatic cancer cells had a synergistic growth-inhibitory and anti-survival effect, and abolished tumorigenicity of the cells in athymic nude mice. The invention provides for methods of treating patients suffering from pancreatic cancer or other malignancies.

2. BACKGROUND OF THE INVENTION

2.1. Pancreatic Cancer

Pancreatic cancer is the eighth most frequent type of solid tumor arising worldwide, but, as a consequence of the current lack of effective therapy, it is the fourth most frequent cause of cancer death (Gunzburg and Salmons, 2001, Trends Mol. Med. 7(1):30-37). It is estimated that 29,200 cases will be diagnosed in the United States in 2001, and 28,900 of these patients are expected to die (Cancer Facts and Figures, 2001. Atlanta, Ga.; American Cancer Society, 2001). Long-term survival for patients with organ-confined disease is only 20 percent, and in the majority of cases, in which the disease, when diagnosed, has already spread past the pancreas, survival is only 4 percent (Hilgers and Kern, 1999, Genes, Chromosomes & Cancer 26:1-12; Regine et al., 1998, Front. Biosci. 3: E186-E192; Blaszkowsky, 1998, Front. Biosci. 3:E214-E225; Lorenz et al., 2000, Eur. J. Cancer 36:957-965; Rosenberg, 2000, Drugs 59:1071-1089).

The poor prognosis associated with pancreatic cancer has been attributed to a number of factors. These include (1) the anatomic location of the pancreas and lack of specific early symptoms make early diagnosis difficult; (2) the tumor spreads rapidly to surrounding vital organs; (3) even small tumors tend to metastasize; and (4) the cancer generally responds poorly to standard therapeutic measures (Aold et al., 1995, Cancer Res. 55:3810-3816, citing Yamaguchi et al., 1989, Jpn. J. Clin. Oncol. 19:14-22; Warshaw and Castillo, 1992, N. Engl. J. Med. 326:455-465; Cohn, 1989, Int. J. Pancreatol. 7:1-11; Ozaki et al., 1992, Int. J. Pancreatol. 12:5-9; Arbuck, 1990, Int. J. Pancreatol. 7:209-222).

The lethality of pancreatic cancer has warranted extreme therapeutic measures. A recent study suggests that multimodal therapy, combining pancreaticoduodenectomy with postoperative adjuvant chemotherapy (using fluorouracil) and external beam radiation therapy maximizes local tumor control and improves the length of survival (Evans et al., 2001, Oncology (Huntingt) 15(6):727-737). When the tumor has been unresectable, combination chemotherapy with gemcitabine and docetaxel has achieved modest success in decreasing tumor mass and or/serum tumor markers (Sherman and Fine, 2001, Oncology 60(4):316-321).

2.2. The Molecular Biology of Pancreatic Cancer

To better treat this aggressive tumor, scientists are attempting to achieve an understanding of pancreatic cancer at the molecular level. A number of molecules and pathways have been implicated as either playing an etiologic role or creating therapeutic opportunities, including: fibroblast growth factors, as modulators of the E-cadherin/catenin system (Hariry et al., 2001, Br. J. Cancer 84(12):1656-1663); the 26S proteasome (Shah et al., 2001, J. Cell. Biochem. 82(1):110-122); cyclic adenosine monophosphate (cAMP), acting with other second messengers to mediate signals from tumoral growth hormone releasing hormone receptors (Rekasi et al., 2001, Peptides 22(6):879-886); the CD95 (FAS-Apo-1) apoptosis pathway, which is reported to be potentially functional, but blocked by an unknown protein in pancreatic cancer cells (Glazyrin et al., 2001, Pancreas 22(4):357-365); P38 MAP kinase, as a negative regulator of MEK/ERK-mediated proliferation (Ding and Adrian, 2001, Biochem. Biophys. Res. Commun. 282(2): 447-453), and transforming growth factor beta 1 ("TGF-β1"; Giehl et al., 2000, Oncogene 19(39):4531-4541; Hashimoto et al., 2001, Pancreas 22(4 :341-347; Ellenrieder et al., 2001, Int. J. Cancer 93(2):204-211).

In pancreatic tumors, a high incidence of overexpression of TGF-βs and their receptors, as well as activating mutations of the K-ras oncogene, have been reported, suggesting that "interactions of the RAS cascade and the TGF-β pathway may play an important role in pancreatic carcinogenesis" (Ellenrieder et al., 2001, Cancer Res. 61:4222-4228). In experiments to test this hypothesis, TGF-β1 treatment of responsive pancreatic cancer cells having activating K-ras mutations resulted in an epithelial-mesenchymal transdifferentiation and a more invasive phenotype which could be reduced or abolished by pretreatment with a MEK1 inhibitor (Id.).

Multiple subsets of genes have been observed to undergo genetic change, either activation or inactivation, during tumor development and progression (Hilgers and Kern, 1999, Genes, Chromosomes & Cancer 26:1-12; Perugini et al., 1998, Crit. Rev. Eukaryotic Gene Express. 8:377-393; Friess et al., 1999, Dig. Surg. 16:281-290). Frequent genetic modification in pancreatic carcinomas include activation of the K-ras oncogene (85 to 95 percent) and inactivation of the p16/RB1 (>90 percent), p53 (75 percent) and DPC4 (55 percent) tumor suppressor genes (Id.). These findings highlight the complexity of pancreatic cancer and may provide a partial explanation for the aggressiveness and inherent resistance of this neoplasm to conventional therapies such as chemotherapy and radiation (Regine et al., 1998, Front. Biosci. 3:E186-E192; Blaszkowsky, 1998, Front. Biosci. 3:E214-E225; Lorenz et al., 2000, Eur. J. Cancer 36:957-965; Rosenberg, 2000, Drugs 59:1071-1089).

2.3. RAS Proteins

Of the genetic changes that occur in pancreatic cancers, mutations in the K-ras gene, predominantly in codon 12, are the most frequent (Hilgers and Kern, 1999, Genes, Chromosomes & Cancer 26:1-12; Almoguera et al., 1988, Cell 53:549-554; Longnecker and Terhune, 1998, Pancreas 17:323-324). RAS proteins constitute a family of eukaryotic cellular proteins that act to assist in the transmission of information from the outside of the cell to the inside, resulting in changes in the fundamental properties of the cell, such as levels of gene transcription and expression, growth status and differentiation state (Campbell et al., 1998, Oncogene 17:1395-1341; Kolch, 2000, Biochem. J. 351:289-305). As such, RAS proteins can play an important role in the transformation of a cell to a cancer cell, a process referred to as "oncogenesis". The ras family contains three functional so-called "oncogenes", namely H-ras, K-ras, and N-ras, which encode highly similar proteins with molecular weights of 21,000 daltons (Reuther and Der, 2000, Curr. Opin. Cell Biol. 12:157-165; note that the proteins and genes of this family are referred to herein by upper case and lower case italics, respectively, for consistency within this document (see below) but contrary to popular convention).

Functionally, a RAS protein alternates between two forms in the cell. When unattached to the cell membrane and bound to the compound GDP (guanine diphosphate), the RAS protein is in its biologically inactive state. For RAS to become active, several events must occur. First, the protein must be chemically modified by a process called farnesylation. This modification attaches a fatty acid side chain onto the RAS protein, enhancing its ability to associate with the lipid-rich inner cell membrane. Once anchored to the cell membrane, RAS can then interact with several other proteins to complete its activation. These include membrane-spanning protein receptors that bind informational molecules that are presented on the outside of the cell membrane, and a variety of accessory molecules that mediate the interaction between RAS and the receptor protein. These latter molecules, so-called exchange and adapter proteins, also assist in the release of GDP from the RAS protein and the binding of GTP (guanine triphosphate), which is the final step in activation.

Activation of the wild-type RAS proteins is a reversible process. RAS itself is also a GTPase, that is, it hydrolyzes GTP to form GDP. The rate of this conversion, which is greatly enhanced by other cellular proteins known as GTPase-activating proteins (GAPs), is the key factor that determines how long the RAS-mediated signal persists in the cell. Once activated, RAS triggers a cascade of signals that are conveyed from the cell membrane into the nucleus of the cell. A diagram depicting a simplified version of the RAS pathway is presented in FIG. 1. These signals are mediated by a series of kinases, enzymes that catalyze the phosphorylation of cellular proteins. Ultimately, this pathway results in the activation of nuclear proteins called transcription factors, which act to increase the rate of transcription of specific genes within the cell. When activated, K-RAS can signal into the cytosol via multiple downstream signaling pathways such as the classical MAPK pathway, the phosphatidylinositol ("PI3") kinase pathway, and the JNK pathway, to induce a plethora of cellular changes, including enhanced proliferation and cell survival (Dent et al., 1992, Science 257:1404-1407; Gire et al., 2000, Oncogene 19:2269-2276; Almeida et al., 2000, J. Cell Biol. 149:741-754).

Many of the genes whose transcription are upregulated by RAS activation are involved in the control of cell cycling, and thus persistent activation of RAS, which can be caused by mutations in the ras gene which impair the protein's GTPase activity, can lead to abnormalities in cellular proliferation. In fact, this mechanism has been implicated in the development of a wide variety of human cancers. A common occurrence in pancreatic and other cancers involves point mutations of K-ras, which may involve codon 12 (a common mutation in pancreatic cancer cells) and codons 13 and 61 (more common in other cancers) (Hilgers and Kern, 1999, Genes, Chromosomes & Cancer 26:1-12; Almoguera et al., 1988, Cell 53:549-554; Longnecker and Terhune, 1998, Pancreas 17:323-324). For example, Noda et al. (2001, Oncol. Rep. 8(4):889-92) report mutations at codons 12, 13 and 61 of K-ras in non-small cell lung cancer tumors. Demunter et al. (2001, Cancer Res. 61:4916-4922) report a novel mutation in codon 18 of exon 1 of the N-ras gene which was found in 15 percent of primary malignant melanoma tumors studied but not in any metastatic melanoma. Other cancers associated with point mutations of ras include gallbladder carcinoma (Kim et al., 2001, Cancer Lett. 169 (1):59-68) and colon carcinoma (Clarke et al., 2001, Int. J. Colorectal Dis. 16(2):108-111).

In view of the association between ras mutation and cancer, a number of researchers have attempted to reverse oncogenesis in cells by selectively inhibiting the mutated ras gene. For example, interference in expression of K-ras using antisense RNA (Aoki et al., 1995, Cancer Res. 55:3810-3816; Aoki et al., 1997, Mol. Carcinogen. 20:251-258) or with K-ras mutation-specific phosphorothioate oligodeoxynucleotides (Kita et al., 1999, Intl. J. Cancer 80:553-558) has been observed to inhibit the growth of pancreatic cancer cells containing K-ras mutations, but not pancreatic carcinoma cells containing a non-mutated wild-type K-ras gene. The dominant negative H-ras mutant, N116Y, was found to suppress pancreatic cancer cell growth in vitro and in vivo, including tumorigenesis and metastasis to the liver of nude mice (Shichionohe et al., 1996, J. Surg. Res. 142:63-71; Takeuchi et al., 2000, Gene Ther. 7:518-526). Although promising, these studies demonstrated that a single approach of inhibiting K-ras is not sufficient to completely eradicate pancreatic carcinoma cells (Aoki et al., 1995, Cancer Res. 55:3810-3816; Aoki et al., 1997, Mol. Carcinogen. 20:251-258; Kita et al., 1999, Intl. J. Cancer 80:553-558; Shichionohe et al., 1996, J. Surg. Res. 142:63-71).

2.4. MDA-7

A critical element of the present invention, the mda-7 gene (named as a melanoma differentiation ssociated gene), was previously found ineffective in modifying the malignant properties of pancreatic cancer cells. Mda-7 was identified by a subtractive hybridization technique using cDNA libraries prepared from actively proliferating melanoma cells and from melanoma cells which had been induced to terminally differentiate by treatment with recombinant human fibroblast interferon (IFN-β) and the protein kinase C activator mezerein (Jiang and Fisher, 1993, Mol. Cell. Different. 1:285-299; Jiang et al., 1995, Oncogene 11:2477-2486). MDA-7 has been characterized as a protein having 206 amino acids with a size of 23.8 kDa and a sequence as set forth in SEQ ID NO:1 (Genbank Accession Number U16261; Jiang et al., 1995, Oncogene 11:2477-2486).

When the mda-7 gene was introduced into a wide spectrum of human cancers, growth of cancer cells was inhibited (U.S. Pat. No. 5,710,137 by Fisher, issued Jan. 20, 1998;

Jiang et al., 1996, Proc. Natl. Acad. Sci. U.S.A. 93:9160-9165; Su et al., 1998, Proc. Natl. Acad. Sci. U.S.A. 95:14400-14405; Madireddi et al., 2000, Adv. Exptl. Med. Biol. 465:239-261). MDA-7 has been observed to suppress growth in cancer cells which either do not express, or which contain defects in, both retinoblastoma ("rb") and p53 tumnor suppressor genes, indicating that mda-7 mediated growth inhibition does not depend on these elements (Jiang et al., 1996, Proc. Natl. Acad. Sci. U.S.A. 93:9160-9165). In contrast to the anti-proliferative effect on various cancer cells, no significant growth inhibitory effect was apparent when this gene was introduced into normal human fibroblast or epithelial cells (Jiang et al., 1996, Proc. Natl. Acad. Sci. U.S.A. 93:9160-9165; Madireddi et al., 2000, Adv. Exptl. Med. Biol. 465:239-261; Saeki et al., 2000, Gene Ther. 7:2051-2057; Mhashilkar et al., 2001, Mol. Med. 7:271-282).

Despite its inhibitory effects on a variety of tumors, mda-7 was not found to be effective against pancreatic carcinoma cells. The present invention is based on the discovery that although neither introduction of an mda-7 gene nor inhibition of RAS have been observed to effectively control pancreatic cancer cell growth, their combination produces a synergistic effect, resulting in a dramatic suppression in cell growth and decrease in cell viability. The potency of mda-7/anti-RAS against a cancer as aggressive and rapidly lethal as pancreatic cancer is unexpected in view of the lack of effectiveness of either agent, used alone. In addition, the fact that RAS inhibition appears to be required for MDA-7 to be effective is surprising in view of the fact that MDA-7 has been observed to exert an anti-proliferative effect in the context of increased RAS activity; introduction of an mda-7 gene had a strong anti-proliferative effect on rat embryo fibroblasts transformed with the H-ras oncogene (Jiang et al., 1996, Proc. Natl. Acad. Sci. U.S.A. 93:9160-9165).

3. SUMMARY OF THE INVENTION

The present invention relates to methods and compositions for inhibiting proliferation and inducing cell death in a population of cancer cells by (i) increasing the amount of the differentiation associated protein, MDA-7 and (ii) decreasing RAS activity within the population. RAS activity may be decreased by agents directed at RAS itself or at molecules upstream or downstream of RAS in the RAS pathway such as, for example, the epidermal growth factor receptor ("EGFR"), RAF, MAPK kinase, MAPK and PI3 kinase. In preferred embodiments, the methods include (i) increasing the amount of MDA-7 protein and (ii) decreasing the expression of an activated ras gene in a cancer cell. These methods and compositions may be directed toward the treatment of subjects suffering from cancer, particularly pancreatic cancer.

The invention is based, at least in part, on the discovery that apoptosis of pancreatic cancer cells having activating mutations in K-ras could be induced by introducing an MDA-7-encoding nucleic acid and by inhibiting K-RAS expression. In particular, it was found that introduction, into the pancreatic cancer cells, of antisense nucleic acids targeted at K-ras, together with a replication defective adenovirus carrying the mda-7 gene, not only induced apoptosis, but also inhibited malignant cell colony formation in vitro and tumor formation in vivo in nude mice.

Accordingly, the present invention provides for methods of inhibiting the proliferation and/or decreasing the viability of cancer cells, particularly pancreatic cancer cells, which carry an activated ras gene, and for therapeutic regimens which utilize such methods. Methods are provided for determining whether a particular cancer cell is likely to be responsive to the methods of the invention.

The present invention further provides for compositions which may be used to increase expression of MDA-7 and/or decrease RAS activity. In one specific, non-limiting embodiment, the present invention provides for an adenovirus vector comprising a sequence encoding mda-7 and a sequence encoding antisense ras, in expressible form.

In additional aspects of the invention, it has been discovered that the culture supernatant of cells expressing MDA-7 has an antiproliferative effect on pancreatic cancer cells when co-administered with antisense ras molecules. Accordingly, the present invention provides for methods for inhibiting cancer cell proliferation comprising exposing cancer cells to extracellular MDA-7.

4. DESCRIPTION OF THE FIGURES

FIG. 1. Simplified diagram of the RAS pathway.

Figure 2A:
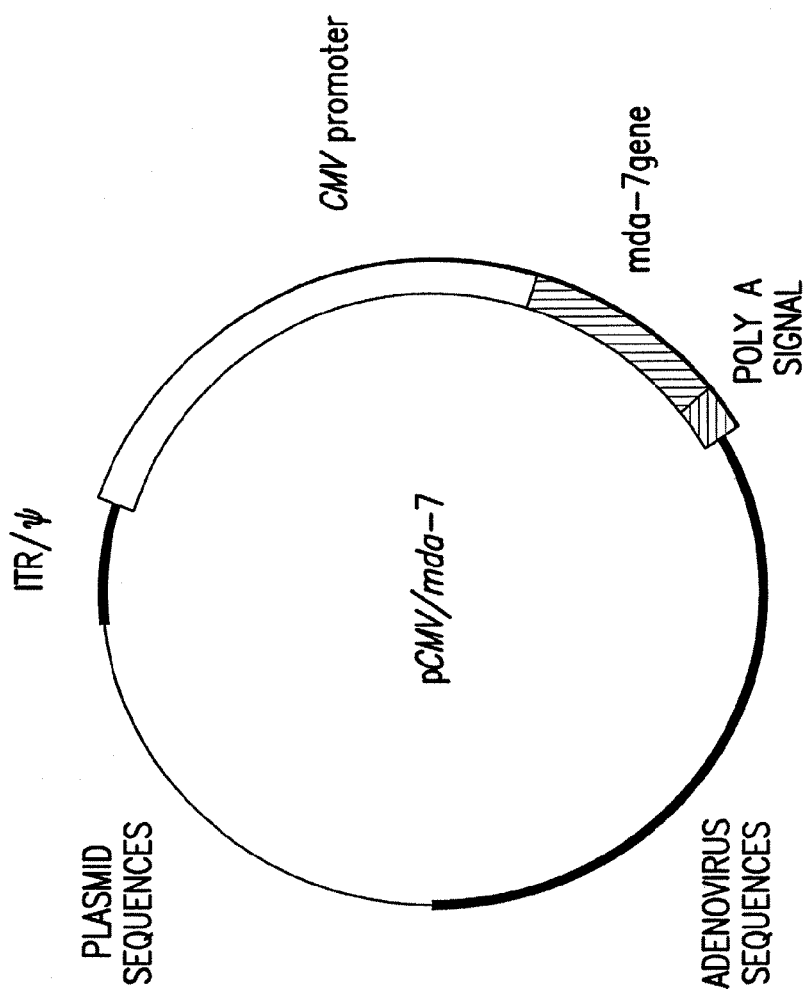
Figure 2B:
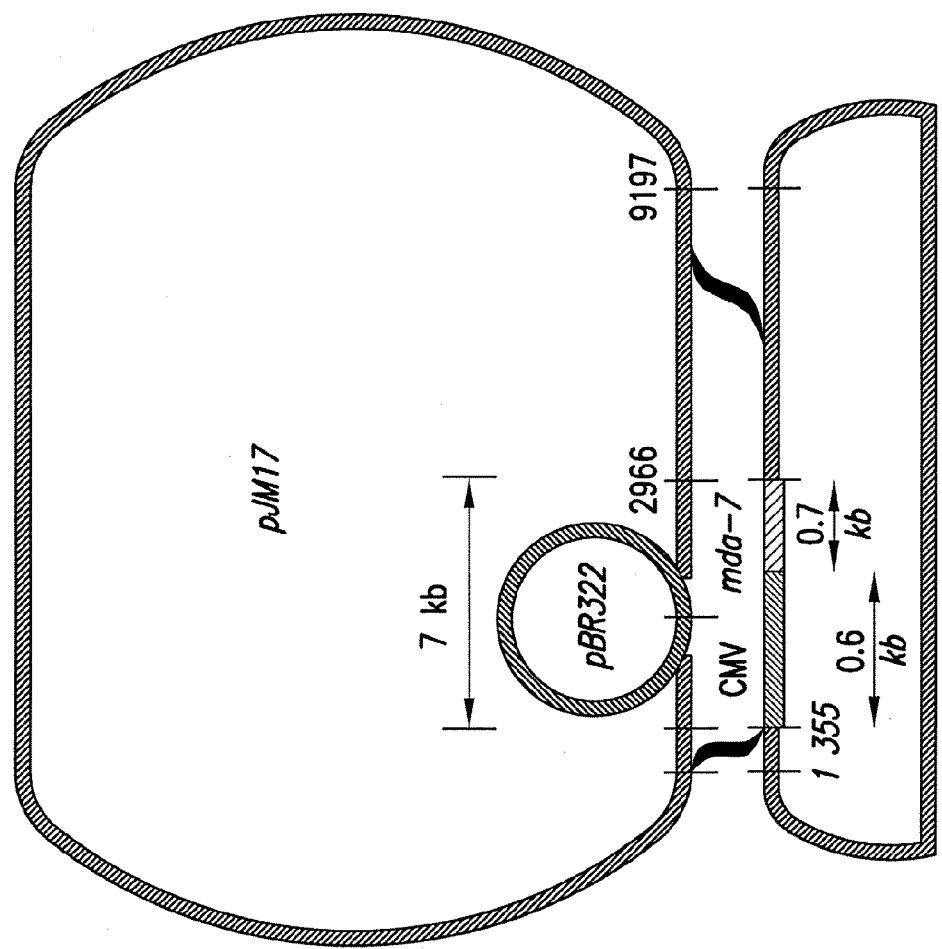
Figure 2C:
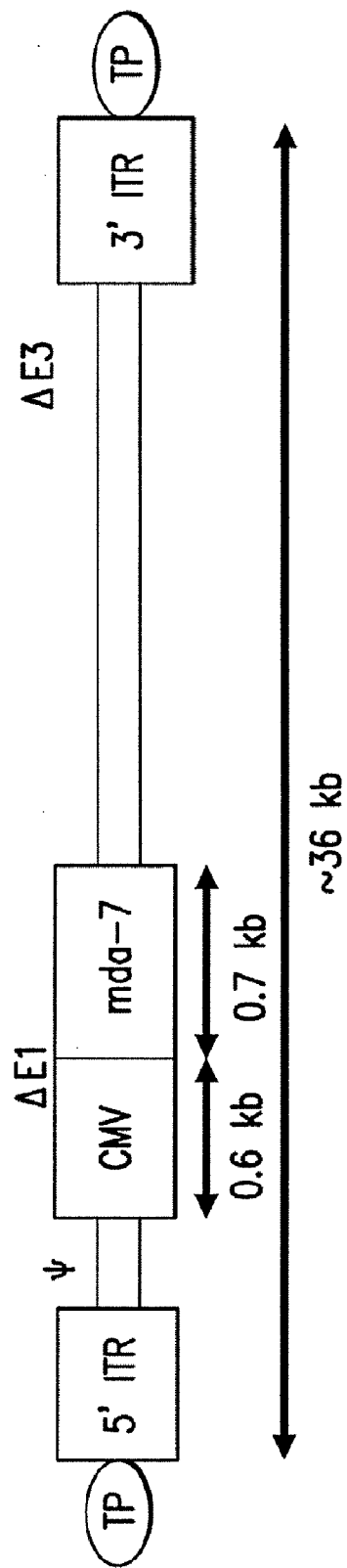

FIGS. 2A-C. Preparation of replication-defective adenovirus containing an MDA-7 encoding nucleic acid (i.e., a mda-7 gene). (A) shows the pCMV/mda-7 plasmid; (B) shows recombination between pCMV/mda-7 and pJM17 in 293 cells; and (C) shows the product Ad.mda-7 virus.

Figure 3A:
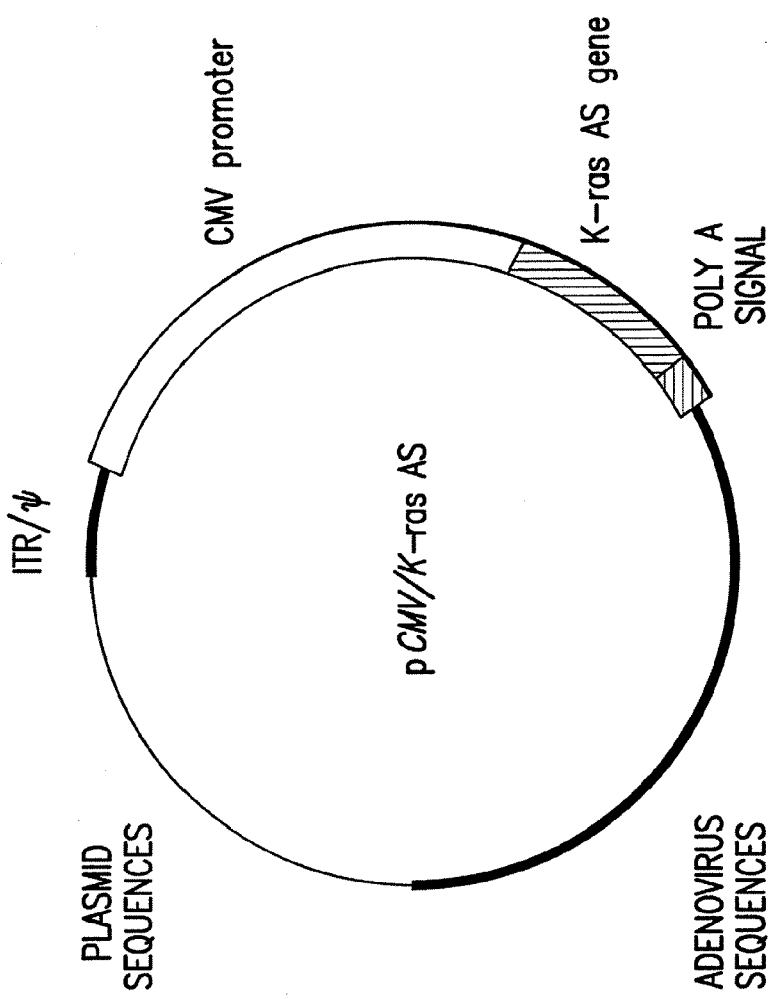
Figure 3B:
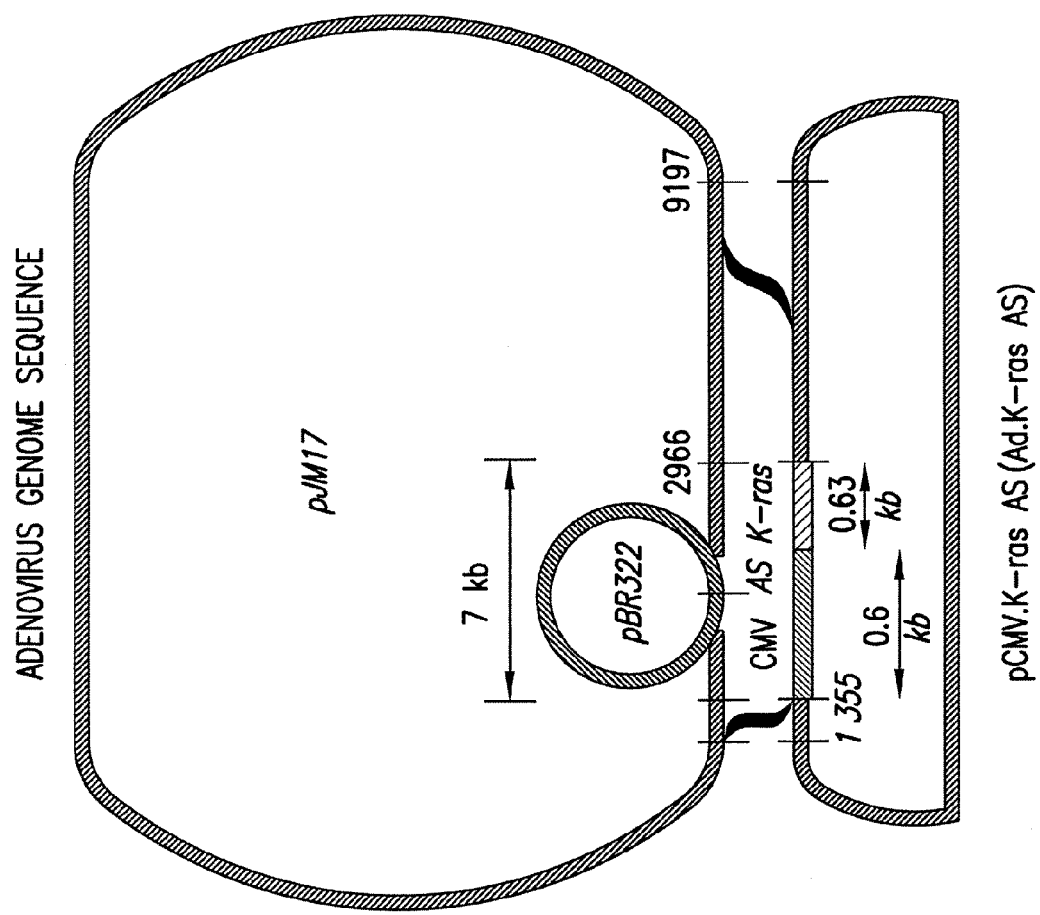
Figure 3C:
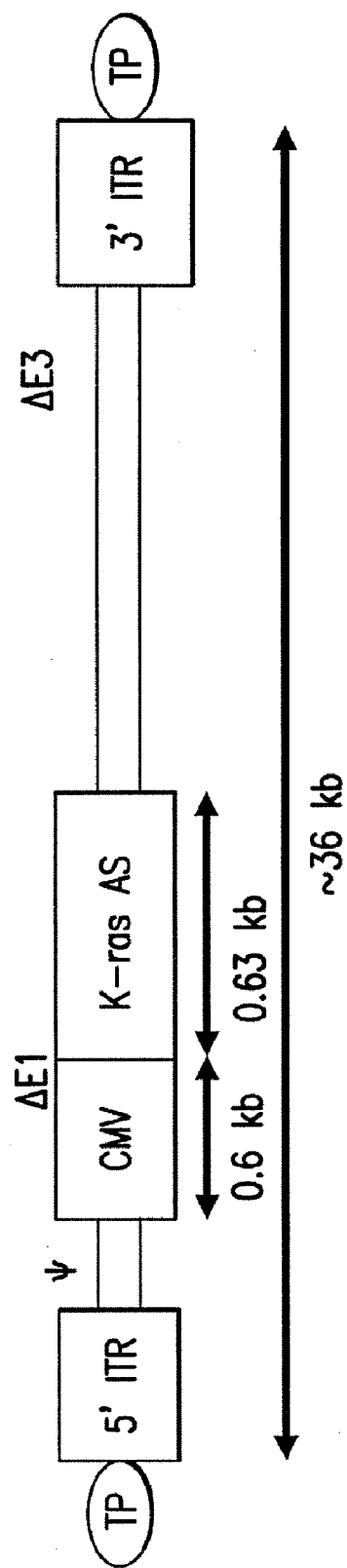

FIGS. 3A-C. Preparation of replication-defective adenovirus containing an AS K-ras encoding nucleic acid. (A) shows the pCMV/K-ras AS plasmid; (B) shows recombination between pCMVlK-ras AS and pJM17 in 293 cells; and (C) shows the product Ad.K-ras AS virus.

Figure 4:
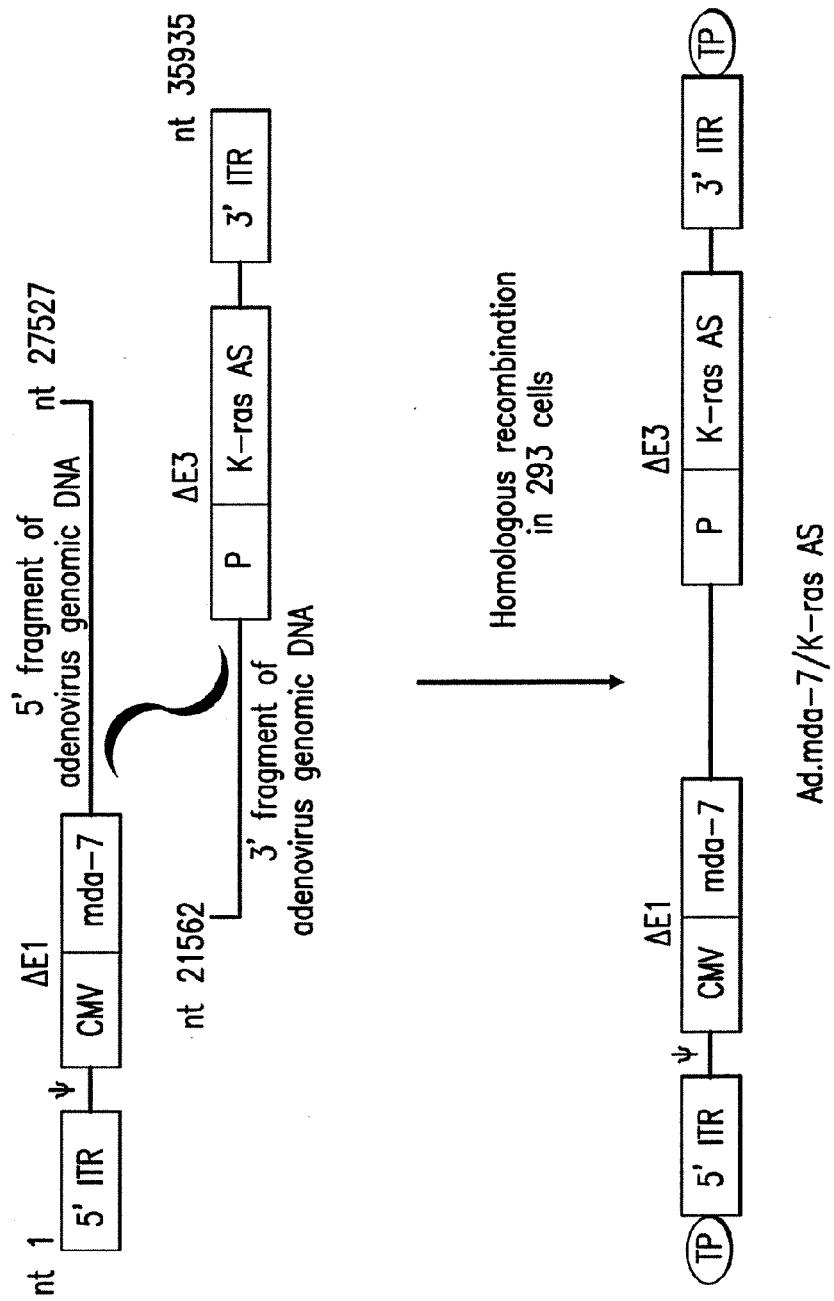

FIG. 4. Diagram showing the preparation of bipartite Ad.mda-7/K-ras AS. The figure is not drawn to scale, but terminal nucleotides are shown, based on the length of 3595 nucleotides for Ad serotype 5, from which this vector is derived. The ovals containing the letters "TP" represent the terminal protein covalently bound to the native genome. The cytomegalovirus immediate early (CMV) promoter was used to drive the transcription of both mda-7 and K-ras AS from the bipartitie vector.

Figure 5:
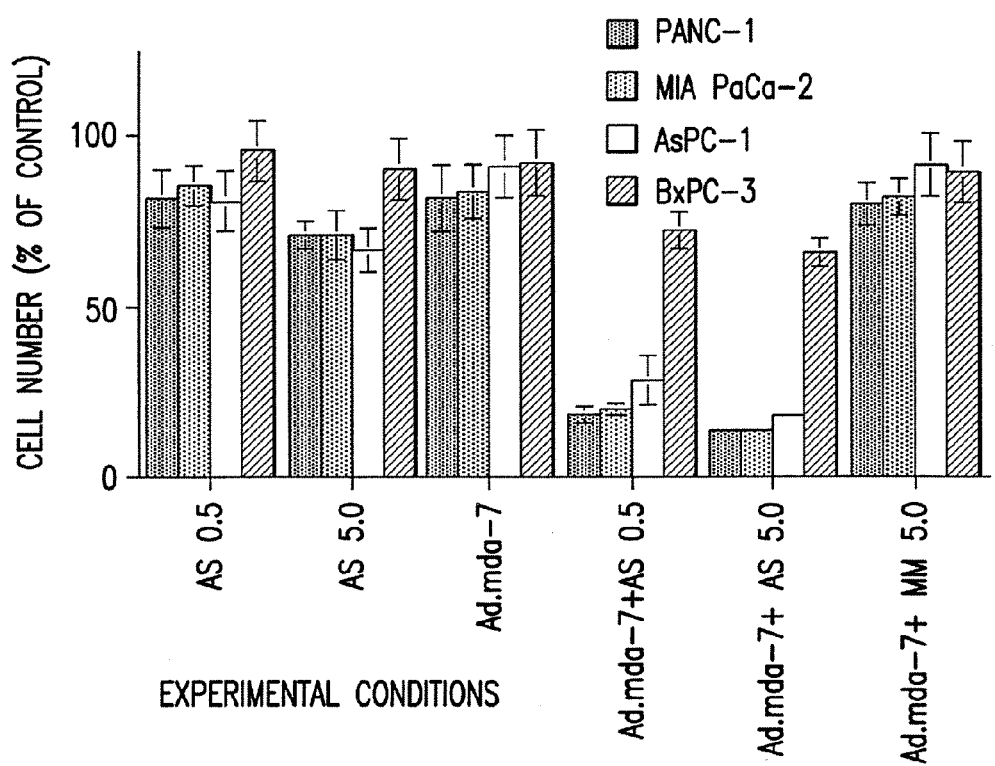

FIG. 5. Synergistic inhibition of growth in mutated K-ras pancreatic carcinoma cells (pancreatic carcinoma cells containing a mutation in the K-ras gene) by the combination of Ad.mda-7 (a replication-defective adenovirus carrying the mda-7 gene in expressible form) and AS K-ras PS ODN (a phosphorothioate linked antisense ras oligonucleotide). Cells were treated with the indicated agents for three days and viable cell counts were determined by hemocytometer. AS PS ODN: 0.5 or 5.0 µM; Ad.mda-7: 100 plaque-forming units ("pfu")/cell; MM PS ODN (mismatched oligonucleotide): 5.0 µM. Results are the average of four plates±standard deviation ("S.D.") from the mean. Qualitatively similar results were obtained in an additional experiment.

FIGS. 6A-P. The combination of Ad.mda-7 with AS K-ras PS ODN synergistically suppressed growth and decreased survival in mutated K-ras pancreatic carcinoma cells. Pancreatic carcinoma cell lines having a mutated K-ras gene (AsPC-1 [panels A,E,I,M], MIA PaCa-2 [panels B,F,J,N], and PANC-1 [panels C,G,K,O]) and pancreatic carcinoma cell line BxPC-3 (panels D,H,L,P), which has a wild-type ras gene, were treated as indicated and representative microscopic fields were photographed 3 days later. Cells were either untreated (control, panels A-D), treated with 0.5 µM AS K-ras PS ODN (panels E-H), infected with Ad.mda-7 (100 pfu/cell; panels I-L) or infected with Ad.mda-7 (100 pfu/cell) and then treated with 0.5 µM AS K-ras PS ODN (panels M-P).

Figure 7:
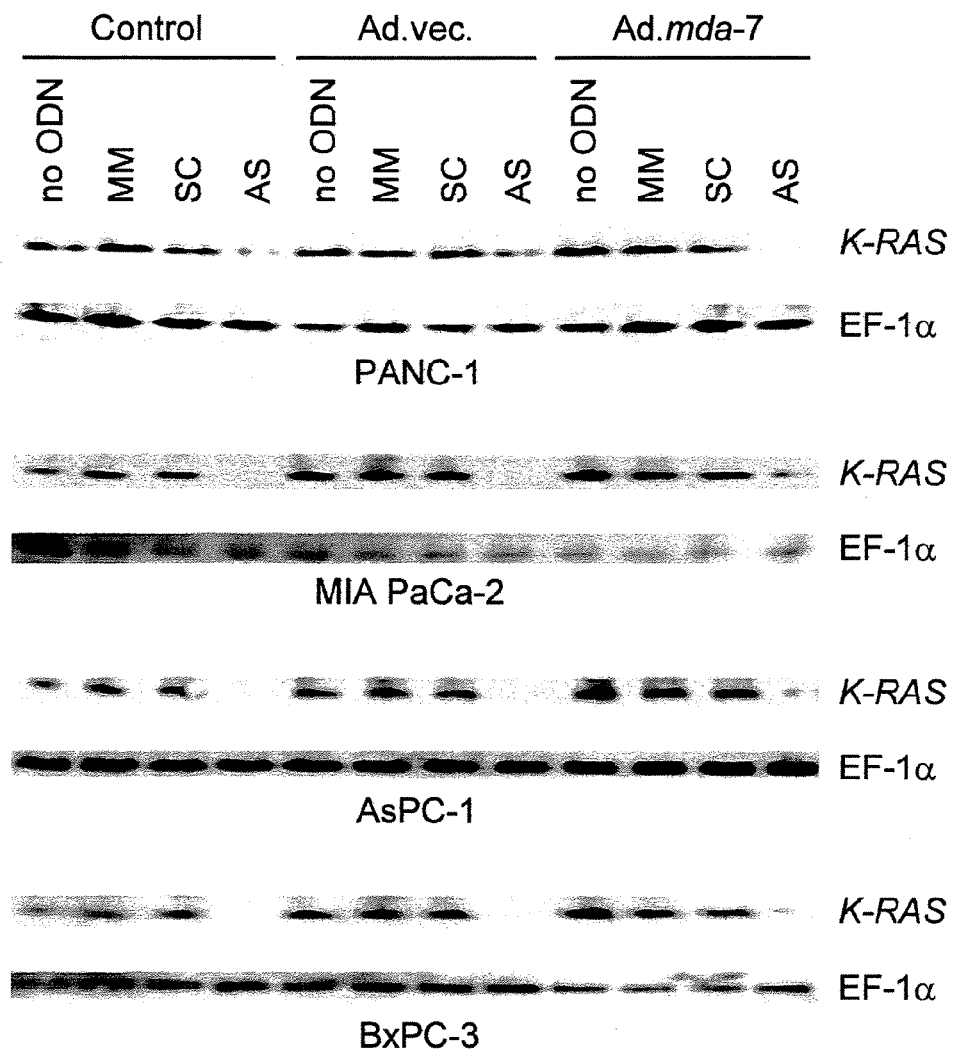

FIG. 7. AS K-ras PS ODN inhibited K-RAS protein synthesis in pancreatic carcinoma cells. The figure depicts Western blot analysis of K-RAS and EF-1α protein levels in cells treated with the various agents for three days. The concentration of MM, SC (scrambled) and AS PS ODN was 0.5 µM and the dose of virus was 100 pfu/cell.

Figure 8:
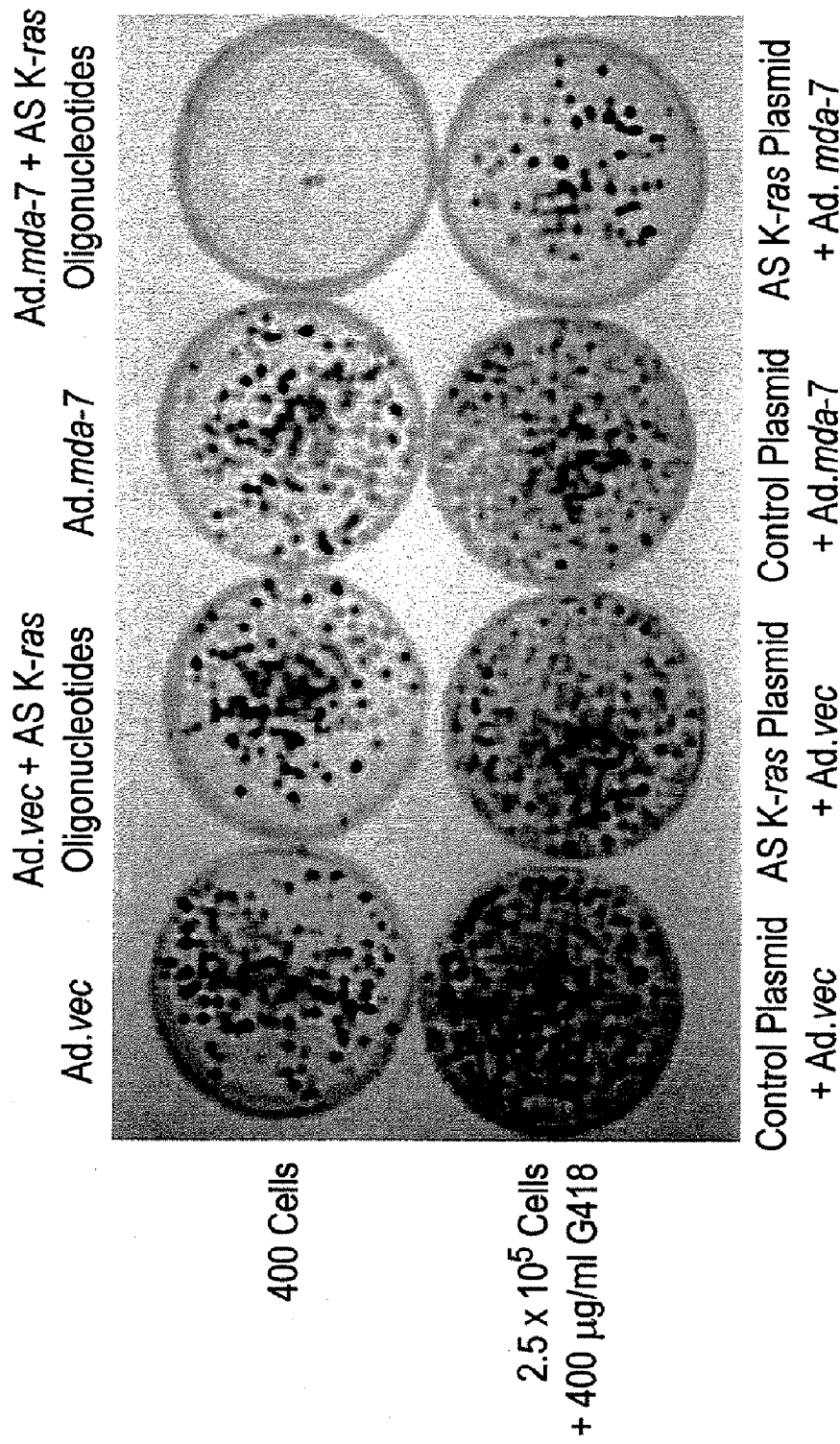

FIG. 8. The combination of Ad.mda-7 plus AS K-ras PS ODN or AS K-ras plasmids synergistically inhibited colony formation in mutated K-ras MIA PaCa-2 pancreatic carcinoma cells. The upper row of culture plates illustrates the effect of Ad.mda-7 plus AS K-ras PS ODN on MIA PaCa-2 colony formation. Cells were infected with 100 pfu/cell of Ad.vec (empty vector control) or Ad.mda-7, treated with 0.5 µM AS K-ras PS ODN plus 10 microliters lipofectamine, reseeded at a density of 400 cells/plate and fixed and stained with Giemsa after three weeks. The lower row of culture plates illustrates the effect of Ad.mda-7 plus AS K-ras plasmid transfection on MIA PaCa-2 G418 resistant colony formation. Cells were infected with 100 pfu/cell of Ad.vec or Ad.mda-7, transfected with 10 micrograms of plasmid (either control pcDNA3.1 lacking insert, or the pcDNA3.1 vector containing a 346 nucleotide AS K-ras fragment), reseeded at a density of $2.5 \times 10^5$ cells/plate, selected in 400 µg/ml of G418 and then G418-resistant colonies were fixed and stained with Giemsa after three weeks.

Figure 9:
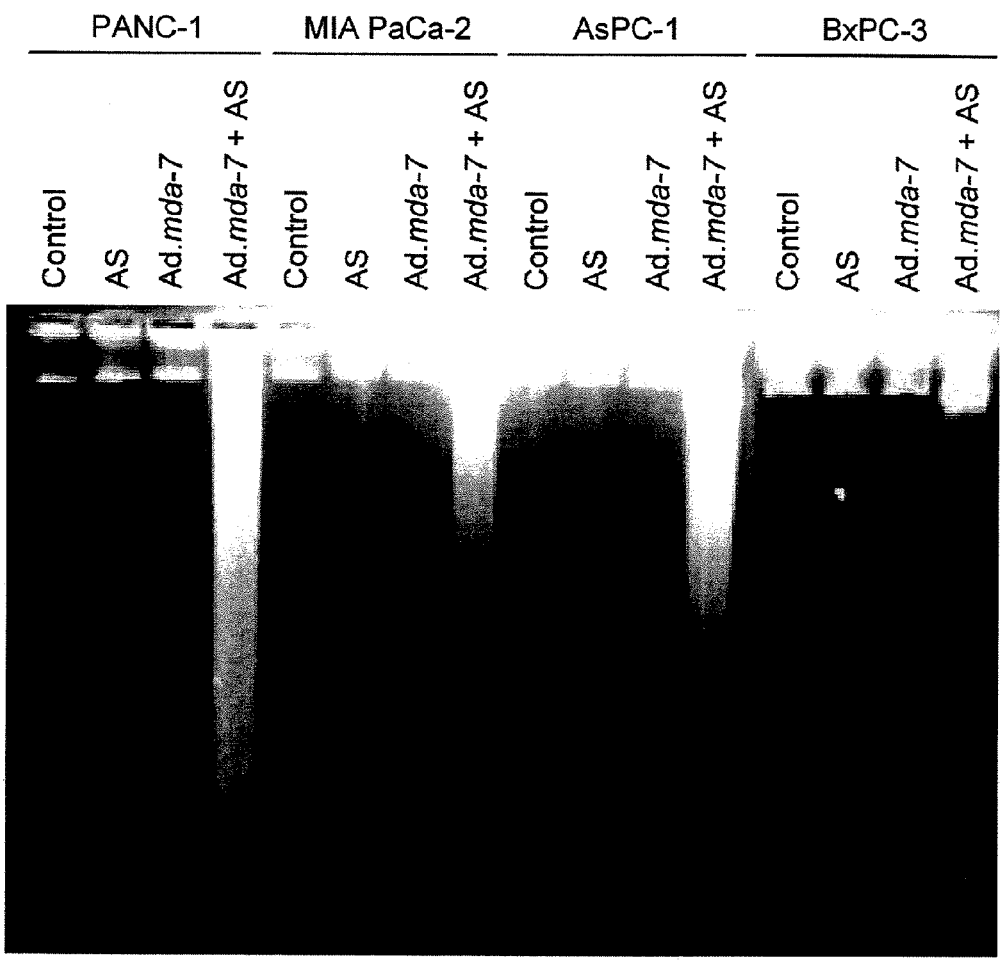

FIG. 9. Ad.mda-7 and AS K-ras PS ODN induced nucleosomal DNA degradation in K-ras mutant human pancreatic cancer cells. The indicated cell types were treated as indicated for 3 days. AS: 0.5 µM AS K-ras PS ODN; Ad.mda-7: 100 pfu/cell; Ad.mda-7 infected (100 pfu/cell)+0.5 µM AS K-ras PS ODN. Nucleosomal ladder formation was determined as described in Koich, 2000, Biochem. J. 351:289-305.

FIGS. 10A-D. MDA-7 protein was detected in mutated K-ras pancreatic carcinoma cells infected with Ad.mda-7 and treated with AS K-ras PS ODN. Cell lines PANC-1 (panel A), MIA PaCa-2 (panel B), AsPC-1 (panel C) and BxPC-3 (panel D) were treated for one day as indicated. In each of the panels, the rows contain cells treated as follows: 1=control cells; 2=AS K-ras PS ODN treated; 3=Ad.vec treated; 4=Ad.vec+AS K-ras PS ODN treated; 5=Ad.mda-7 treated; 6=Ad.mda-7+MM PS ODN treated; 7=Ad.mda-7+SC PS ODN treated; 8=Ad.nzda-7+AS K-ras PS ODN treated; 9=PC-3 prostate carcinoma cells treated for one day with Ad.vec; 10=PC-3 cells treated for one day with Ad.mda-7 (used as a positive control for mda-7 protein expression). Lysates of treated cells were evaluated by Western blotting for MDA-7 and EF-1α protein as described in Su et al., 1998, Proc. Natl. Acad. Sci. U.S.A. 95:14400-14405; Lebedeva et al., 2000, Cancer Res. 60:6052-6060; and Su et al., 1995, Intl. J. Oncol. 7:1279-1284. Arrowhead and bracket indicate MDA-7 proteins detected by Western blotting. The concentration of MM, SC and AS PS ODN was 0.5 µM and the dose of virus was 100 pfu/cell.

Figure 11:
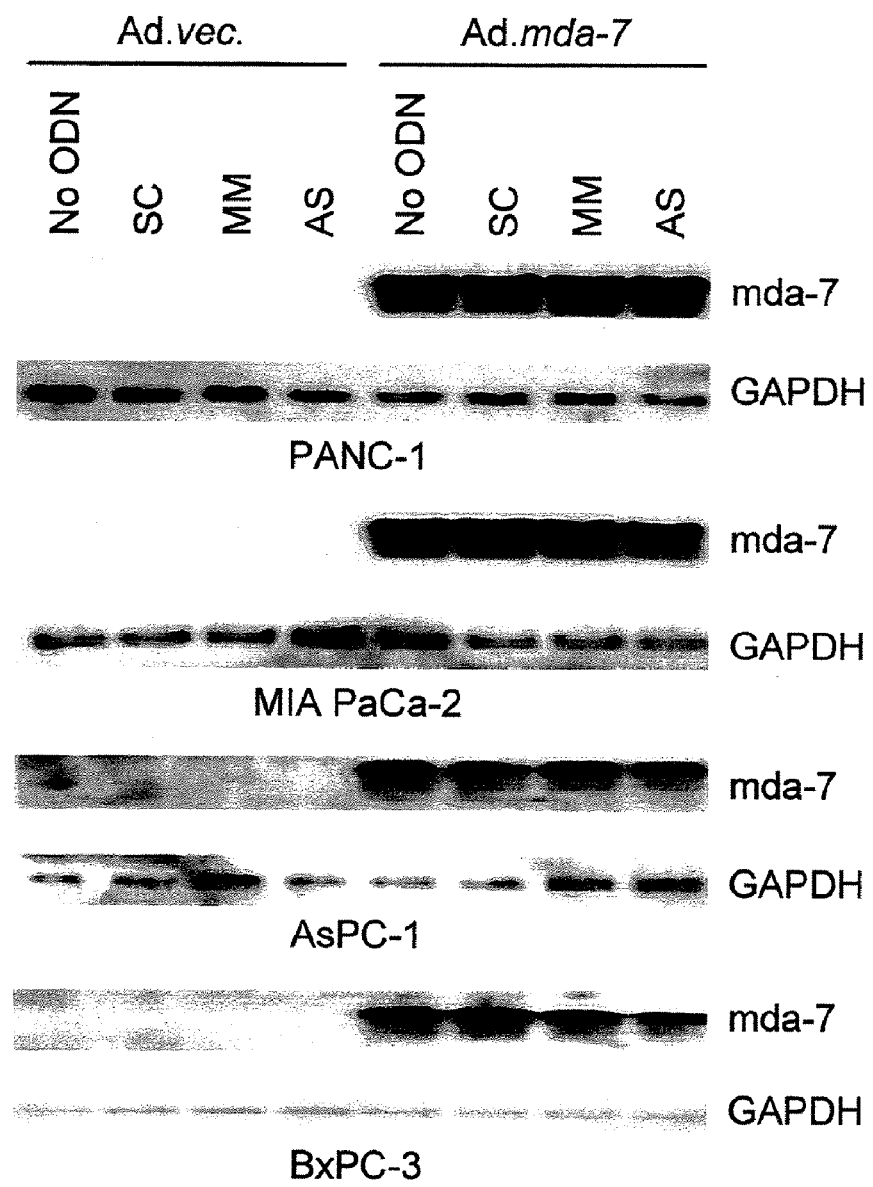

FIG. 11. Expression of mda-7 mRNA in Ad.mda-7 infected mutated and wild-type K-ras pancreatic carcinoma cells. The indicated cell lines were treated for three days, total RNA was isolated and analyzed by Northern blotting for inda-7 and GAPDH mRNA. The concentration of SC, MM and AS PS ODN was 0.5 µM and the dose of virus was 100 pfu/cell.

Figure 12:
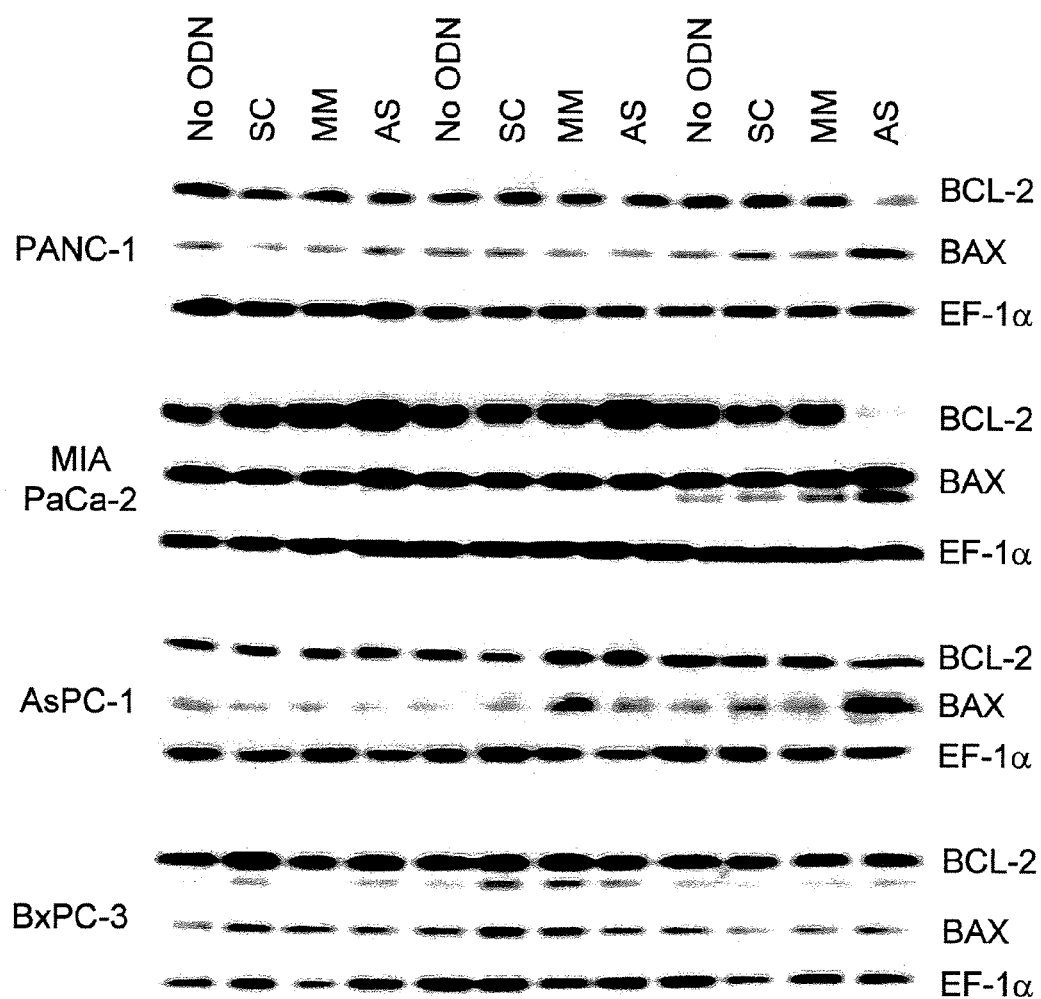

FIG. 12. Expression of BAX, BCL-2 and EF-1α proteins in pancreatic carcinoma cells after various treatment protocols. The different cell lines were treated for three days as indicated and the levels of the respective proteins were determined using 30 µg of total protein lysates by Western blotting using the respective antibodies as described in Su et al., 1998, Proc. Natl. Acad. Sci. U.S.A. 95:14400-14405; Lebedeva et al., 2000, Cancer Res. 60:6052-6060; and Su et al., 1995, Intl. J. Oncol. 7:1279-1284. The concentration of MM, SC and AS PS ODN was 0.5 µM and the dose of virus was 100 pfu/cell.

Figure 13:
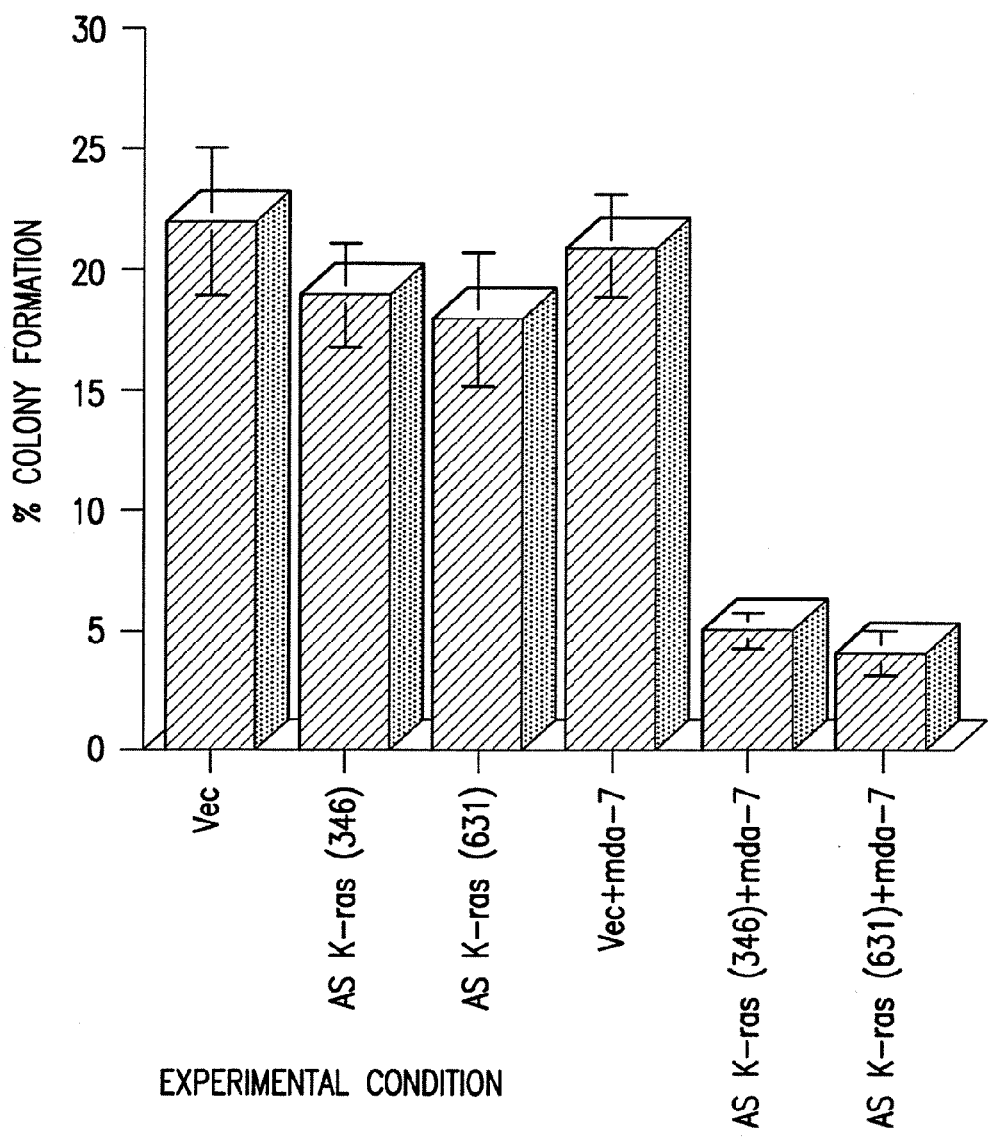

FIG. 13. Percent colony formation of MIA PaCa-2 cells which were, as represented by bars from left to right, either transfected with empty vector ("Vec"); transfected with vector containing a 346 K-ras fragment, in antisense orientation ("AS K-ras (346)"); transfected with vector containing a 631 K-ras fragment, in antisense orientation ("AS-Kras (631)"); transfected with empty vector and infected with Ad.mda-7 ("Vec+mda-7"); transfected with vector encoding AS K-ras (346) and infected with Ad.mda-7 ("AS K-ras (346)+mda-7"); or transfected with vector encoding AS K-ras (631) and infected with Ad.mda-7 ("AS K-ras(631)+mda-7").

Figure 14A:
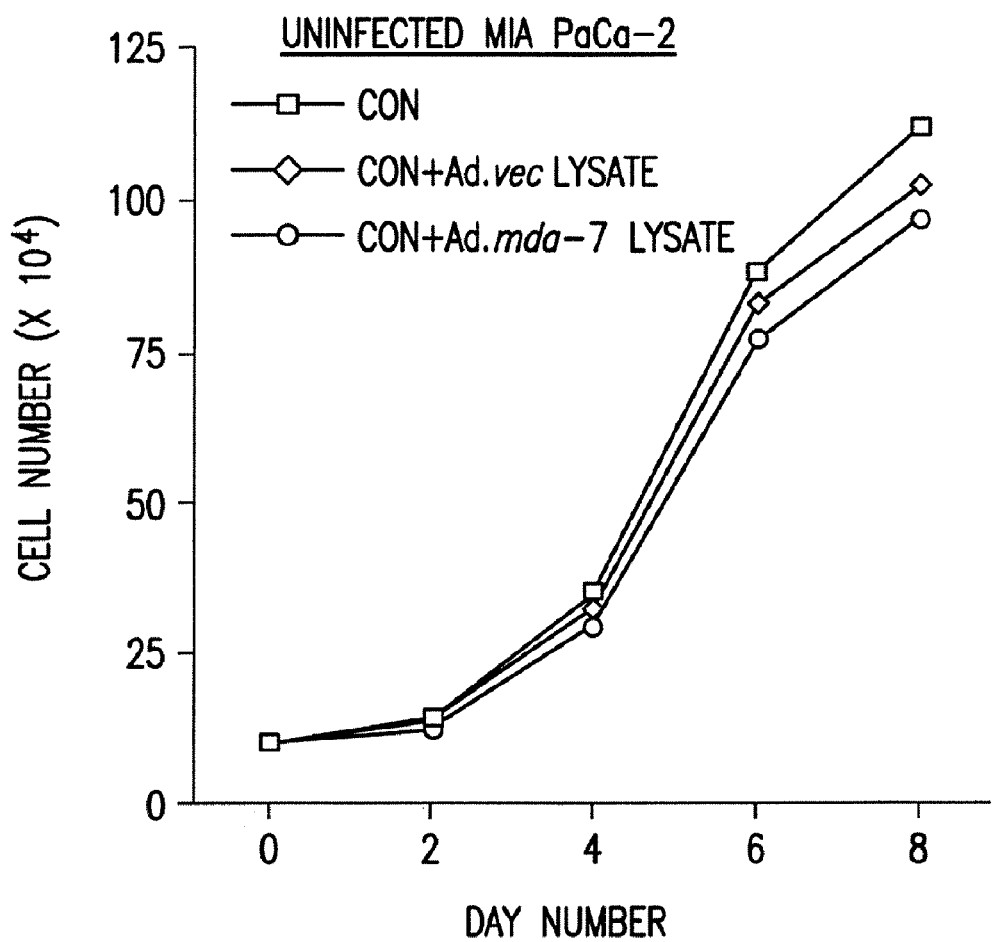
Figure 14B:
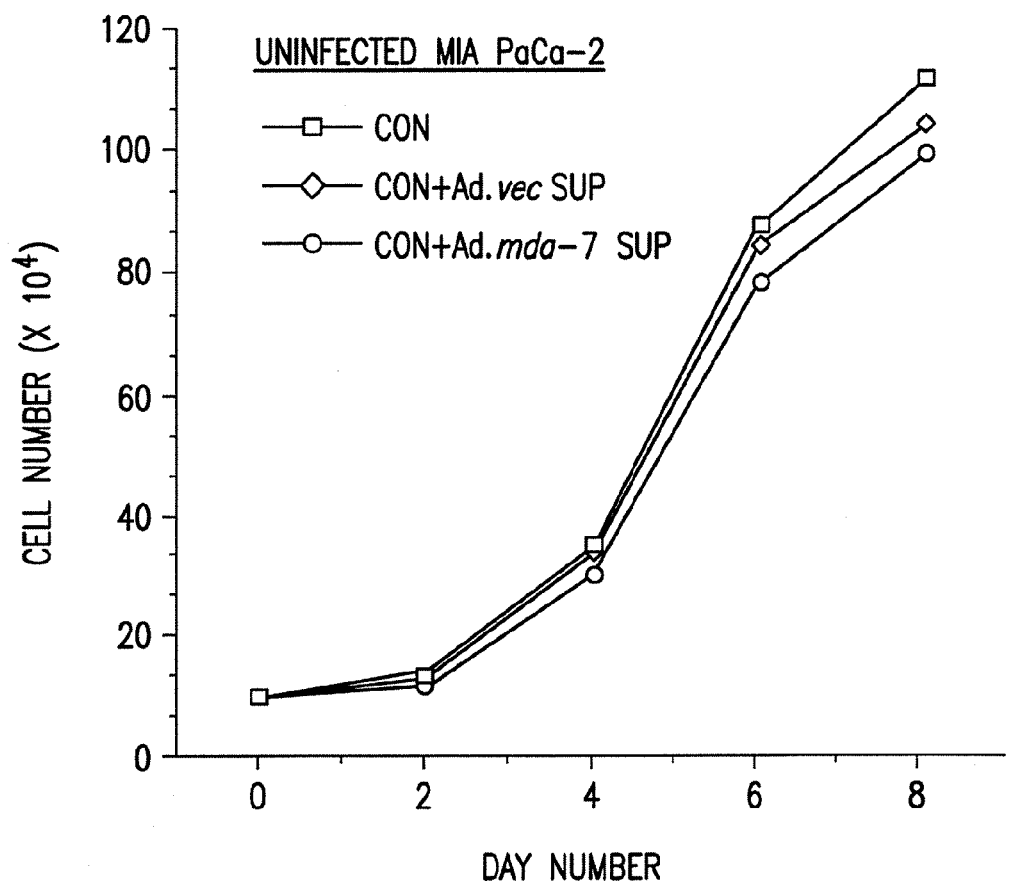

FIGS. 14A-B. Controls for experiments described in Section 8. (A) Numbers of uninfected MIA PaCa-2 pancreatic carcinoma cells treated with either a lysate of hepatocytes infected with empty adenovirus (empty diamond; "Con+Ad.vec Lysate"); a lysate of hepatocytes infected with Ad.mda-7 (empty circle; "Con+Ad.mda-7 Lysate"); or untreated (empty square; "Con"). (B) Numbers of uninfected MIA PaCa-2 pancreatic carcinoma cells treated with either a culture supernatant of hepatocytes infected with empty adenovirus (empty diamond; "Con+Ad.vec Sup"); a culture supernatant of hepatocytes infected with Ad.mda-7 (empty circle; "Con+Ad.mda-7 Sup"); or untreated (empty square; "Con").

Figure 15A:
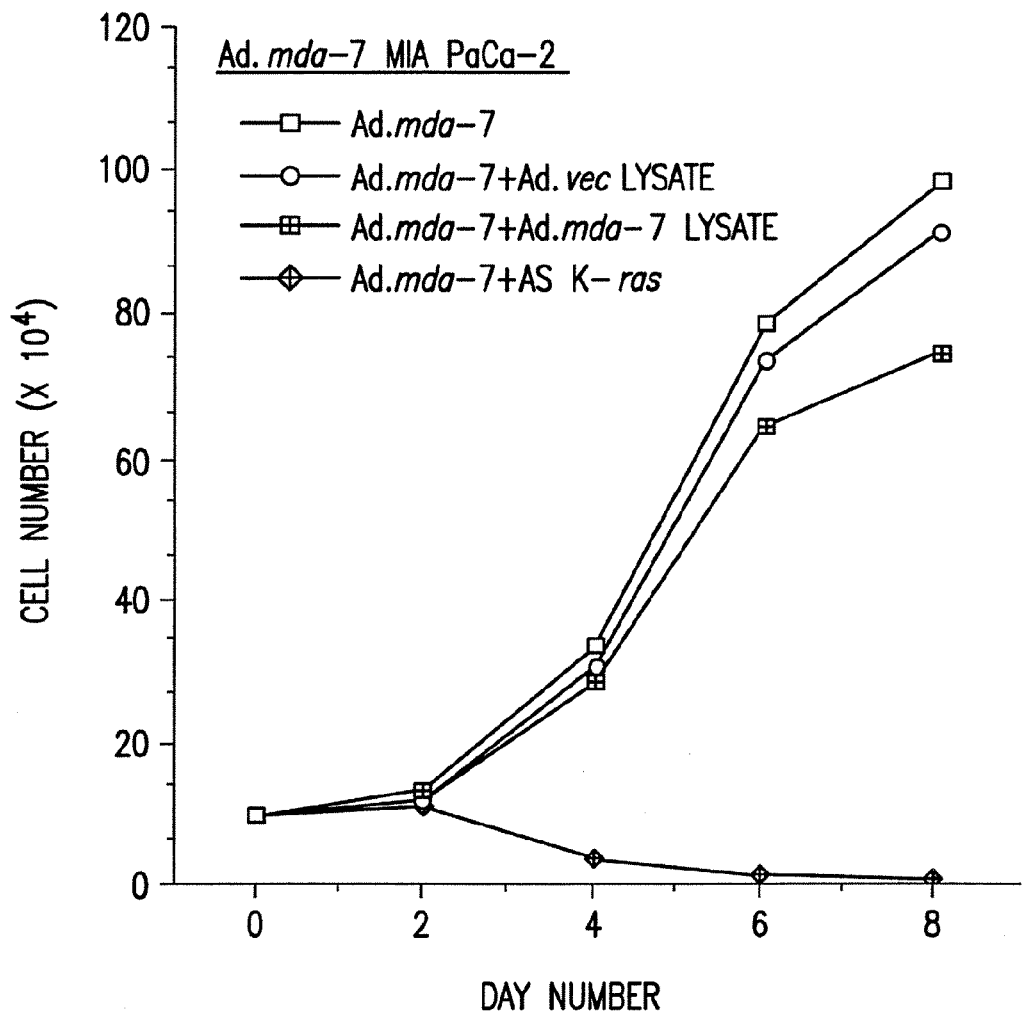
Figure 15B:
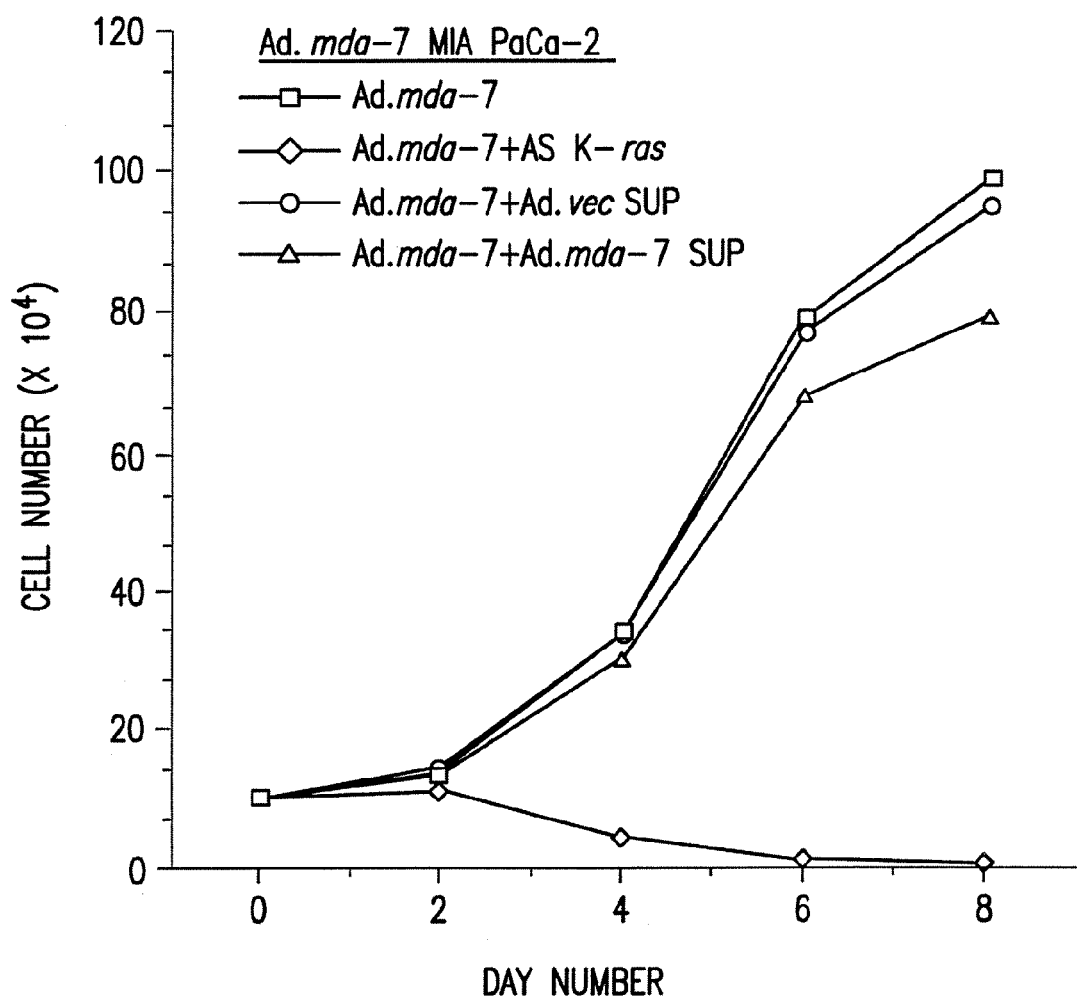

FIGS. 15A-B. (A) Numbers of MIA PaCa-2 pancreatic carcinoma cells, infected with Ad.mda-7, which were either untreated (empty square; "Ad.mda-7"), or treated with a lysate of hepatocytes infected with empty adenovirus (empty circle; "Ad.mda-7+Ad.vec Lysate"); or a lysate of hepatocytes infected with Ad.mda-7 (square with+overstrike; "Ad.mda-7+Ad.mda-7 Lysate"); or by transfection with AS K-ras phosphorothioate-linked oligonucleotides ("PS ODN") (diamond with+overstrike; "Ad.mda-7+AS K-ras"). (B) Numbers of MIA PaCa-2 pancreatic carcinoma cells, infected with Ad.mda-7, which were either untreated (empty square; "Ad.mda-7"), or treated with a culture supernatant of hepatocytes infected with empty adenovirus (empty circle; "Ad.mda-7+Ad.vec Sup"); or a culture supernatant of hepatocytes infected with Ad.mda-7 (empty triangle; "Ad.mda-7+Ad.mda-7 Sup"); or by transfection with AS K-ras PS ODN (empty diamond; "Ad.mda-7+AS K-ras").

Figure 16A:
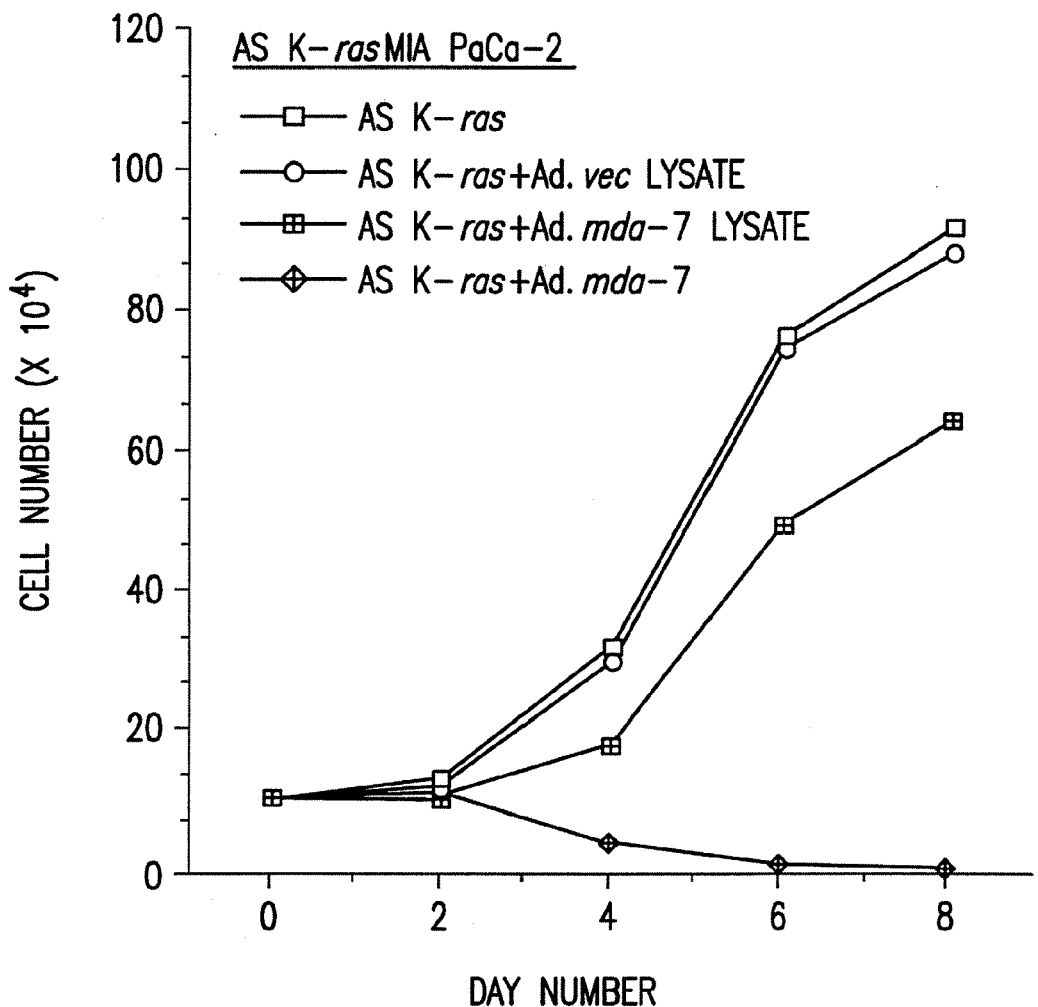
Figure 16B:
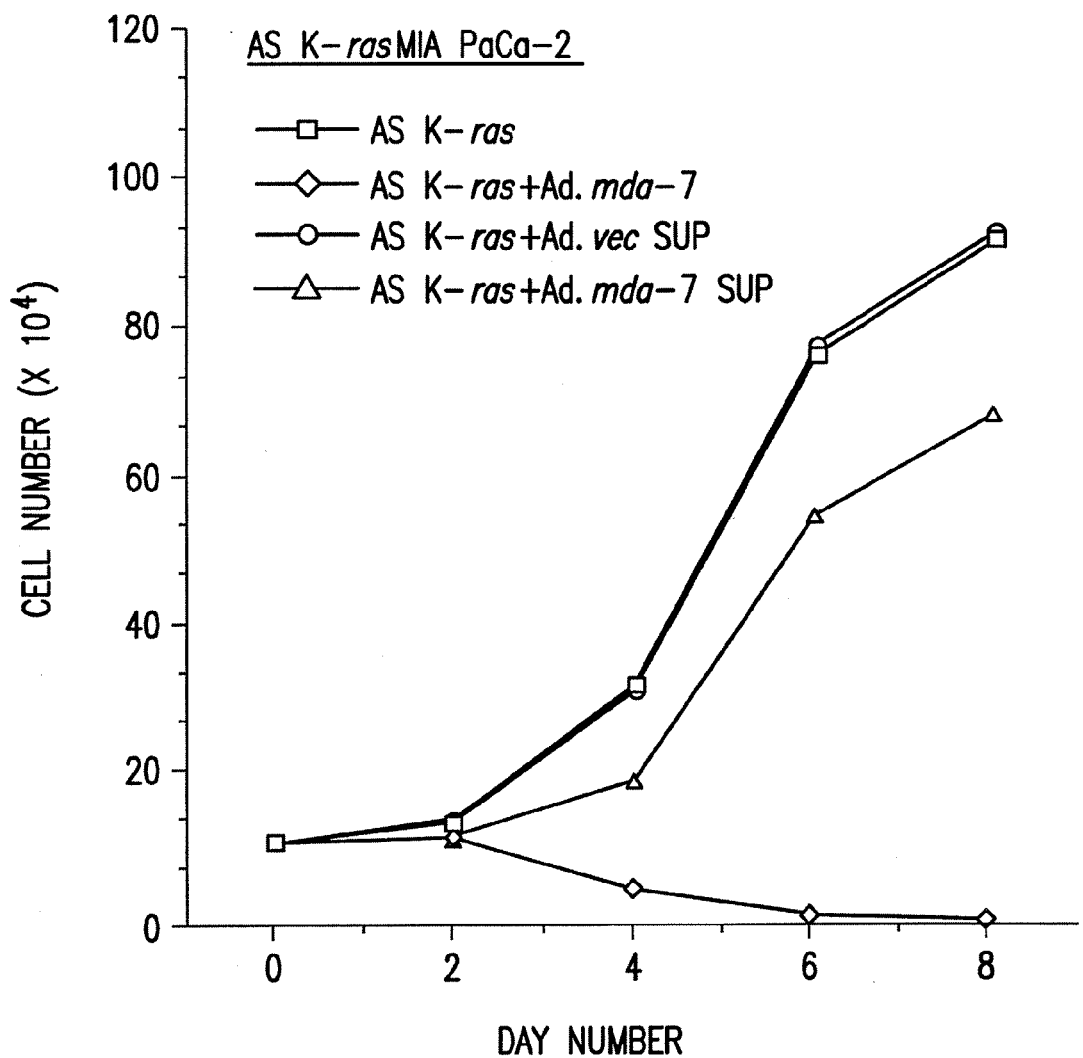

FIGS. 16A-B. (A) Numbers of MIA PaCa-2 pancreatic carcinoma cells, transfected with AS K-ras PS ODN, which were either untreated (empty square; "AS K-ras"), or treated with a lysate of hepatocytes infected with empty adenovirus (empty circle; "AS K-ras+Ad.vec Lysate"); or a lysate of hepatocytes infected with Ad.mda-7 (square with+overstrike; "AS K-ras+Ad.mda-7 Lysate"); or by infection with Ad.mda-7 (diamond with+overstrike; "Ad.mda-7+AS K-ras").

(B) Numbers of MIA PaCa-2 pancreatic carcinoma cells, transfected with AS K-ras PS ODN, which were either untreated (empty square; "AS K-ras"), or treated with a culture supernatant of hepatocytes infected with empty adenovirus (empty circle; "AS K-ras-7+Ad.vec Sup"); a culture supernatant of hepatocytes infected with Ad.mda-7 (empty triangle; "AS K-ras+Ad.mda-7 Sup"); or by infection with Ad.mda-7 (empty diamond; "AS K-ras+Ad.mda-7").

FIGS. 17A-D. Effects of Ad.mda-7 and Ad.K-ras AS, alone and in combination, on the growth of (A) AsPC-1; (B) BxPC-3; (C) PANC-1; and (D) MIA PaCa-2 pancreatic carcinoma cells.

Figure 18:
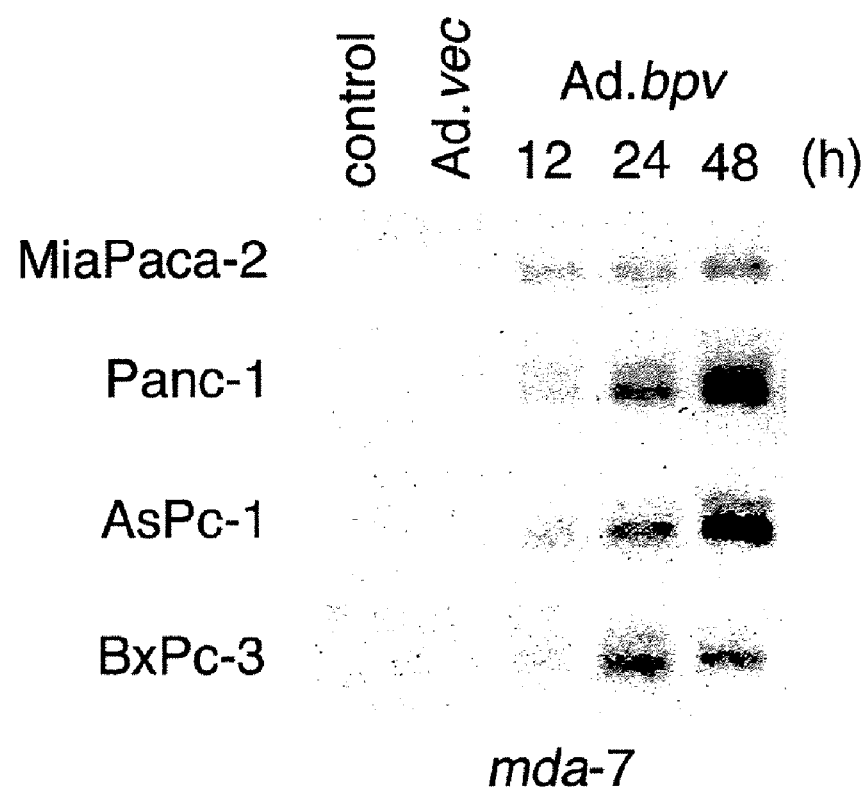

FIG. 18. Infection of pancreatic cancer cell lines with Ad.bpv results in the production of mda-7 mRNA.

Figure 19:
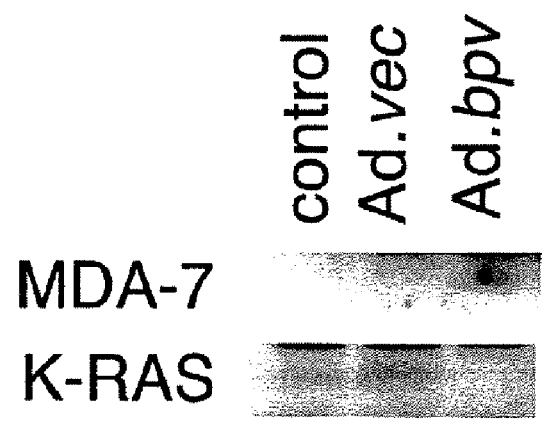
Figure 20A:
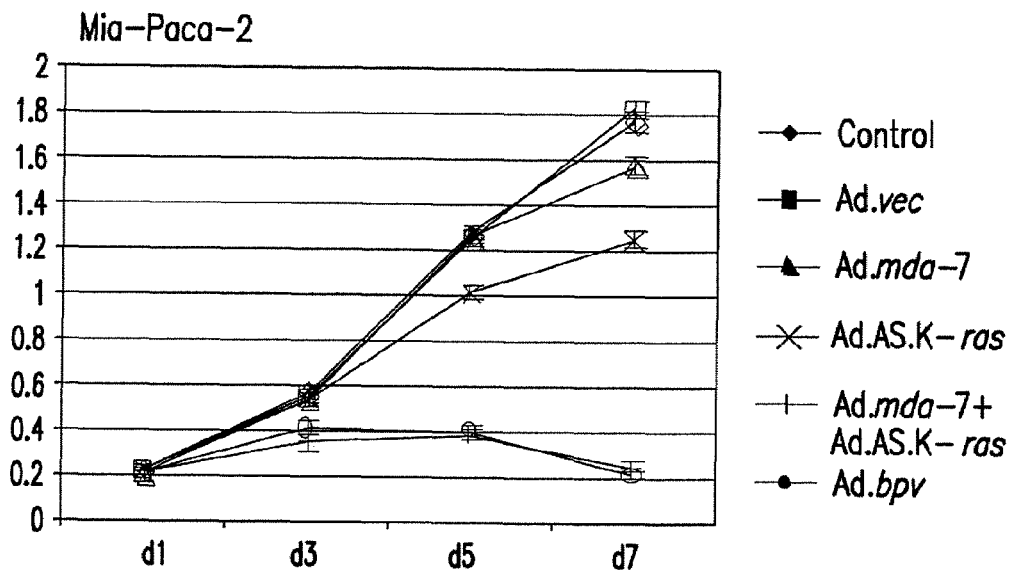
Figure 20B:
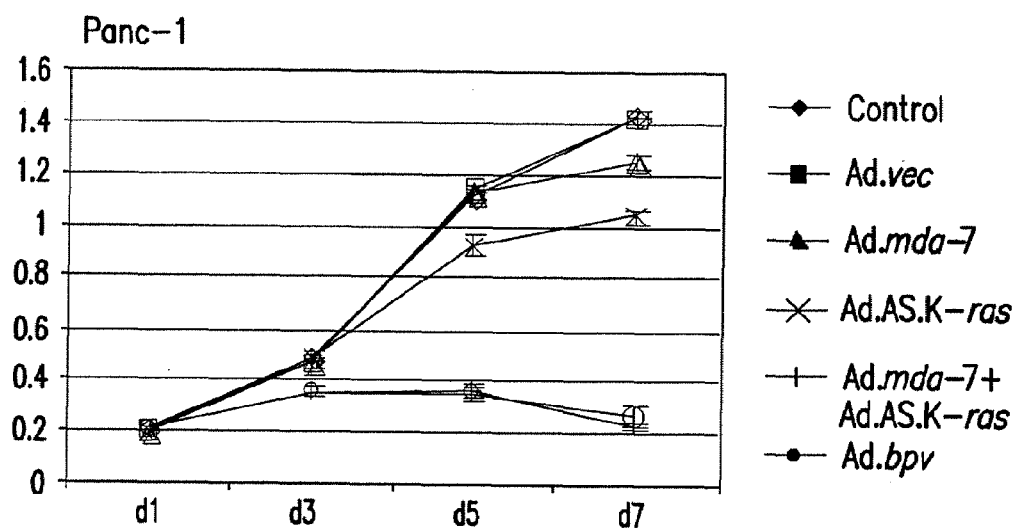
Figure 20C:
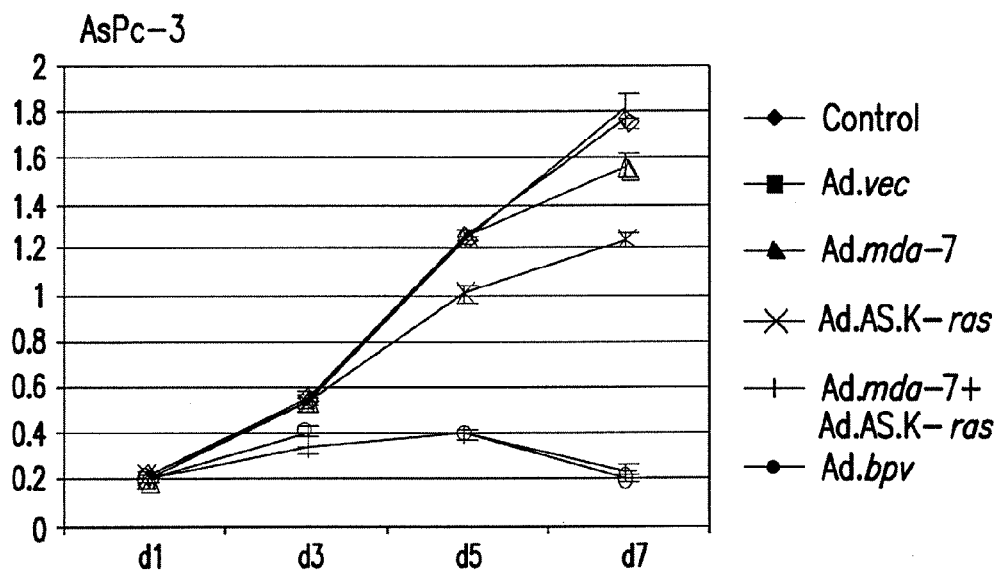
Figure 20D:
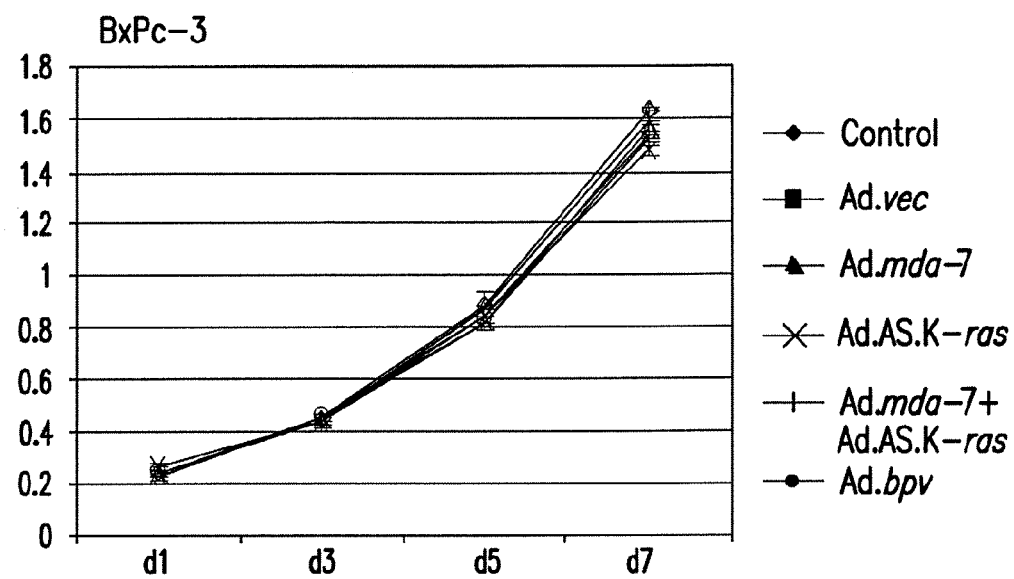

FIG. 19. Infection of Mia Paca-2 cells with Ad.bpv results in the production of MDA-7 protein.

FIGS. 20A-D. Infection of pancreatic cancer cell lines with Ad.bpv results in inhibition of growth of (A) AsPC-1, (B) BxPC-3, (C) PANC-1, and (D) MIA PaCa-2 pancreatic carcinoma cells. The data represent mean±S.D. of quadruplicate samples from three independent experiments.

5. DETAILED DESCRIPTION OF THE INVENTION

For clarity of presentation, and not by way of limitation, the detailed description is divided into the following subsections:

(i) compositions that increase MDA-7 protein;
(ii) compositions that decrease RAS activity;
(iii) assays to identify suitable target cells;
(iv) assays to identify anti-cancer small molecules; and
(v) methods of use.

5.1. Compositions that Increase MDA-7 Protein

The first component necessary for practicing the methods of the invention is a means for increasing the amount of MDA-7 protein in a cancer cell and/or within a population of cancer cells. The convention of distinguishing between the gene and protein by using lower case versus capital letters is followed herein, so that mda-7 refers to nucleic acid molecules and MDA-7 refers to proteins (the same designations are used herein for ras genes and their encoded proteins). The term "gene" as used herein refers to any nucleic acid from which a functional protein can ultimately be derived, and encompasses, for example, genomic DNA as well as cDNA. The term "MDA-7" as used herein refers to a protein having essentially the amino acid sequence set forth as SEQ ID NO:2, having Genbank Accession Number U16261. A nucleic acid encoding MDA-7 may have the coding sequence as set forth in SEQ ID NO:1, Genbank Accession No. U16261, or another sequence which, when translated, produces a protein having essentially the same amino acid sequence. It should be noted that the portion of the nucleic acid sequence presented as SEQ ID NO:1 which constitutes the protein encoding region extends from nucleotide 275 to nucleotide 895. The scope of the invention embraces functional equivalents of the nucleic acid and protein which vary in insignificant ways from the native molecules; for example, it includes isolated nucleic acids which hybridize to the nucleic acid sequence set forth as SEQ ID NO:1 under stringent hybridization conditions, e.g., hybridization in 0.5 M $NaHPO_4$, 7 percent sodium dodecyl sulfate ("SDS"), 1 mM ethylenediamine tetraacetic acid ("EDTA") at 65° C., and washing in 0.1×SSC/0.1 percent SDS at 68° C. (Ausubel et al., 1989, Current Protocols in Molecular Biology, Vol. I, Green Publishing Associates, Inc., and John Wiley & Sons, Inc. New York, at p. 2.10.3), as well as the proteins encoded by such hybridizing sequences. It also includes nucleic acids having essentially the sequence set forth as SEQ ID NO:1, but modified to contain restriction sites appropriate for insertion into a particular expression vector.

The use of the term "increasing" does not presuppose that detectable levels of MDA-7 protein are constitutively present in the cell prior to treatment, such that the level may be "increased" from an undetectable or 0 level. An increase in MDA-7 protein may be evaluated indirectly by detecting the presence of and/or quantifying the amount of MDA-7 encoding mRNA or directly by detecting the presence of and/or quantifying the amount of MDA-7 protein. MDA-7 encoding mRNA may be detected, for example, by Northern blot or by reverse transcription-polymerase chain reaction ("RT-PCR") (e.g. using mda-7 specific primers such as ATGCTCTGTCCCTGCAGATA (SEQ ID NO:3) and CTCTGGATGCTGTGAAGAGT (SEQ ID NO:4) as described in Jiang et al., 1995, Oncogene 11:2477-2486. MDA-7 protein may be detected by Western blot, for example using antibody directed against an MDA-7 specific peptide such as Pro-Ser-Gln-Glu-Asn-Glu-Met-Phe-Ser-Ile-Arg-Asp (SEQ ID NO:5; amino acid residues 153-164 of MDA-7 protein), also described in Jiang et al., 1995, Oncogene 11:2477-2486. In preferred embodiments, the amount of MDA-7 protein increases by a factor of at least 5, and more preferably by a factor of at least 10.

The amount of MDA-7 protein may be increased by increasing the amount of mda-7 encoding mRNA in a cancer cell. For instance, the amount of MDA-7 encoding mRNA may be increased by introducing, into the cell, an expression vector containing MDA-7 encoding nucleic acid, in an expressible form. An "expressible form" is one which contains the necessary elements for transcription and/or translation. For example, the MDA-7 encoding nucleic acid may be operatively linked to a suitable promoter element, and may comprise transcription initiation and termination sites, nucleic acid encoding a nuclear localization sequence, ribosome binding sites, polyadenylation sites, mRNA stabilizing sequences, etc.

For example, where mda-7 nucleic acid is to be transcribed into RNA, the nucleic acid may be operatively linked to a suitable promoter element, for example, but not limited to, the cytomegalovirus immediate early promoter, the Rous sarcoma virus long terminal repeat promoter, the human elongation factor 1α promoter, the human ubiquitin c promoter, etc. It may be desirable, in certain embodiments of the invention, to use an inducible promoter. Non-limiting examples of inducible promoters include the murine mammary tumor virus promoter (inducible with dexamethasone); commercially available tetracycline-responsive or ecdysone-inducible promoters, etc. In specific non-limiting embodiments of the invention, the promoter may be selectively active in cancer cells; one example of such a promoter is the PEG-3 promoter, as described in International Patent Application No. PCT/US99/07199, Publication No. WO 99/49898 (published in English on Oct. 7, 1999); other non-limiting examples include the prostate specific antigen gene promoter (O'Keefe et al., 2000, Prostate 45:149-157), the kallikrein 2 gene promoter (Xie et al., 2001, Human Gene Ther. 12:549-561), the human alpha-fetoprotein gene promoter (Ido et al., 1995, Cancer Res. 55:3105-3109), the c-erbB-2 gene promoter (Takalcuwa et al., 1997, Jpn. J. Cancer Res. 88:166-175), the human carcinoembryonic antigen gene promoter (Lan et al., 1996, Gastroenterol. 111: 1241-1251), the gastrin-releasing peptide gene promoter (Inase et al., 2000, Int. J. Cancer 85:716-719). the human telomerase reverse transcriptase gene promoter (Pan and Koennen, 1999, Med. Hypotheses 53:130-135), the hexokinase II gene promoter (Katabi et al., 1999, Human Gene Ther. 10:155-164), the L-plastin gene promoter (Peng et al., 2001, Cancer Res. 61:4405-4413), the neuron-specific enolase gene promoter (Tanaka et al., 2001, Anticancer Res. 21:291-294), the midkine gene promoter (Adachi et al., 2000, Cancer Res. 60:4305-4310), the human mucin gene MUC1 promoter (Stackhouse et al., 1999, Cancer Gene Ther. 6:209-219), and the human mucin gene MUC4 promoter (Genbank Accession No. AF241535), which is particularly active in pancreatic cancer cells (Perrais et al., 2001, published on Jun. 19, 2001 by J Biol. Chem., "JBC Papers in Press" as Manuscript M104204200).

Suitable expression vectors include virus-based vectors and non-virus based DNA or RNA delivery systems. Examples of appropriate virus-based gene transfer vectors include, but are not limited to, those derived from retroviruses, for example Moloney murine leulcemia-virus based vectors such as LX, LNSX, LNCX or LXSN (Miller and Rosman, 1989, Biotechniques 7:980-989); lentiviruses, for example human immunodeficiency virus ("HIV"), feline leukemia virus ("FIV") or equine infectious anemia virus ("EIAV")-based vectors (Case et al., 1999, Proc. Natl. Acad. Sci. U.S.A. 96: 22988-2993; Curran et al., 2000, Molecular Ther. 1:31-38; Olsen, 1998, Gene Ther. 5:1481-1487; U.S. Pat. Nos. 6,255,071 and 6,025,192); adenoviruses (Zhang, 1999, Cancer Gene Ther. 6(2):113-138; Connelly, 1999, Curr. Opin. Mol. Ther. 1(5):565-572; Stratford-Perricaudet, 1990, Human Gene Ther. 1:241-256; Rosenfeld, 1991, Science 252:431-434; Wang et al., 1991, Adv. Exp. Med. Biol. 309:61-66; Jaffe et al., 1992, Nat. Gen. 1:372-378; Quantin et al., 1992, Proc. Natl. Acad. Sci. U.S.A. 89:2581-2584; Rosenfeld et al., 1992, Cell 68:143-155; Mastrangeli et al., 1993, J. Clin. Invest. 91:225-234; Ragot et al., 1993, Nature 361:647-650; Hayaski et al., 1994, J. Biol. Chem. 269: 23872-23875; Bett et al., 1994, Proc. Nati. Acad. Sci. U.S.A. 91:8802-8806), for example Ad5/CMV-based E1-deleted vectors (Li et al., 1993, Human Gene Ther. 4:403-409); adeno-associated viruses, for example pSub201-based AAV2-derived vectors (Walsh et al., 1992, Proc. Natl. Acad. Sci. U.S.A. 89:7257-7261); herpes simplex viruses, for example vectors based on HSV-1 (Geller and Freese, 1990, Proc. Natl. Acad. Sci. U.S.A. 87:1149-1153); baculoviruses, for example AcMNPV-based vectors (Boyce and Bucher, 1996, Proc. Natl. Acad. Sci. U.S.A. 93:2348-2352); SV40, for example SVluc (Strayer and Milano, 1996,Gene Ther. 3:581-587); Epstein-Barr viruses, for example EBV-based replicon vectors (Hambor et al., 1988, Proc. Natl. Acad. Sci. U.S.A. 85:4010-4014); alphaviruses, for example Semliki Forest virus- or Sindbis virus-based vectors (Polo et al., 1999, Proc. Natl. Acad. Sci. U.S.A. 96:4598-4603); vaccinia viruses, for example modified vaccinia virus (MVA)-based vectors (Sutter and Moss, 1992, Proc. Natl. Acad. Sci. U.S.A. 89:10847-10851) or any other class of viruses that can efficiently transduce human tumor cells and that can accommodate the nucleic acid sequences required for therapeutic efficacy.

Non-limiting examples of non-virus-based delivery systems which may be used according to the invention include, but are not limited to, so-called naked nucleic acids (Wolff et al., 1990, Science 247:1465-1468), nucleic acids encapsulated in liposomes (Nicolau et al., 1987, Methods in Enzymology 1987:157-176), nucleic acid/lipid complexes (Legendre and Szoka, 1992, Pharmaceutical Research 9:1235-1242), and nucleic acid/protein complexes (Wu and Wu, 1991, Biother. 3:87-95).

MDA-7 may also be produced by yeast or bacterial expression systems. For example, bacterial expression may be achieved using plasmids such as pCEP4 (Invitrogen, San Diego, Calif.), pMAMneo (Clontech, Palo Alto, Calif.; see below), pcDNA3.1 (Invitrogen, San Diego, Calif.), etc.

Depending on the expression system used, nucleic acid may be introduced by any standard technique, including transfection, transduction, electroporation, bioballistics, microinjection, etc.

In preferred, non-limiting embodiments of the invention, the expression vector is an E1-deleted human adenovirus vector of serotype 5. To prepare such a vector, an expression cassette comprising a transcriptional promoter element operatively linked to an MDA-7 coding region and a polyadenylation signal sequence may be inserted into the multiple cloning region of an adenovirus vector shuttle plasmid, for example pXCJL.1 (Berkner, 1988, Biotechniques 6:616-624). In the context of this plasmid, the expression cassette may be inserted into the DNA sequence homologous to the 5' end of the genome of the human serotype 5 adenovirus, disrupting the adenovirus E1 gene region. Transfection of this shuttle plasmid into the E1-transcomplementing 293 cell line (Graham et al., 1977, J. General Virology 36:59-74), or another suitable cell line known in the art, in combination with either an adenovirus vector helper plasmid such as pJM17 (Berkner, 1988, Biotechniques 6:616-624; McGrory et al., 1988, Virology 163:614-617) or pBHG10 (Bett et al., 1994, Proc. Natl. Acad. Sci. U.S.A. 91: 8802-8806) or a ClaI-digested fragment isolated from the adenovirus 5 genome (Berkner, 1988, Biotechniques 6:616-624), allows recombination to occur between homologous adenovirus sequences contained in the adenovirus shuttle plasmid and either the helper plasmid or the adenovirus genomic fragment. This recombination event gives rise to a recombinant adenovirus genome in which the cassette for the expression of the foreign gene has been inserted in place of a fimctional E1 gene. When transcomplemented by the protein products of the human adenovirus type 5 E1 gene (for example, as expressed in 293 cells), these recombinant adenovirus vector genomes can replicate and be packaged into fully-infectious adenovirus particles. The recombinant vector can then be isolated from contaminating virus particles by one or more rounds of plaque purification (Berlmer, 1988, Biotechniques 6:616-624), and the vector can be further purified and concentrated by density ultracentrifugation.

In a specific, non-limiting embodiment of the invention, an mda-7 nucleic acid, in expressible form, may be inserted into the modified Ad expression vector pAd.CMV (Falck-Pedersen et al., 1994, Mol. Pharmacol. 45:684-689).

This vector contains, in order, the first 355 base pairs from the left end of the adenovirus genome, the cytomegalovirus immediate early promoter, DNA encoding splice donor and acceptor sites, a cloning site for the mda-7 gene, DNA encoding a polyadenylation signal sequence from the β globin gene, and approximately three kilobase pairs of adenovirus sequence extending from within the E1B coding region. This construct may then be introduced into 293 cells (Graham et al., 1977, J. Gen. Virol. 36:59-72) together with plasmid JM17 (above), such that, as explained above, homologous recombination can generate a replication defective adenovirus containing MDA-7 encoding nucleic acid. FIG. 2A shows the mda-7 gene, inserted into the pAd.CMV vector, forming pCMV/mda-7; FIG. 2B shows the recombination event (curved lines) between the JM17 plasmid and pCMV/mda-7; and FIG. 2C shows the resulting Ad.mda-7 replication defective adenovirus.

In another specific, non-limiting embodiment of the invention, where mda-7 is to be introduced into cells in culture, a suitable expression vector may be prepared by inserting an mda-7 nucleic acid, extending from nucleotide 176 to nucleotide 960 in the sequence presented as SEQ ID NO:1, encoding the open reading frame, into pCEP4 (Invitrogen, San Diego, Calif.) downstream of the CMV promoter. Another suitable vector may be the Rous sarcoma virus ("RSV") vector available as pREP4 (Invitrogen).

In alternative embodiments, the amount of MDA-7 encoding mRNA may be increased by increasing expression of the mda-7 gene endogenous to the cancer cells. For example, such increased expression may be induced by exposing the cells to one or more differentiation-promoting agent. As one non-limiting specific example, the cancer cells may be exposed to effective concentrations of IFN-β and mezerein (see, for example, Jiang and Fisher, 1993, Mol. Cell. Different. 1(3):285-299, which exposed cells, in culture, to 2000 units/ml of IFN-β and 10 ng/ml of mezerein). Alternatively, the cancer cells may be exposed to an effective amount of a small molecule identified as set forth in Section 5.4.

In further embodiments, the amount of MDA-7 in a cancer cell and/or within a population of cancer cells may be increased by introducing MDA-7 protein into the cell and/or population. For example, for introduction into a cell, MDA-7 protein could be incorporated into a microparticle for uptake by pinocytosis or phagocytosis. MDA-7 protein may be introduced into a population such that it is present in the extracellular environment of the cells; there is evidence that MDA-7 is a secreted protein and, as such, may be biologically active in the extracellular context; support for biological activity of extracellularly administered MDA-7 is presented in Section 8, below. For embodiments in which MDA-7 protein is introduced into a cell or population of cells, MDA-7 may be comprised, for example, in microparticles, liposomes, or other protein-stabilizing formulations known in the art.

5.2. Compositions that Decrease RAS Activity

The second component necessary for practicing the methods of the invention is a means for decreasing RAS activity in a cancer cell and/or within a population of cancer cells. This decrease in activity may be achieved through either genetic means (e.g. the application of antisense, triplex or ribozyme technologies to decrease the transcription or translation of the ras gene or its message, or to decrease the transcription or translation of another molecule or molecules within the RAS pathway), or through pharmacological means (e.g. the use of small molecular inhibitors of the RAS pathway or the use of farnesyl transferase inhibitors to impair the association of RAS with the cell membrane).

The term "RAS" as used herein refers to members of the RAS family of proteins, including the proteins human H-RAS, K-RAS, and N-RAS and the corresponding genes H-ras, K-ras and N-ras, having sequences as set forth in Genbank Accession No. J00277, Genbank Accession No. M54968 and Genbank Accession No. XM 001317, respectively, incorporated by reference herein, as well as mutant forms. The nucleic acid sequence of wild-type K-ras and its encoded amino acid sequence are set forth as SEQ ID NOS: 6 and 7, respectively. The mutant forms of RAS include those having point mutations at amino acid residues 12, 13, 18 and/or 61. Accordingly, the RAS proteins encompassed by the present invention comprise the aforementioned amino acid sequences and those sequences having any amino acid substituted at position 12, 13, 18, and/or 61. The scope of the invention also includes nucleic acids encoding said amino acid sequences. SEQ ID NOS: 8-11 are amino acid sequences of K-RAS having single amino acid substitutions at each of these positions, where Xaa can represent any amino acid. In specific non-limiting embodiments, the amino acid at position 12 of K-ras may be substituted with aspartic acid (Xaa=Asp), glycine (Xaa=Gly), valine (Xaa=Val), or arginine (Xaa=Arg).

The term "ras" also applies, with regard to nucleic acids (including RNA and DNA molecules), to nucleic acid molecules which hybridize to a nucleic acid sequence as set forth in Genbank Accession number J00277, SEQ ID NO:6, or Genebank Accession No. XM 001317, under stringent hybridization conditions e.g., hybridization in 0.5 M $NaHPO_4$, 7 percent sodium dodecyl sulfate ("SDS"), 1 mM ethylenediamine tetraacetic acid ("EDTA") at 65° C., and washing in 0.1×SSC/0.1 percent SDS at 68° C. (Ausubel et al., 1989, Current Protocols in Molecular Biology, Vol. I, Green Publishing Associates, Inc., and John Wiley & Sons, Inc. New York, at p. 2.10.3) and to proteins which they encode. The present invention provides for the coding strand nucleic acid molecule, as well as its complementary (antisense strand), and oligonucleotide portions thereof. Oligonucleotides may preferably be 5-50 bases or base-pairs in length.

The aforedescribed ras nucleic acid molecules (including oligonucleotides) may be comprised in larger nucleic acid molecules, for example appropriate vector molecules, wherein they may be in "expressible form" as defined above. Further, the nucleic acid molecules encompassed herein may be altered to comprise non-naturally occurring nucleic acids or have stabilized (nuclease resistant) linkages.

Examples of modified base moieties which may be used include, but are not limited to, 5-fluorouracil, 5-bromouracil, 5-chlorouracil, 5-iodouracil, hypoxanthine, xanthine, 4-acetylcytosine, 5-carboxyhydroxymethyluracil, 5-carboxymethylaminomethyl-2-thiouridine, 5-carboxymethylaminomethyluracil, dihydrouracil, βgalactosylqueosine, inosine, N6-isopentyladenine, 1-methylguanine, 1-methylinosine, 2,2-dimethylguanine, 2-methyladenine, 2-methylguanine, 3-methyl cytosine, 5-methyl cytosine, N6-adenine,7 methylguanine, 5-methylaminomethyluracil, β-methoxyaminomethyl-2-thiouracil, 3-D-mannosylqueosine, 5'-methoxycarboxymethyluracil, 5-methoxyuracil, 2-methylthio-N6-isopentyladenine, uracil-5-oxyacetic acid (v), wybutoxosine, pseudouracil, queosine, 2-thiocytosine, 5-methyl-2-thioruracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl)uracil, (acp3)w, and 2,6-diaminopurine.

One preferred non-limiting example of a modified linkage is a phosphorothioate intemucleoside linkage, e.g. as described in U.S. Pat. No. 6,242,589 by Cook and Manoharab, issued Jun. 5, 2001. Other nucleoside linkages resistant to nuclease digestion include phosphotriester, methyl phosphonate, short chain alkyl or cycloalkyl intersugar linkages or short chain heteroatomic or heterocyclic intersugar linkages (see U.S. Pat. No. 6,229,006 by Wu, issued May 8, 2001). Peptide nucleic acids may also be used, as described, for example, in U.S. Pat. No. 5,539,082 by Nielsen et al., issued Jul. 23, 1996; U.S. Pat. No. 5,714,331 by Buchardt et al., issued Feb. 3, 1998; U.S. Pat. No. 5,719,262 by Buchardt et al., issued Feb. 11, 1998, and in Nielsen et al., 1991, Science 254:1497-1500.

The phrase "a decrease in RAS activity", as used herein, indicates a decrease in the amount or proportion of one or more species of molecule within the RAS pathway which is (are) in an activated state. A simplified diagram of the RAS pathway, showing certain (but not all) molecules upstream and downstream of RAS which may reflect RAS activity according to the invention, is presented in FIG. 1. For certain members of the RAS pathway, an active state is reflected by phosphorylation. The "decrease" is relative to the amount or proportion of activated molecules in a cell or population of cells which has (have) not been treated according to the invention. As one specific, non-limiting example, RAS protein is in an active state when it is bound to GTP. Where the invention produces a decrease in proportion of RAS molecules in the active state, there has been a decrease in RAS activity.

Other molecules in the RAS pathway which can reflect and/or can be inhibited to produce a "decrease in RAS activity" as defined herein include, but are not limited to, the EGF receptor, RAF1 ("RAF"), PI3 kinase, MAPK kinase, MAP kinase ("MAPK"), MEKK1, and the MAPK proteins ERK1 and ERK2. As one specific non-limiting example, a decrease in RAS activity may be reflected by a decrease in phosphorylation of MAPK kinase, wherein the active form of that molecule is phosphorylated, and RAS activity as defined herein may be decreased by inhibiting MAPK kinase. The "decrease in RAS activity" may also be reflected by the decrease in activation of an as yet unidentified or unconfirmed RAS effector molecule. This document incorporates the definition of a RAS effector molecule articulated in Crespo and León, 2000, Cell. Mol. Life Sci. 57:1613-1636, which states that a RAS effector molecule exhibits "(1) preferential binding to the GTP-bound form of RAS, (2) binding to a region within the effector domain, this binding eliciting the activation of the effector molecule with a subsequent biochemical and/or biological effect, and (3) dysfunction of the putative effector molecule abolishes at least part of the RAS-mediated effects".

In preferred embodiments, RAS activity may be decreased by inhibiting RAS protein synthesis using antisense technology. "Antisense ras" molecules may be used to interfere with ras RNA function at various stages, including splicing, catalytic activity, translocation of RNA to the site of protein translation, and/or translation of protein from the RNA (see, for example, U.S. Pat. No. 6,255,111 by Bennett et al., issued Jul. 3, 2001, which provides a review of antisense techniques and materials). According to the present invention, the translation of ras-specific messenger RNA (mRNA) may be blocked through the introduction into cells of synthetic nucleic acid sequences that are complementary to all or part of the endogenous gene. These synthetic nucleotide sequences interact with endogenous mRNA sequences based on their sequence compleinentarity, forming double-stranded RNA species that are less able to be translated into protein species and more prone to degradation by the enzyme RNaseH than single-stranded RNA. This approach, or variants thereof, have been shown to be successful in inhibiting proliferation of a number of human cancer cell lines in vitro (Aoki et al., 1997, Molecular Carcinogenesis 20:251-258; Kita et al., 1999, Intl. Journal of Cancer 80:553-558) and suppressing the growth of human tumors in vivo in animal models (Nakano et al., 2001, Molecular Ther. 3:491499).

An antisense molecule may be designed to target ras mRNA, for example, in the region encompassing the translation initiation or termination codon of the open reading frame. In preferred embodiments, the antisense molecule is an oligonucleotide between about 6 and 50 bases in length, and complementary to a portion of ras mRNA such that hybridization with the antisense oligonucleotide inhibits or prevents translation to form RAS protein. In specific, non-limiting embodiments an antisense oligonucleotide hybridizes to a wild-type or mutated ras nucleic acid under stringent conditions, as defined above. Although antisense oligonucleotides complementary to the 5' end of ras mRNA, for example the 5' untranslated sequence up to and including the AUG initiation codon, are preferred, oligonucleotides complementary to the 3' untranslated sequences or, less preferably, the coding regions of ras mRNA, may also be used. Where ras contains a point mutation, mutation-specific oligonucleotides may be employed, as such oligonucleotides may selectively inhibit expression of the mutated, but not the wild type, ras gene.

Specific, non-limiting examples of viral vectors that encode antisense ras nucleic acids are known in the art (e.g., AS-K-ras-LNSX (Aoki et al., 1995, Cancer Res. 55:3810-3816); $A_xCA$-AS-K-ras (Nakano et al., 2001, Mol. Ther. 3(4):491499)). In specific, non-limiting embodiments of the invention, a replication defective adenovirus vector encoding antisense ras may be used. Such vectors may be prepared using methods analogous to those used to prepare Ad.mda-7. FIGS. 3A-C show the preparation of one specific example of such a vector, in which a 631 nucleotide sequence representing nucleotides 172 to 802 of K-ras, in antisense orientation, is inserted in pAd.CMV to form pCMV/K-ras AS (FIG. 3A). Homologous recombination with pJM17 in 293 cells (FIG. 3B) may be used to generate replication defective Ad.K-ras AS virus (FIG. 3C). The effectiveness of an adenovirus vector encoding antisense ras sequences, used together with Ad.mda-7, is demonstrated by data presented in Section 9, below. In another specific embodiment, a pcDNA3.1 (neomycin resistance) expression vector containing a 346 nucleotide K-ras gene fragment (from nt 172 to 517), as described below in Section 6, may be used.

Specific, non-limiting examples of antisense ras oligonucleotides are known in the art, for example the following phosphorothioate antisense oligonucleotides targeting mutations at codon 12 of K-ras (mutant specific sequence underlined):

(SEQ ID NO:12)
for mutation to GTT, 5'-CTACGCC<u>AAC</u>AGCTCCA-3';

(SEQ ID NO:13)
for mutation to CGT, 5'-CTACGCC<u>ACG</u>AGCTCCA-3'; and (SEQ ID NO:14)
for mutation to GAT, 5'-CTACGCC<u>ATC</u>AGCTCCA-3'

(Kita et al., 1999, Int. J. Cancer <u>80</u>: 553-558).

In a preferred specific embodiment, the phophorothioate oligonucleotide 5'-CACAAGTTTATATTCAGT-3' (SEQ ID NO:15), complementary to K-ras nucleotides 196-213 (adjacent to the start codon), as described below in Section 6, or an oligonucleotide comprising SEQ ID NO:15 or hybridizable to the complement of SEQ ID NO:15 under stringent conditions, may be used.

A vector containing sequence expressible to form antisense ras nucleic acid may be introduced into a cancer celucancer cell population by methods known in the art, such as infection, transfection, electroporation, etc.

Antisense ras oligonucleotides may be introduced into a cancer cell/cancer cell population by methods known in the art, which may utilize, for example, liposomes (e.g. DC-cholesterol liposomes, cationic liposomes, liposomes containing Sendai virus coat protein), imidazolium lipids (see, for example, U.S. Pat. No. 6,245,520 by Wang et al., issued Jun. 12, 2001), cationic lipids (see, for example, U.S. Pat. No. 6,235,310 by Wang et al., issued May 22, 2001), lipofection, asialoglycoprotein poly(L)lysine complexes, and microbubbles (see, for example, U.S. Pat. No. 6,245,747 by Porter et al., issued Jun. 12, 2001). See, for example, the experiments described in Section 6, below, where lipofectamine was used to promote oligonucleotide uptake.

In particular, non-limiting embodiments of the invention, a single vector may be used for the introduction of both an MDA-7-encoding nucleic acid and antisense ras sequences. For example, but not by way of limitation, an expressible form of mda-7 nucleic acid and ras antisense encoding nucleic acid sequences, operatively linked to the same promoter, to two promoters which are the same, or to two promoters which are different, may be incorporated into an E1-deleted human adenovirus vector of serotype 5, via, for example, pAd.CMV, as described above. FIG. 4 presents a diagram showing the preparation of such a vector. Briefly, HEK-293 cells may be transfected with overlapping DNA fragments from the viral genome of Ad.mda-7 and from plasmid pPF446 (Volker and Young, 1983, Virol. 125:175-193) modified to contain the K-ras sequence, cloned in an antisense orientation, in the E3 region. Recombination (shown by a curved line) between the two fragments generates a genome containing both mda-7 and AS K-ras sequences.

In other non-limiting embodiments, ribozymes may be used to decrease RAS activity. Ribozymes are enzymatic RNA molecules which catalyze the specific cleavage of RNA. Ribozyme molecules according to the invention comprise a region complementary to ras mRNA where the region is capable of specifically hybridizing to r as mRNA, and may have a hairpin or hammerhead structure (Rossi, 1994, Current Biology 4:469-471; U.S. Pat. No. 5,093,246 by Cech et al., issued Mar. 3, 1992; Haseloff and Gerlach, 1988, Nature 334:585-591; Zaug et al., 1984, Science 224:574-578; Zaug and Cech, 1986, Science 231:470-475; Zaug et al., 1986, 324:429-433; Been and Cech, 1986, Cell 47:207-216).

In further embodiments, ras gene transcription may be blocked by targeted deoxyribonucleotide sequences complementary to the ras gene regulatory region which produce triple helical structures that prevent transcription (Helene, 1991, Anticancer Drug. Des. 6(6):569-584; Helene et al., 1992, Ann. N.Y. Acad. Sci. 660:27-36; Maher, 1992, Bioassays 14(12):807-815).

In further embodiments, RAS activity may be decreased by introducing, into a cancer cell, a dominant negative ras mutant (e.g., the H-ras mutant N116Y; Shichinohe, 1996, J. Surg. Res. 66:125-130).

In further embodiments of the invention, RAS activity may be decreased by administering an effective amount of a small molecule which may be identified using the methods set forth in Section 5.4, below.

In additional embodiments of the invention, RAS activity may be decreased by a farnesyl transferase inhibitor. In order to become activated through GTP binding, the cytosolic form of RAS must be localized to the inner surface of the cell membrane. This process is regulated by at least three types of post-translational modification which are performed on the RAS protein. One of these is the process of farnesylation, whereby a fatty acid farnesyl moiety is enzymatically attached to the cysteine residue in the CAAX motif located near the C-terminus of the protein. Inhibition of this reaction, which is catalyzed by the enzyme farnesyl transferase (FT), can drastically reduce RAS activation and block RAS-mediated transformation (Kohl et al., 1993, Science 260:1934-1937; Kohl et al., 1994, Proc. Natl. Acad. Sci. U.S.A.91:9141-9145). FT inhibitors fall into several classes. The first are those competing with the farnesyl moiety. These compounds include limonene, perillyl alcohol and perillic acid among others (reviewed in Hardcastle et al., 1999, Biochem. Phann. 57:801-809). A second class includes agents that mimic the CAAX motif present in the RAS protein. These agents are referred to as peptidomimetics and include FT1-276 (Lantry et al., 2000, Carcinogenesis 2:113-116), FTI-277 (Adjei et al., 2000, Clin Can Res 6:2318-2325), and L-739,749 (Lebowitz et al., 1995, Mol Cell Biol 15:6613-6622) among other compounds. The third class is comprised of compounds that combine the characteristics of both aforementioned groups, and are referred to as bisubstrate inhibitors. Compounds in this class include BMS-1 86511 (Schlitzer and Sattler, 2000, Eur J Med Chem 2000;35:721-726). RAS activity may be decreased by administering an effective amount of any of the foregoing compounds or other farnesyl transferase inhibitors known in the art. Such compounds may be administered orally, intravenously or by intratumoral injection among other routes.

5.3. Assays to Identify Suitable Target Cells

A "target cell" is defined herein as a cancer cell which, when subjected to the methods of the invention, is expected to exhibit inhibited proliferative ability and/or characteristics of programmed cell death ("apoptosis").

In specific, preferred non-limiting embodiments of the invention, the present invention is directed toward inhibiting the proliferation and survival of pancreatic cancer cells. Experimental data presented in Section 6, below, indicate that the synergistic effect of MDA-7 and ras antisense molecules is observed in pancreatic cancer cells having a mutation activated ras gene, but not in cells having wild type ras. It therefore is desirable, although not required, to ascertain whether RAS activity is increased in a pancreatic cancer cell before applying the methods of the invention.

As the methods of the invention may be directed toward cancer cells which have origins other than the pancreas, this section provides guidelines for identifying suitable target cells. Suitable non-pancreatic cancer target cells exhibit increased RAS activity, and may be identified, for example, as having a mutation in a ras gene. For example, but not by way of limitation, cancers which have been associated with a ras gene mutation which increases RAS activity include malignant melanoma (Demunter et al., 2001, Cancer Res. 61:4916-4922), gastric cancer (Hao et al., 1998, J. Tongji Med. Univ. 18(3):141-144), gallbladder carcinoma (Kim et al., 2001, Cancer Lett. 169(1):59-68), colon carcinoma (Clarke et al., 2001, Int. J. Colorectal Dis. 16(2):108-111), lung cancer, particularly non-small cell lung cancer (Noda et al., 2001, Oncol. Rep. 8(4):889-92), acute lymphoblastic leukemia (Nakao et al., 2000, Leukemia 14(2):312-315), hepatocellular carcinoma (Weihrauch et al., 2001, Br. J. Cancer 84(7):982-989), liver angiosarcoma (Marion et al., 1991, Mol. Carcinog. 4(6):450-454); multiple myeloma (Tanaka et al., 1992, Int. J. Hematol. 56(2):119-127), bladder carcinoma (Saito et al., 1997, Int. J. Urol. 4(2):178-185), peripheral nerve sheath tumors (Watanabe et al., 2000, Int. J. Mol. Med. 5(6):605-608), childhood brain tumors (Maltzman et al., 1997, Cancer Epidemio. Biomarkers Prev. 6(4): 239-243), ovarian tumors (Varras et al., 1999, Oncology 56(2):89-96), cervical carcinoma (Grendys et al., 1997, Gynecol. Oncol. 65(2):343-347), thyroid carcinoma (Basolo et al., 2000, Thyroid 10(1):19-23), chondrosarcoma (Sakamoto et al., 2001, Mod. Pathol. 14(4):343-349), and primary sarcoma of the heart (Garcia et al., 2000, Br. J. Cancer 82(6):1183-1185). Miyakis et al. (1998, Biochem. Biophys. Res. Commun. 251(2):609-612) reports a low incidence of ras point mutation in breast cancer subjects, but observed overexpression of ras in 67 percent of breast cancer specimens studied.

The presence of a ras mutation in a cancer cell, for example a cancer cell collected from a human subject, may be determined using standard laboratory techniques, such as, for example, PCR-Restriction Fragment Length Polymorphism ("PCR-RFLP") analysis, PCR-Single Strand Conformational Polymorphism ("PCR-SSCP") analysis, LightCycler technology (analysis of melting temperatures of PCR products; see Nakao et al., 2000, Leukemia 14(2):312-315); fluorescent oligonucleotide ligation (Eggerding, 2000, Mol. Biotechnol. 14(3):223-233); PCR/dot blot hybridization (Grendys et al., 1997, Gynecol. Oncol. 65(2):343-347), PCR/restriction enzyme treatment/dot blot hybridization (Saito et al., 1997, Int. J. Urol. 4(2): 178-185), PCR-primer introduced restriction with enrichment of mutant alleles ("PCR-PIREMA" assay; Basolo et al., 2000, Thyroid 10(1): 19-23) and/or DNA sequencing.

Overexpression of ras may be determined using standard techniques, including Northern blot analysis and RT-PCR (Miyakis et al., 1998, Biochem. Biophys. Res. Commun. 251(2):609-612).

Where a representative cell line for a cancer cell is available, it may further be desirable to increase MDA-7 and decrease RAS activity in a culture of said cell line, for example using techniques as described for the pancreatic carcinoma cell lines set forth in Section 6, below. Suitability of the cancer cell as a target cell would be indicated by a decrease in cell proliferation, a decrease in colony formation in soft agar, an increase in cell death (e.g., apoptotic cell death), and/or a decrease in tumorigenicity (e.g., in nude mice). For example, apoptotic cell death may be measured by methods known in the art, for example the TUNEL method, as described in Gravieli et al., 1992, J. Cell Biol. 119:493-501. In specific non-limiting embodiments of the invention, an increase in apoptosis may be indicated by an increase in the level of BAXprotein and/or a decrease in BCL-2 protein; for example, preferably, BAX may increase at least about 3-fold, and/or BCL-2 may be reduced at least 1.2-fold, and/or the BAX/BCL-2 ratio may increase by at least about 2-fold (Madireddi et al., 2000, Adv. Exptl. Med. Biol. 465:239-261; Su et al., 1998, Proc. Nat. Acad. Sci. U.S.A. 95:14400-14405; Saeki et al., 2000, Gene Ther. 7:2051-2057).

In particular embodiments, the present invention provides for a method for identifying a suitable cancer cell for treatment with mda-7/anti-RAS combination therapy, comprising (i) administering, to a test cancer cell, a first agent which increases the amount of MDA-7 protein in combination with a second agent that decreases RAS activity in the cancer cell; (ii) determining whether the cancer cell exhibits at least one characteristic of apoptosis; wherein the presence of a characteristic of apoptosis has a positive correlation with the suitability of the cancer cell for treatment with mda-7/anti-RAS combination therapy.

In other particular embodiments, the present invention provides for a method for identifying a suitable cancer cell for treatment with mda-7/anti-RAS combination therapy, comprising (i) administering, to a culture of test cancer cells, a first agent which increases the amount of MDA-7 protein in combination with a second agent that decreases RAS activity; (ii) measuring the proliferation of cancer cells in the culture; and (iii) comparing the proliferation of cells measured in step (ii) with the proliferation of control cultures of the cancer cells in the presence of the same concentration of first agent or second agent, used alone; wherein if the combination of first and second agent results in a decrease in cell proliferation which is greater than the additive effect of the first agent and the second agent used alone, the cancer cell is suitable for treatment with mda-7/anti-RAS combination therapy.

5.4. Assays to Identify Anti-cancer Small Molecules

The present invention further provides for methods of identifying small molecules that may be effective in the treatment of cancers exhibiting an increase in RAS activity.

In particular non-limiting embodiments, compounds that decrease RAS activity could be identified by the following method. A mda-7 gene, in expressible form (e.g., Ad.mda-7), could be introduced into a cancer cell line having increased RAS activity (e.g., a pancreatic cancer cell line having an activating mutation in K-ras) to form a population of "test cells". The level of MDA-7 RNA or protein (or the absence of detectable MDA-7) in the test cells may be determined, and then the test cells may be exposed to various chemical or biochemical compounds, for example a combinatorial library of small molecules (also referred to herein as small molecules having a defined structure), by the addition of one or more compound to the culture media of parallel cultures of test cells. The appearance of MDA-7-encoding RNA or protein, or an increase in MDA-7-encoding RNA or protein, within the test cells and/or in the culture media would suggest that a chemical being tested may have decreased RAS activity in the test cells. Without being bound by any particular theory, this conclusion would be supported by the observation that activation of K-ras appears to interfere with the ability of the mda-7 RNA to be translated into MDA-7 protein (see Section 6, below). A chemical positively identified through this assay procedure may then be further tested for its ability to decrease RAS activity and/or to inhibit the proliferation and/or survival of cancer cells. Further, such a chemical may be characterized to better define the mechanism whereby they exert their effects on activated K-ras.

Alternatively, pancreatic cancer cells or immortalized cell lines exhibiting an increase in RAS activity (e.g., as a result of a ras mutation) may be treated with compounds known to decrease RAS activity (e.g., antisense ras molecules, to produce a population of test cells. The level of MDA-7 (if any is detectable)-encoding RNA or protein in the test cells may be determined. The test cells then may be exposed to various chemical or biochemical compounds, for example a combinatorial library of small molecules, by the addition of one or more compound to the culture media of parallel cultures of test cells. The appearance of MDA-7-encoding RNA or protein, or an increase in MDA-7-encoding RNA or protein, within the test cells and/or in the culture media would suggest that a chemical being tested may have enhanced the activity of MDA-7 in the test cells. Alternatively or in addition, biological endpoints such as growth suppression or apoptosis may be used in the screening procedure. A chemical positively identified through this assay procedure may then be further characterized to determine its anti-cancer potential and/or to better define the mechanism whereby it exerts its effect on these cellular processes.

5.5. Methods of Use

The present invention relates to methods for inhibiting proliferation and inducing cell death in a population of cancer cells by (i) increasing the amount of the differentiation associated protein, MDA-7 and (ii) decreasing RAS activity within the population. A "population" is defined herein as comprising at least two cells. Non-limiting examples of populations include a solid tumor, an infiltrating tumor, cancer cells disseminated within a subject (e.g., as would be present in a subject with metastatic disease), and a cell culture. To practice the full scope of the invention, the amount of MDA-7 may be increased intracellularly and/or extracellularly and an increase in MDA-7 protein and/or a decrease in RAS activity need not be achieved in all the cells of the population.

In particular embodiments, the present invention relates to methods for inhibiting proliferation and/or inducing cell death of a cancer cell by (i) increasing the amount of the differentiation associated protein, MDA-7 and (ii) decreasing RAS activity in the cancer cell.

The cancer cell in the foregoing methods may be a pancreatic cancer cell or other suitable target cell, as described in the foregoing section.

The amount of MDA-7 may be increased by introducing, into a cancer cell, a nucleic acid encoding mda-7 in expressible form, or by administering, to the cancer cell and/or to the population of cancer cells, MDA-7 protein, as set forth in section 5.1, above, such that an amount of MDA-7 protein is present which is effective, in the presence of decreased RAS activity, in decreasing cell proliferation and inducing cell death.

For example, and not by way of limitation, where mda-7 is to be introduced into a cancer cell via a viral vector, the amount of virus to which the cell is exposed may be between about 1-1000 pfu/cell, and preferably between about 100-250 pfu/cell. In the working example set forth in Section 6, below, 100 pfu/cell of mda-7 comprised in a replication defective adenovirus vector was used.

Where MDA-7 protein is to be administered to a cell, in specific non-limiting embodiments of the invention, the concentration of MDA-7 to which the cell is exposed may be between about 1-100 ng/ml.

The amount of RAS activity may be decreased by administering, to the cancer cell or cancer cell population, an effective amount of an anti-RAS agent, which may be, for example, an antisense molecule, a ribozyme, a precursor of a triple helix, a small molecule with a defined structure (see Section 5.4, above) or a farnesyl transferase inhibitor or an agent that acts at some other point of the RAS pathway, for example, but not limited to, an antagonist of the EGF receptor or an inhibitor of RAF, MAPK kinase, or PI3 kinase. In preferred embodiments of the invention, an antisense molecule, particularly an antisense oligonucleotide, and most preferably an antisense oligonucleotide having phosphorothioate linkages is used. In particular embodiments, where a specific mutation of ras in the cancer cell to be treated has been identified, a mutation specific oligonucleotide may be used.

In preferred non-limiting embodiments of the invention, a phosphorothioate antisense oligonucleotide 5'-CACAAGTTTATATTCAGT-3' (SEQ ID NO:15), or an oligonucleotide comprising said nucleotide or hybridizable to the complement of said nucleotide under stringent conditions, may be used.

In specific, non-limiting embodiments, the concentration of oligonucleotide to which a cancer cell is exposed may be between about 0.1-10 micromolar and preferably between about 0.25-0.75 micromolar. In the experiments described in Section 6, below, a concentration range of 0.1-5.0 micromolar was used.

An "effective amount" of a combination of agents that increase MDA-7 and decrease RAS activity is an amount of agents which result in a decrease in cancer cell proliferation and an increase in cancer cell death. The amount of each agent may not, and probably is not, effective in the absence of the other. Preferably, but not by way of limitation, the decrease in cell proliferation is by at least 25 percent, and the increase in cell death is by at least about 25 percent, relative to a control cancer cell not exposed to either agent.

The present invention and the foregoing methods may be applied to the treatment of a subject with a cancer. The subject may be a human or a non-human mammalian subject, and the cancer may be comprised of pancreatic cancer cells or other suitable target cells, as defined in the foregoing section. In particular non-limiting embodiments, the present invention provides for a method for treating a subject having pancreatic cancer, comprising, administering, to the subject, amounts of agents which are effective, in combination, in (i) increasing the amount of the differentiation associated protein, MDA-7 and (ii) decreasing RAS activity in cells of the pancreatic cancer. In specific non-limiting embodiments, the subject having pancreatic cancer is treated by administering, to the subject, (a) a viral vector comprising an mda-7 gene in expressible form; and (b) an antisense ras oligonucleotide, in amounts which are effective, in combination, in (i) increasing the amount of the differentiation associated protein, MDA-7 and (ii) decreasing RAS activity in cells of the pancreatic cancer.

The subject may be administered a therapeutically effective amount of a combination of MDA-7 increasing and RAS activity decreasing agents by a suitable route, including intra-tumor instillation, intravenous, intraarterial, intrathecal, intramuscular, intradermal, subcutaneous, etc. A therapeutically effective amount of these agents produces one or more of the following results: a decrease in tumor mass, a decrease in cancer cell number, a decrease in serum tumor marker, a decrease in tumor metastasis, a decreased rate of tumor growth, improved clinical symptoms, and/or increased patient survival. The cancer may be first treated surgically to de-bulk the tumor mass, if appropriate.

Where a viral vector is used to deliver either mda-7 and/or antisense ras-encoding nucleic acid sequences, the amount of vector administered to the subject, in preferred embodiments, is between about $10^9$ and $10^{13}$ pfu. Where a replication defective viral vector is being used to either deliver mda-7 or antisense ras encoding nucleic acid, it is preferable to deliver such vector directly into or around the cancer cells, for example, by intra-tumor injection or by instillation into the tumor bed following surgical resection Where antisense oligonucleotides are being administered, the effective dosage may vary among formulations. Optimum dosages may be determined based on the $EC_{50}s$ determined in vitro, in cell culture, and/or in vivo, in animal models. For example, but not by way of limitation, the dosage may range from 0.01 micrograms to 10 mg per kg of body weight.

The present invention also may be applied to the treatment of metastatic cancer in a subject. Metastatic cancer is defined herein as the occurrence of one or more cancer cell at a site which is not directly contiguous with a primary tumor (e.g., cancer cells from a non-lymphoid tumor in a lymph node receiving lymphatic drainage from the site of the primary tumor, cancer cells identified in the lung, brain, bone, or liver where the primary cancer does not originate in respectively lung, brain, bone or liver). The definition of "metastatic cancer" also encompasses instances where a primary tumor cannot be identified, in which case there is a histological determination that a cancer cell or group of cancer cells did not originate in the tissue where it (they) has (have) been detected.

In a subset of such embodiments, the present invention provides a means for treating metastatic cancer in a subject which addresses the issue that it may be difficult to provide a sufficient number of viral vectors carrying the mda-7 gene to achieve infection of cancer cells in distant metastases. This problem may be addressed by infecting a population of cells in the subject with an mda-7 bearing viral vector, and thereby providing distant cancer cells in the subject with MDA-7 released or secreted by the infected population. The effectiveness of such released/secreted MDA-7 at inhibiting proliferation of cancer cells is supported by data provided in Section 8, below. The distant cancer cells may be further treated by antisense ras in the form of oligonucleotides (e.g., phosphorothioate linked oligonucleotides). Non-limiting examples of end points that may be examined as a means of establishing efficacy of treatment include decreases in the number and size of metastatic tumors, decreases in their rate of growth, and/or increases in the length of survival of the subject. One skilled in the art will recognize that many other objective measures of morbidity and/or mortality also may be examined to assess therapeutic efficacy.

In particular embodiments, treatment of metastatic disease may be achieved through administering, to the subject, amounts of agents which are effective, in combination, in (i) increasing the amount of the differentiation associated protein MDA-7 in blood or other extracellular fluids and (ii) decreasing RAS activity in target cells residing in both the primary tumor site and in metastatic sites. In specific non-limiting embodiments, the subject having metastatic cancer is treated by administering, to the subject, (a) a viral vector comprising an mda-7 gene in an expressible form; and (b) an antisense ras oligonucleotide, in amounts which are effective, in combination, in (i) increasing the amount of the differentiation associated protein MDA-7 in blood or other extracellular fluids and (ii) decreasing RAS activity in cells of the both the primary tumor and metastatic tumor locations. A preferred form of this embodiment may comprise the combined administration of (i) an anti-ras phosphorothioate antisense oligonucleotide, such as that represented by SEQ ID NO: 15 or other nucleotides sequences hybridizable to the complement of said nucleotide sequence under stringent conditions, at doses capable of achieving concentrations of the oligonucleotide between 0.1 and 50 micromolar in the fluids surrounding the cancer cell and (ii) a viral vector encoding mda-7, after which the MDA-7 protein is synthesized in and released from the virally-transduced cells into the blood or other extracellular fluids so that MDA-7 concentrations of between 1 to 100 ng/ml could be attained in the fluids surrounding the target cells. In specific non-limiting embodiments of the invention, a viral vector carrying a mda-7 gene may be introduced into an identified population of cells, for example hepatocytes, or cells of the primary tumor.

In related embodiments based on the discovery that released/secreted MDA-7 has antiproliferative activity, the present invention provides for methods of treating cancer cells which are responsive to MDA-7 without requiring a decrease in RAS activity, comprising exposing said cancer cells to extracellular MDA-7 protein at a level effective in inhibiting the proliferation of said cells. Such extracellular protein may be provided by administration of protein or by introducing an mda-7 gene into cells of the subject (which may be any type or types of non-malignant or malignant cells of the subject, e.g., normal hepatocytes, fibroblasts, muscle cells, cancer cells, combinations of different cell types, etc.) such that cells release/secrete MDA-7 which may then inhibit cancer cell proliferation/survival, even at distant cites. Cancer cells susceptible to MDA-7 antiproliferative effects include, but are not limited to, melanoma cells, glioblastoma multiforme cells, osteosarcoma cells, breast cancer cells, cervical cancer cells, colon cancer cells, lung cancer cells, nasopharynx cancer cells, ovarian cancer cells, and prostate cancer cells. A growth suppressive effect of culture medium of Ad.mda-7-infected hepatocytes (providing extracellular MDA-7) on human prostate cancer cells has been observed (see Section 8, below).

The foregoing treatments may be administered in conjunction with other surgical and non-surgical therapeutic modalities, including chemotherapy, gene therapy, immunotherapy, and radiation therapy.

6. EXAMPLE

A Combinatorial Approach for Selectively Inducing Programmed Cell Death in Human Pancreatic Cancer Cells

6.1 Materials and Methods

Cell lines, culture conditions and growth assays. The AsPC-1, BXPC-3, MIA PaCa-2 and PANC-1 human pancreatic carcinoma cell lines (obtained from the American Type Culture Collection) were grown in RPMI 1640 containing 10 percent fetal bovine serum ("FBS") at 37° C. in a 95 percent air 5 percent carbon dioxide humidified incubator. Cell growth and viable cell numbers were monitored by hemocytometer and MTT staining as described in (Lebedeva et al., 2000, Cancer Res. 60:6052-6060).

Animal studies. Tumorigenicity assays were performed as described in Madireddi et al., 2000, Adv. Exptl. Med. Biol. 465:239-261 and Su et al., 1998, Proc. Natl. Acad. Sci. U.S.A. 95:14400-14405. Briefly, MIA PaCa-2 cells were untreated or infected with 100 pfu/cell of Ad.vec or Ad.mda-7 and then untransfected or transfected with an expression vector containing a 346 nt k-ras gene fragment (nt 172 to nt 517) cloned in a sense or AS orientation and $1 \times 10^6$ cells were mixed with Matrigel and injected 48 hours later subcutaneously into athymic nude mice. Animals were monitored for tumor formation and tumor volume was determined as described in Madireddi et al., 2000, Adv. Exptl. Med. Biol. 465:239-261.

Viral construction, purification and infectivity assays. The replication defective Ad.mda-7 was created in two steps. In the first step, the mda-7 gene was cloned into a modified adenovirus expression vector Ad.CMV (Falck-Pedersen et al., 1994, Mol. Pharmacol. 45:684-689). This contains, in order, the first 355 bp from the left end of the Ad genome, the cytomegalovirus irrrnediate early promoter, DNA encoding splice donor and acceptor sites, cloning sites for the insertion of the mda-7 expression cassette, DNA encoding a polyA signal sequence from the β globin gene, and approximately 3 kilobase pairs of adenovirus sequence extending from within the E1B coding region. This arrangement allows high level expression of the cloned sequence by the cytomegalovirus immediate early gene promoter, and appropriate RNA processing. In the second step, the recombinant virus was created in vivo by 293 cells (Graham et al., 1977, J. Gen. Virol. 36:59-72) by homologous recombination between the mda-7 containing vector and plasmid JM17. Following transfection of the two plasmids, infectious virus was recovered, the genomes were analyzed to confirm the recombinant structure, and then virus was plaque purified and titrated (Volkert and Young, 1983, Virology 125:175-193).

Phosphorothioate oligonucleotides. Eighteen-base phosphorothioate oligonucleotides ("PS ODN") were synthesized and purified by HPLC (Lebedeva et al., 2000, Cancer Res. 60:6052-6060). The antisense ras phosphorothioate antisense oligonucleotide ("AS K-ras PS ODN") CACAAGTTTATATTCAGT (SEQ ID NO:15) was synthesized and is complementary to wild type K-ras nucleotides 196-213 (adjacent the start codon). Based on previous studies (Sakakura et al., 1995, Anti-Cancer Drugs 6:553-561), mismatched ("MM") K-ras PS ODN CAC<u>TT</u>GC <u>AA</u>ATATTCAGT (SEQ ID NO:16) and scrambled ("SC") K-ras PS ODN ACTAGCTATACTAGCTAT (SEQ ID NO:17) to the same region (nt 196-213) were also synthesized.

RNA isolation and Northern blot analysis. Total RNA was isolated by a guanidinium/phenol procedure and Northern blots were performed as described in Jiang and Fisher, 1993, Mol. Cell. Different. 1:285-299 and Jiang et al., 1995, Oncogene 11:2477-2486.

DNA extraction fragmentation assays, FACS analysis and Annexin V, PI and DAPI staining. DNA was extracted and fragmentation assays were performed as described in Su et al., 1995, Anticancer Res. 15:1841-1848 three days after a single or combination treatment protocol. FACS analysis and annexin V and PI staining were performed using previously described methods (Su et al., 1998, Proc. Natl. Acad. Sci. U.S.A. 95:14400-14405; Lebedeva et al., 2000, Cancer Res. 60:6052-6060; Su et al., 1995, Anticancer Res. 15:1841-1848; Martinet al., 1995, J. Exp. Med.182:1545-1556).

Western blotting. Cell extracts in RIPA buffer were prepared and equal concentrations of proteins were evaluated for MDA-7, BCL-2, BAXand EF-1α protein levels by Western blotting as described in Kita et al., 1999, Intl. J. Cancer 80:553-558; Lebedeva et al., 2000, Cancer Res. 60:6052-6060 and Su et al., 1995, Intl. J. Oncol. 7:1279-1284.

6.2. Results and Discussion

The combination of Ad.mda-7 and AS K-ras PS ODN synergistically suppressed growth in mut K-ras expressing human pancreatic carcinoma cells. Mda-7 is a broad-spectrum cancer-specific growth -suppressing gene, which displays no apparent harmful effects in normal cells (Jiang et al., 1995, Oncogene 11:2477-2486; Jiang et al., 1996, Proc. Natl. Acad. Sci. U.S.A. 93:9160-9165; Madireddi et al., 2000, Adv. Exptl. Med. Biol. 465:239-261; Su et al., 1998, Proc. Natl. Acad. Sci. U.S.A. 95:14400-14405; Saeki et al., 2000, Gene Ther. 7:2051-2057; Mhashilkar et al., 2001, Mol. Med. 7:271-282). Infection of a diverse group of human cancers with Ad.mda-7, including melanoma, glioblastoma multiforme and osteosarcoma, and carcinomas of the breast, cervix, colon, endometrium, ltmg and prostate, results in growth suppression and hypodiploidy, a cellular change frequently associated with apoptosis (Jiang et al., 1996, Proc. Natl. Acad. Sci. U.S.A. 93:9160-9165; Madireddi et al., 2000, Adv. Exptl. Med. Biol. 465:239-261; Su et al., 1998, Proc. Natl. Acad. Sci. U.S.A. 95:14400-14405; Saeki et al., 2000, Gene Ther. 7:2051-2057; Mhashilkar et al., 2001, Mol. Med. 7:271-282). In a detailed study with several breast carcinoma cell lines, the ability of Ad-mda-7 to induce growth suppression was found to be independent ofp53-status and to correlate with induction of apoptosis, as monitored by DNA nucleosomal laddering, the TUNEL reaction and Annexin V staining (Madireddi et al., 2000, Adv. Exptl. Med. Biol. 465:239-261; Su et al., 1998, Proc. Natl. Acad. Sci. U.S.A. 95:14400-14405; Mhashilkar et al., 2001, Mol. Med. 7:271-282). In contrast, growth was minimally affected and no induction of apoptosis was apparent in early passage normal mammary epithelial cells or the normal breast epithelial cell line, HBL-100, after infection with Ad.mda-7.

When evaluating the effect of mda-7 on diverse cancer subtypes it was readily apparent that pancreatic carcinoma cells are inherently resistant to ectopic expression of mda-7. Infection of mutated or wild type K-ras expressing pancreatic carcinoma cells with 100 pfu/cell of Ad. mda-7 or Ad.vec (the Ad construct lacking the mda-7 gene insert) did not significantly affect growth and no selective induction of apoptosis was evident (see FIG. 5). A dose-dependent growth inhibitory effect was apparent when the different pancreatic carcinoma cells were treated with 0.1 to 5 micromolar antisense K-ras phosphorothioate oligonucleotide (AS K-ras PS ODN), with a maximum inhibition of ~10 to ~30 percent depending on the cell type when treated for 3 or 4 days with 5 micromolar AS K-ras PS ODN (FIG. 5). Growth of BxPC-3, which carries a wild type K-ras gene, was inhibited the least by the K-ras PS ODN. Selectivity of the AS K-ras PS ODN was suggested by the fact that treatment with either scrambled ("SC") or mismatched ("MM") PS ODN resulted in significantly less growth suppression than treatment with the AS K-ras PS ODN (see FIG. 5). These studies document that a single application of Ad.mda-7 or AS K-ras PS ODN to mutated or wild type K-ras pancreatic carcinoma cell lines can induce variable degrees of growth suppression. However, in all cases growth suppression was transient and cells survived the single treatment and continued to proliferated, even when initially exposed to 5 micromolar PS ODN.

When mutated K-ras pancreatic carcinoma cells were infected with Ad.mda-7 and then treated with 0.1 to 5.0 micromolar AS K-ras PS ODN, but not SC or MM PS ODN, a profound synergistic growth inhibitory effect and a decrease in cell survival were evident (FIGS. 5 and 6M-O). In contrast, no synergistic growth inhibition or decrease in cell viability was detected in wt K-ras BxPC-3 cells (FIGS. 5 and 6P). Additionally, no effect on growth or viability was apparent with any of the treatments in early passage normal human prostate epithelial cells or when pancreatic cancer cells were infected with an adenovirus expressing luciferase or β-galactosidase and then treated with AS K-ras ODN. These results document an anti-survival effect of the combination of mda-7 and AS K-ras PS ODN in mutated K-ras pancreatic carcinoma cells, but not in wild type K-ras pancreatic cancer cells or normal epithelial cells.

A previous study reported that AS K-ras PS ODN that target specific point mutations in K-ras codon 12 can reduce growth in mutant pancreatic carcinoma cell lines, but not in wild type K-ras BxPC-3 cells (Kita et al., 1999, Intl. J. Cancer 80:553-558). This effect was greater using appropriate mutation-mismatched AS PS ODN versus mutation-mismatched PS ODN. Effects on growth, although less, were also apparent when using AS PS ODN that did not correspond precisely to the mutation in K-ras codon 12 of the particular pancreatic carcinoma analyzed. This observation supports numerous previous studies indicating that AS PS ODN can induce both specific and apparently non-specific effects in target cells (Stein and Cheng, 1993, Science 261:1004-1012; Stein, 1996, Trends Biotechnol. 14:147-149; Pawlak et al., 2000, Cancer Treat. Rev. 26:333-35030-32).

In the present study, AS K-ras PS ODN were designed to interact with the AUG start codon of the K-ras gene. Treatment of both mutated and wild-type K-ras expressing pancreatic carcinoma cells with AS K-ras PS ODN, but not MM or SC PS ODN, reduced K-ras p21 protein levels in both mutated and wild-type K-ras cells by greater than 80 percent within 24 hours (FIG. 7). This effect was observed with and without Ad.vec or Ad.mda-7 infection, which did not consistently cause a further alteration in K-ras levels (FIG. 7). Moreover, the growth inhibitory effect of the AS K-ras PS ODN was greater in the three mutated K-ras pancreatic carcinoma cells than in the wild type K-ras BxPC-3 cell line (FIG. 5). As observed in the study of Kita et al. (1999, Intl. Journal of Cancer 80:553-558), growth inhibition induced by AS K-ras PS ODN, either point or start codon specific (as in this example), exceeded that observed using SC or MM PS ODN. In addition, no synergistic growtl inhibitory effects or decreases in cell survival were apparent in Ad. mda-7 infected pancreatic carcinoma cells that were subsequently treated with SC or MM PS ODN. These results confirm a profound synergistic growth inhibitory effect specifically in mutated K-ras pancreatic carcinoma cells after infection with Ad.mda-7 and treatment with AS K-ras PS ODN.

Plasma membrane associated small molecular weight GTP-binding proteins are frequently utilized by cells in the process of signal transduction from the inner leaflet of the plasma membrane to the cytosol. The prototypical small molecular weight family of GTP-binding proteins is the ras gene family (Kolch, 2000, Biochem. J. 351:289-305). Based on the observation that K-ras mutations appear in atypical hyperplastic ducts that surround the ductal-like cancer cells (Lemoine et al., 1992, Gastroenterol. 102:230-236), it is currently believed that K-ras mutations represent a very early event in pancreatic carcinogenesis. The resulting K-ras mutation induces a conformational change in the molecule and a concomitant maintenance of RAS activation by decreasing hydrolysis of GTP to GDP (Kolch, 2000, Biochem. J. 351:289-305; Reuther and Der, 2000, Curr. Opin. Cell Biol. 12:157-165). When activated, K-RAS can signal into the cytosol via multiple downstream signaling pathways such as the classical MAPK pathway; the PI3 kinase pathway; and the JNK pathway, to induce a plethora of cellular changes, including enhanced proliferation (Dent et al., 1992, Science 257:1404-1407; Gire et al., 2000, Oncogene 19:2269-2276; Almeida et al., 2000, J. Cell Biol. 149:741-754). In these contexts, blocking K-RAS expression may alter downstream pathway activities in mutated K-ras pancreatic cancer cells, rendering these cells sensitive to MDA-7 induction of growth suppression and effects on cell viability.

Infection of mutated K-ras pancreatic carcinoma cells with Ad.mda-7 followed by transfection with as AS K-ras expression vector inhibited growth in vitro and tumorigenesis in vivo in nude mice. As an additional approach to inhibiting K-ras expression, a K-ras gene fragment of 346 nucleotides (extending from nucleotide 172 to nucleotide 517), that was previously shown to inhibit pancreatic cancer cell growth in vitro and in vivo when used in an antisense orientation (Aoki et al., 1995, Cancer Res. 55:3810-3816; Aoki et al., 1997, Mol. Carcinogen. 20:251-258), was isolated by PCR from BxPC-3 cells and cloned into a pcDNA3.1 (neomycin resistance) expression vector. This expression vector was then tested for effects on pancreatic carcinoma cells, when used alone or in combination with Ad.mda-7. As can be seen in FIG. 8 (upper row of culture plates), infection of MIA PaCA-2 cells with Ad.vec alone or in combination with AS K-ras PS ODN did not significantly alter colony formation. Similarly, infection of MIA PaCa-2 cells with Ad.mda-7 also did not modify cloning efficiency in monolayer culture. In contrast, the combination of Ad.mda-7 with AS K-ras PS ODN dramatically inhibited colony formation (confinning previous studies using cell counting by hemocytometer and MTT staining). To test the effect of the AS K-ras plasmid in combination with Ad.mda-7 on pancreatic carcinoma cell growth, MIA PaCa-2 cells were infected with Ad.vec or Ad.mda-7 and transfected with a control or the AS K-ras plasmid and G418-resistant colony formation was determined. As can be seen in FIG. 8 (lower row of culture plates), a dramatic suppression in growth was observed only in MIA PaCa-2 cells infected with Ad.mda-7 and transfected with the As K-ras plasmid. Quantitatively similar growth inhibitory results were obtained when the same protocols were used with AsPC-1 or PANC-1 mutated K-ras pancreatic carcinoma cells, but not with wild type K-ras BxPC-3 cells. These results indicate that both AS PS ODN and antisense K-ras expression by plasmid transfer can synergize with mda-7 to inhibit mutated K-ras pancreatic carcinoma cell growth.

MIA PaCa-2 cells form tumors in athymic nude mice with a short latency time. Transfection with an AS K-ras plasmid or infection with Ad.mda-7 resulted in rapidly growing tumors in 80 percent of animals (3 independent experiments, n=26). Similarly, infection with Ad.vec, a plasmid lacking the gene inserts, or transfection with a plasmid construct containing a 346 nt K-ras gene fragment cloned in a sense orientation did not significantly inhibit tumor formation (76 percent tumors; n=17; 3 independent experiments).

In contrast, a remarkable complete suppression in tumor formation was apparent only when MIA PaCa-2 cells were infected with Ad.mda-7 and then transfected with the AS K-ras plasmid prior to being injected into athymic nude mice (no tumors formed in 13 animals; 3 independent studies). These findings document that in mutated K-ras pancreatic cancer cells, infection with Ad. mda-7 combined with targeting the K-ras gene for inhibition in a small subset of cells by means of transfection with an AS K-ras expression plasmid eliminated in vivo tumor formation in nude mice. Since transfection is an inherently inefficient means of introducing genes into target cells, it is possible that cells receiving the combination treatment release factor(s) that sensitize adjacent tumor cells containing mda-7 to lose viability, thereby preventing tumor formation.

The combination of Ad.mda-7 and AS K-ras PS ODN induced apoptosis selectively in mutated K-ras expressing human pancreatic carcinoma cells. The mechanism by which MDA-7 selectively decreases colony formation and growth in human cancer cells involves induction of apoptosis (Madireddi et al., 2000, Adv. Exptl. Med. Biol. 465: 239-261; Su et al., 1998, Proc. Natl. Acad. Sci. U.S.A. 95:14400-14405; Saeki et al., 2000, Gene Ther. 7:2051-2057; Mhashilkar et al., 2001, Mol. Med. 7:271-282). To determine if the combination treatment of K-ras mutated pancreatic cancer cells decreases cell survival by induction of apoptosis, a number of assays typically used to monitor programmed cell death were performed. In many cell types, induction of apoptosis is associated with DNA degradation, which can be monitored by generation of nucleosomal DNA ladders (Su et al., 1998, Proc. Natl. Acad. Sci. U.S.A. 95:14400-14405; Reed, 2000, Am. J. Pathol. 157:1415-

1430; Green and Reed, 1998, Science 281:1309-1312). As can be seen in FIG. 9, treatment of mutated K-ras- expressing pancreatic carcinoma cells, but not wild-type K-ras expressing BxPC-3, with Ad.mda-7 plus As K-ras PS ODN resulted in DNA fragmentation. The specificity of this effect was further documented by the lack of nucleosomal DNA ladders in pancreatic cancer cells infected with Ad.mda-7 or treated with 5.0 µM AS K-ras PS ODN alone or in cells treated with the combination of Ad. mda-7 with 5.0 µM MM K-ras PS ODN. Confirmation of induction of apoptosis by combination treatment in the three mutated K-ras pancreatic carcinoma cells was verified by DAPI and by propidium iodide staining, increases in the number of hypodiploid cells and Annexin V staining by FACS analysis. These results confirm that the combination of Ad.mda-7 and AS K-ras PS ODN decreased viability in mutated K-ras expressing pancreatic carcinoma cells by inducing apoptosis.

MDA-7 protein was present in mutated K-ras expressing human pancreatic carcinoma cells following infection with Ad.mda-7 and treatment with AS K-ras PS ODN. The reason that pancreatic carcinoma cells are resistant to mda-7 and the mechanism by which the combination of Ad.mda-7 and AS K-ras PS ODN sensitizes specific pancreatic carcinoma cells to mda-7 induction of growth suppression and apoptosis is not known. One hypothesis is that the mutated K-ras protein, or biochemical pathways modified by this protein, prevents synthesis, processing and/or secretion of MDA-7 protein following infection with Ad.mda-7. This possibility was tested by determining the effect of various treatment protocols on intracellular MDA-7 protein levels in the different pancreatic carcinoma cell lines (FIGS. 10A-D). No MDA-7 protein was detected in cell lysates from the four different pancreatic carcinomas 24 hours after infection with Ad.mda-7 alone or in combination with MM or SC PS ODN. This occurred despite the production of mda-7 mRNA in all four pancreatic cancer cell lines following infection with Ad.mda-7 (FIG. 11). In contrast, MDA-7 protein was readily detected in the three K-ras mutated pancreatic carcinoma cell lines after infection with Ad. mda-7 and treatment with AS K-ras PS ODN (FIGS. 10A-C). In the case of wild-type K-ras expressing BxPC-3, MDA-7 protein was not detected (FIG. 10D). These results suggest that mutated K-ras may negatively affect MDA-7 protein processing in mutated K-ras-pancreatic cancer cells. The absence of MDA-7 protein, using similar protocols, in BxPC-3 cells suggests that other pathways may be operational that modify expression and/or retention of MDA-7 protein in these pancreatic carcinoma cells. Since apoptosis only occurs in K-ras mutated pancreatic cancer cells treated with the combination of mda-7 and antisense ras, these studies support a potential correlation between presence/retention of MDA-7 protein and induction of growth suppression and programmed cell death in pancreatic carcinoma cells.

The combination of Ad.mda-7 and AS K-ras PS ODN alters the levels of apoptosis-associated Proteins. Previous studies indicate that infection of diverse cancer cells with Ad.mda-7 results in apoptosis, and in the majority of cases this process is associated with up-regulation of BAX protein and changes in the ratio of BAX to BCL-2 protein (Madireddi et al., 2000, Adv. Exptl. Med. Biol. 465:239-261; Su et al., 1998, Proc. Natl. Acad. Sci. U.S.A. 95:14400-14405; Saeki et al., 2000, Gene Ther. 7:2051-2057; Mhashilkar et al., 2001, Mol. Med. 7:271-28218-21). However, the ability of Ad.mda-7 to induce apoptosis in specific cancer cells, such as DU-145 human prostate carcinoma cells which do not produce BAX protein (Rampino et al., 1997, Science 275:967-969), indicates that mda-7 can also mediate programmed cell death in certain cancer cells by a BAX-independent pathway. Based on these considerations and the presence of MDA-7 protein specifically in combination treated mutated K-ras pancreatic carcinoma cells, experiments were performed to determine the levels of BAX and BCL-2 proteins in treated cells. When analyzed 3 days after combination treatment, in which the majority of K-ras mutated cells were apoptotic, the levels of BAX protein were elevated in PACN-1, MIA PaCa-2 and AsPC-1 cells, ~7.5-, ~3- and ~10-fold, respectively, but not in BxPC-3 cells (FIG. 12). Moreover, the levels of BCL-2 protein were significantly reduced in PANC-1(~8-fold) and MIA PaCa-2 (~13.5-fold) cells, marginally reduced in AsPC-1 cells (~1.2-fold) and remained unchanged in BxPC-3 cells (FIG. 12). These results are consistent with involvement of BAX protein and changes in the ratio of BAX to BCL-2 proteins in inducing apoptosis in combination treated pancreatic carcinoma cells.

7. EXAMPLE

Antisense RAS Nucleic Acids Having 346 or 631 Nucleotides, in Combination with mda-7, Inhibit Colony Formation of Pancreatic Cancer Cells

7.1. Materials and Methods

MIA PaCa-2 cells were infected with 100 pfu/cell of Ad.mda-7, and then were transfected with 10 micrograms of a wild-type K-ras gene fragment of 346 nucleotides (nucleotides 172 to 517 of the K-ras cDNA) or 631 nucleotides (nucleotides 172 to 802 of the K-ras cDNA), cloned in the antisense orientation in the pcDNA3.1 expression vector, in the presence of 10 micromolar lipofectamine. As controls, some cells were infected with 100 pfu/cell of AD.mda-7 and then transfected with 10 micrograms of empty pcDNA3.1 vector, and other cells were not adenovirus-infected, but were only transfected with the empty pcDNA3.1 vector. Twelve hours after transfection the cells were seeded at various cell densities and selected in G418-containing medium and colony formation was assessed after 2-3 weeks. Analogous experiments were performed using PANC-1 and AsPC-1 cells.

7.2. Results

The results of the foregoing experiments using MIA PaCa-2 cells are shown in bar graph format in FIG. 13. Colony formation was inhibited slightly, if at all, by mda-7 alone or either transfection of 346 or 631 nucleotide ras antisense sequences without Ad.mda-7 infection. However, infection with Ad.mda.7 combined with transfection with either the 346 or 631 nucleotide antisense ras-encoding plasmid resulted in substantial inhibition of colony formation, indicating that ras antisense nucleotides of diverse sizes can exert effective inhibition of RAS activity. Qualitatively similar results were observed in PANC-1 and ASPC-1 cells.

8. EXAMPLE

Secretion of Biologically Functional MDA-7 Following Infection of Primary Rat Hepatocytes with AD.mda-7

8.1. Overview

Systemic infection with adenovirus vectors invariably results in high levels of infection in the liver (Huard et al., 1995, Gene Ther. 2(2):107-115; Morral et al., 1999, Proc. Natl. Acad. Sci. U.S.A. 96:12816-12821). In specific instances this interaction can result in toxicity (Somia and Verma, 2000, Nat. Rev. Genet. 1(2):91-99). Previous studies have documented that mda-7 is not toxic to a spectrum of normal human cell types, including skin and lung fibroblasts, breast and prostate epithelial cells, endothelial cells, and melanocytes (Madireddi et al., 2000, Adv. Exp. Med. Biol. 465:239-261; Saeki et al., 2000, Gene Ther. 7:2051-2057; Mhashilkar et al., 2001, Mol. Med. 7:271-282). In contrast, mda-7 selectively induces growth suppression and programmed cell death (apoptosis) in a diverse spectrum of human tumor cells, including melanoma, glioblastoma multiforme, osteosarcoma and carcinomas of the breast, cervix, colon, lung, nasopharynx, ovary and prostate (Madireddi et al., 2000, Adv. Exp. Med. Biol. 465:239-261; Saeki et al., 2000, Gene Ther. 7:2051-2057; Mhashillcar et al., 2001, Mol. Med. 7:271-282). Pancreatic carcinoma cells, however, are refractive to Ad.mda-7, unless infection is combined with approaches that decrease RAS activity. The experiments described in this section were performed to (1) determine if infection of primary hepatocytes with Ad.mda-7 induces toxicity; and (2) determine if infection of primary hepatocytes with AD.mda-7 results in the production of biologically active MDA-7 protein inside cells and in medium used to grow the infected hepatocytes.

8.2. Materials and Methods

Preparation of primary rat hepatocytes and preparation of conditioned medium and cell lysates. Primary rat hepatocytes were isolated using the two stage collagenase perfusion technique as described in Park et al., 2000, Mol. Biol. Cell. 11:2915-2932. Four hours after attachment, cells were infected at a multiplicity of infection of 30 with either a null adenovirus vector (Ad.vec) or Ad.mda-7 (Su et al., 1998, Proc. Natl. Acad. Sci. U.S.A. 95:14400-14405). Cells were gently rocked during this process to promote viral adsorption and infection. Eighty-four hours after infection, the media was removed from the cells and used for further experimentation, as described below. Infected hepatocytes were scraped into the same volume of sterile Dulbecco's Modified Eagle's Medium ("DMEM") that was used during cell culture, lysed by a single freeze-thaw cycle at −20° C. with triturating on thawing through a P1000 pipette tip, and then the cellular debris was removed by centrifugation and media containing the cellular extract was decanted. The media was used for further experimentation, also as described below.

Assay of Ad.mda-7 and Ad.vec-infected hepatocyte conditioned medium and lysed cells for biological activity toward human pancreatic cancer cells. MIA PaCa-2 cells were seeded at 1×106/10 cm plate. The next day, cells were allocated into the following groups and treated as follows: (1) untreated control; (2) Ad.mda-7 infected (using 100 pfu/cell); (3) transfected with AS K-ras phosphorothioate oligonucleotides having SEQ ID NO:15 at a concentration of 0.5 micromolar in the presence of 10 microgram per milliliter of lipofectamine; or infected with Ad.mda-7 and transfected with AS K-ras phosphorothioate oligonucleotide, using the same conditions as for groups (2) and (3). The next day the cells from the various groups were resuspended using trypsin/versene and replated in duplicate at $1 \times 10^5/35$ nun plate. After cell attachment had occurred (about 6 hours), the growth medium was removed and replaced with either Ad.mda-7-infected hepatocyte lysate or culture supernatant (diluted 1:1 with DMEM+10% fetal bovine serum), prepared as described above, or, for controls, fresh growth medium. Cell numbers were determined every other day over an 8 day period.

8.3. Results

The results are depicted in FIGS. 14A-B, for control cells treated with either mda-7 infected hepatocyte lysate (FIG. 14A) or supernatant (FIG. 14B); FIGS. 15A-B for Ad.mda-7 infected MIA PaCa-2 cells treated with either mda-7 infected hepatocyte lysate (FIG. 15A) or supernatant (FIG. 15B); and FIGS. 16A-B for AS K-ras oligonucleotide transfected MIA PaCa-2 cells treated with either mda-7 infected hepatocyte lysate (FIG. 16A) or supernatant (FIG. 16B). FIGS. 15A-B and 16A-B also depict the cell numbers for MIA PaCa-2 cells which had been both infected with Ad.mda-7 and transfected with AS K-ras oligonucleotide.

Infection of primary rat hepatocytes with Ad.mda-7 (30 pfu/cell) did not induce a toxic effect in primary liver cells. The infected hepatocytes apparently secreted MDA-7 processed protein(s) which, when administered to either Ad.mda-7 infected (FIG. 15B) or AS K-ras oligonucleotide transfected (FIG. 16B) MIA PaCa-2 pancreatic carcinoma cells, suppressed cell growth. Moreover, when assayed 84 hours post-infection, biological activity (as evidenced by growth suppression) was also observed when Ad.mda-7, but not Ad.vec, infected hepatocyte lysates were added to sensitized pancreatic carcinoma cells (FIGS. 15A and 16A). These results indicate that infection with Ad.mda-7 resulted in the production of secreted MDA-7 protein, and that this protein can affect appropriately sensitized pancreatic cancer cells when administered via the surrounding medium.

The biological effect appeared to be greatest on MIA PaCa-2 cells treated with AS K-ras oligonucleotides (FIGS. 16A and B). A significant growth inhibition was also observed in Ad.mda-7 infected MIA PaCa-2 cells (FIGS. 15A and B), suggesting possible synergy between intracellular pathways and membrane-mediated signal transduction pathways. In contrast, no significant effect was apparent when untreated MIA PaCa-2 cells were exposed to either the infected hepatocyte lysate or culture supernatant (FIGS. 14A and B).

In additional experiments, it was also observed that Ad.mda-7 infected hepatocyte culture supernatant had a growth suppressive effect on cancer cells which are known to respond to increases in intracellular MDA-7 protein, in particular DU-145 human prostate cancer cells.

9. EXAMPLE

Co-infection of Viral Vectors Carrying mda-7 or AS K-ras Inhibits Growth of Pancreatic Cancer Cells

9.1 Materials and Methods

The following procedure was followed for four different pancreatic cancer cell lines, AsPC-1, BxPC-3, PANC-1, and MIA PaCa-2. Cells were seeded at $1 \times 10^6/10$ cm plate and the next day the cultures were either untreated (control) or infected with 100 pfu/cell of Ad.mda-7 or Ad.K-ras AS or 50 pfu/cell+50 pfu/cell with Ad.mda-7+Ad.K-rasAS (that is, infected with both viruses). After 2 hours of incubation with the various viruses, complete growth medium RPMI-1640 supplemented with 10 percent fetal bovine serum was added to the cells and they were incubated for an additional 6 to 8 hours at 37° C. in a 5 percent $CO_2$/95 percent air humidified incubator. The cells were then resuspended and plated at 1×10⁵/35 mm plate in triplicate and cells were incubated at 37° C. under the same conditions. Two, four, six and eight days later the cell numbers were determined using a hemocytometer. Replicate samples varied by less than or equal to 10 percent.

9.2. Results

Figure 17A:
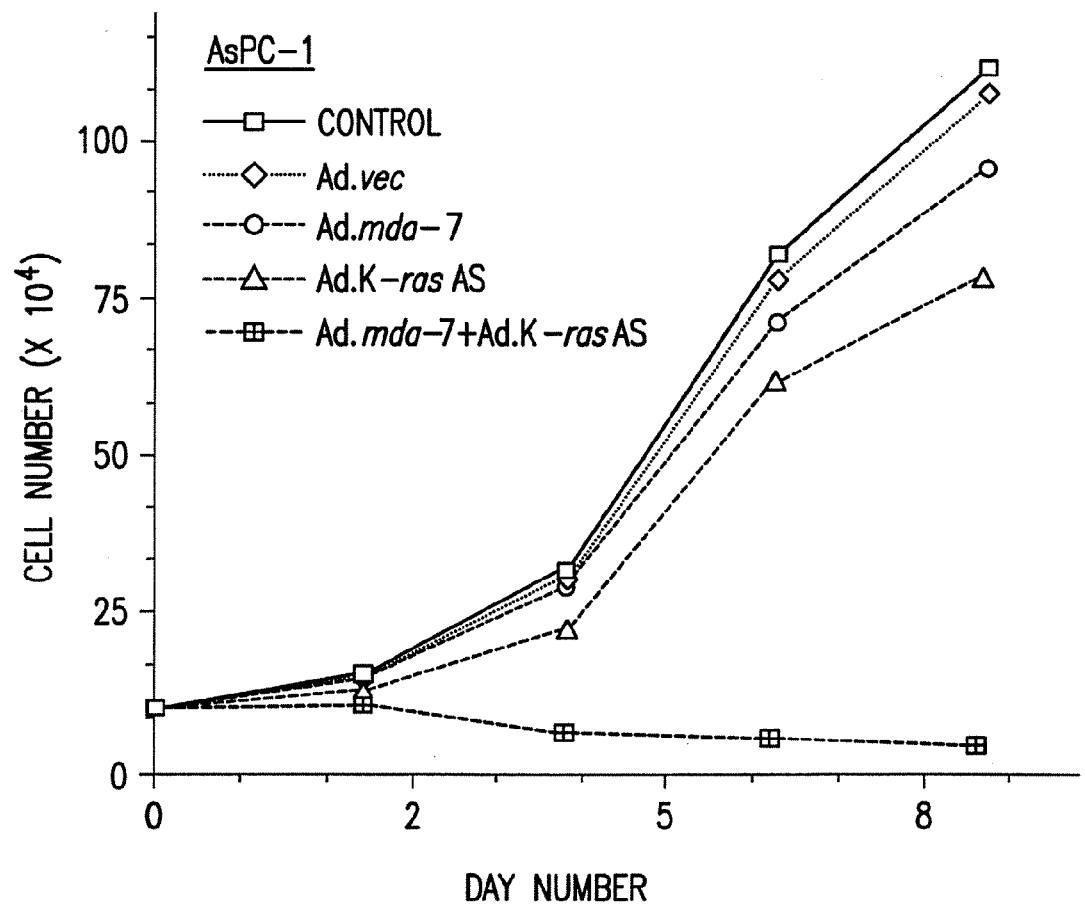
Figure 17B:
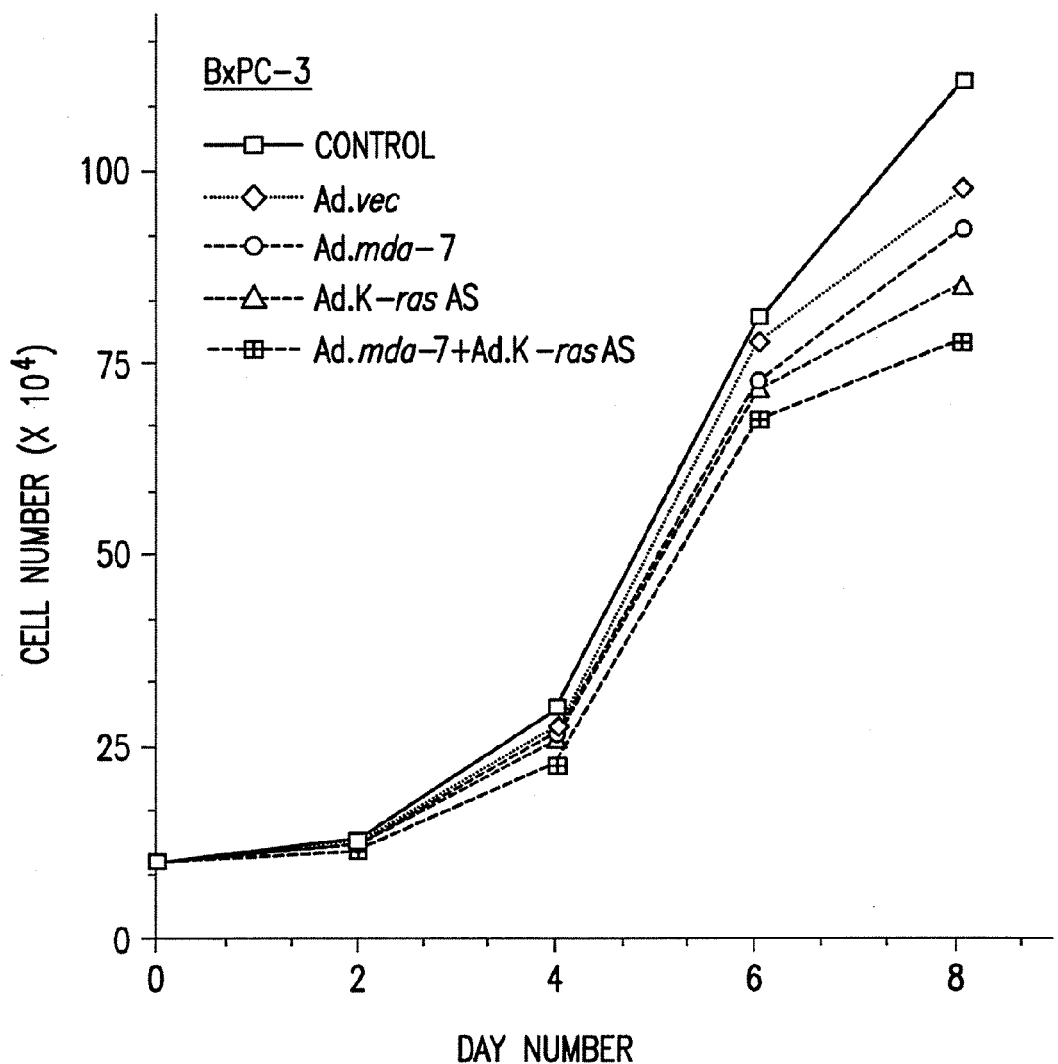
Figure 17C:
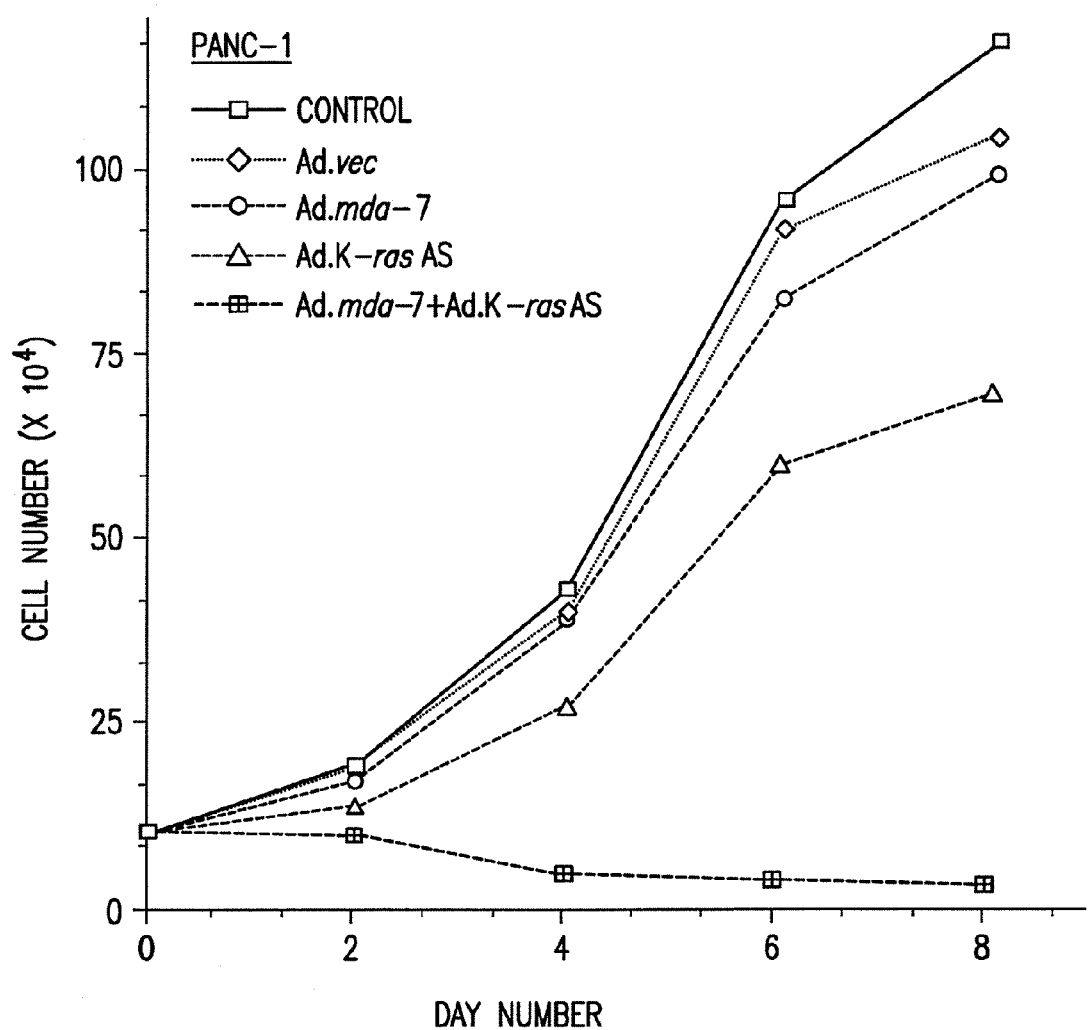
Figure 17D:
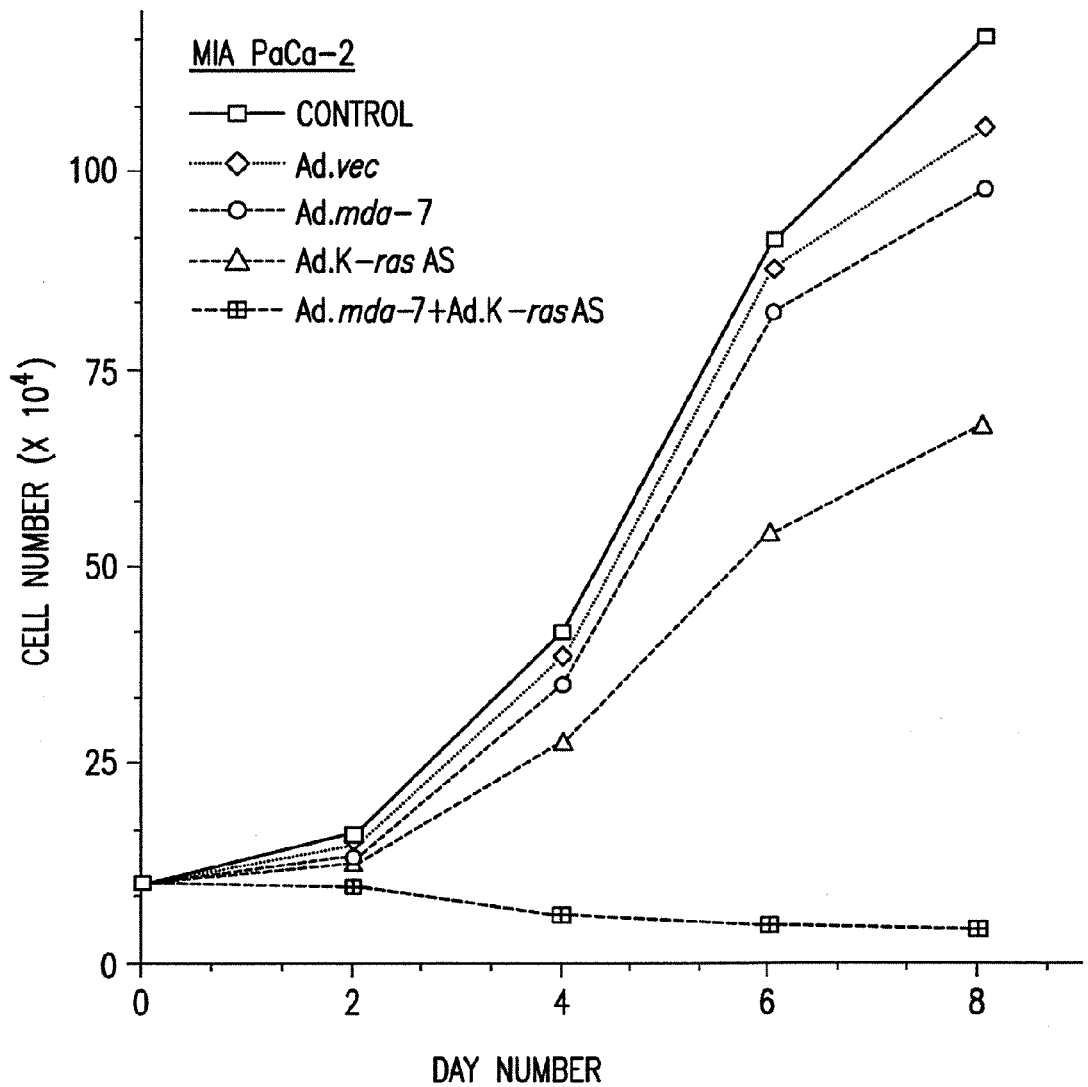

The results are presented in FIGS. 17A-D. Infection with Ad.mda-7 alone (represented as a dashed line joining open circles in FIGS. 17A-D) had little effect on any of the cell lines tested. Infection with Ad.K-ras AS (represented as a broken line joining open triangles in the figures), which contains the 631 bp fragment of K-ras in an antisense orientation, as described above, inhibited the growth of the four pancreatic carcinoma cell lines to variable degrees; Ad.K-ras AS infection inhibited growth of MIA PaCa-2 (FIG. 17D) and PANC-1 (FIG. 17C) equally, had a smaller inhibitory effect on AsPC-1 (FIG. 17A) and little effect on BxPC-3 (FIG. 17B). In contrast, co-infection of cultures with Ad.mda-7 and Ad.K-ras AS (represented as a dashed line joining squares with+overstrikes in the figures) had a synergistic inhibitory effect on the cell lines carrying an activating mutation in K-ras (AsPC-1, PANC-1 and MIA PaCa-2; FIGS. 17A,C and D), but no significant effect on BxPC-3, which has a wild-type K-ras gene (FIG. 17B). These studies demonstrate that the combination of Ad.mda-7+Ad.K-ras AS profoundly inhibited the growth of pancreatic carcinoma cells expressing a mutant K-ras gene without inducing this effect in wild-type K-ras carrying pancreatic carcinoma cells.

10. EXAMPLE

Comparison of Effects of Infection with Adenovirus Vectors Expressing mda-7 or AS K-ras Alone Versus a Bipartite Adenovirus Vector Co-expressing mda-7 and AS K-ras on the Growth of Pancreatic Cancer Cells

10.1 Materials and Methods

Cell culture and viability assays. The AsPC-1, MIA PaCa-2, PANC-1 and BxPC-3 human pancreatic carcinoma cell lines were cultured in RPMI medium containing 10% FBS at 37° C. in a 95% air, 5% $CO_2$ humidified incubator. Cell growth and viability was monitored by the 3-(4,5-dimethylthiazol-2-yl)-2,5-diphenyl tetrazolium bromide (MTT) staining technique as described in (Lebedeva et al., 2000, Cancer Res. 60:6052-6060).

Adenovirus infection protocol. Different replication incompetent adenoviruses were constructed which include Ad.mda-7 (FIG. 2), Ad.AS.K-ras (FIG. 3) and Ad.bpv (FIG. 4). An empty adenoviral vector (Ad.vec) was used as a control. For MTT assay, 1500 cells were plated in each well of a 96-well plate. The next day, infection with adenovirus was carried out at a multiplicity of infection (MOI) of 100 pfu/cell. The cells were incubated with virus in 30 µl of serum-free medium for 2 hr to allow the complete adsorption of the virus. After 2 hr the cells were cultured in complete growth medium. For other experiments, 1×10⁶ cells were plated in a 10-cm dish. Adenovirus infection was carried out the next day in 1.5 ml of serum-free medium for 2 hr and then the medium was replaced with complete growth medium. Cell viability was assessed by MTT assay at day 1, 3, 5 and 7 post-infection.

Total RNA extraction and Northern blot analysis. Cells were infected with the adenovirus vectors at a multiplicity of infection (MOI) of 100 pfu/cell. Expression of mda-7 was analyzed by Northern Blot analysis using a $^{32}$P-dCTP labeled mda-7 cDNA probe. At two days post-infection, total RNA was extracted by Qiagen RNeasy mini kit according to the manufacturer's protocol. 5 µg of total RNA was denatured at 70° C. for 10 min, electrophoresed in a 1% agarose gel containing formaldehyde and transferred to a nylon membrane. The membrane was hybridized with $^{32}$P-dCTP labeled mda-7 cDNA probe using ExpressHyb hybridization solution (Clontech, Palo Alto, Calif.) according to the manufacturer's protocol. Following hybridization the membrane was washed and exposed for autoradiography.

Preparation of whole cell lysate and Western blot analysis. Cells were either uninfected (control) or infected with either Ad.vec or Ad.bpv at a multiplicity of infection (MOI) of 100 pfu/cell. At three days post-infection, cells from a 10-cm dish were harvested in 900 µl RIPA buffer [1% Nonidet P-40, 0.5% sodium deoxycholate and 0.1% SDS in phosphate-buffered saline (PBS) with protease inhibitor cocktail (Roche Molecular Biochemicals, Indianapolis, Ind.)]. The DNA was sheared by passing through a 21-gauge needle and centrifuged at 12,000 rpm for 10 min at 4° C. The supernatant was used as total cell lysate. Thirty micrograms of total cell lysate from each sample were run in a 12.5% SDS-polyacrylamide gel. The proteins were transferred to a nitrocellulose membrane using an electroblotting apparatus. The membranes were blocked with Blotto A [10 mmol/L Tris-HCl (pH 8.0), 150 mmol/L NaCl, 5% skimmed milk and 0.05% Tween-20] for 1 h at room temperature and incubated with antibodies against MDA-7 (1:1000; rabbit polyclonal) and K-RAS (1:200; mouse monoclonal) at 4° C. overnight. The membranes were washed three times for 5 min each with TBS-T [10 mmol/L Tris-HCl (pH 8.0), 150 mmol/L NaCl and 0.05% Tween-20] and incubated with horseradish peroxidase conjugated goat anti-rabbit IgG or goat anti-mouse IgG (1:5000) in Blotto A for 1 h at room temperature. The membranes were washed in TBS-T 10 min each for 3 times. Chemiluminescence was detected by ECL western blotting detection kit (Amersham International plc, Buckinghamshire, UK) according to the manufacturer's protocol.

10.2. Results

Ad.bpv was constructed for the purpose of expressing mda-7 and AS.K-ras from a single adenoviral vector. To confirm that infection with Ad.bpv results in the production of mda-7 mRNA and protein, various pancreatic cancer cell lines were infected with either Ad.vec or Ad.bpv at a multiplicity of infection (MOI) of 100 pfu/cell. At 12, 24 and 48 hrs after infection, the cells were harvested and total RNA was extracted. The expression of mda-7 mRNA following Ad.bpv infection was analyzed by Northern blot analysis using $^{32}$P-dCTP labeled mda-7 cDNA probe. As shown in FIG. 18, mda-7 mRNA could not be detected in the cells infected with Ad.vec. However, a high level of mda-7 mRNA could be detected in the cells infected with Ad.bpv. This finding indicated that Ad.bpv infection leads to the production of mda-7 mRNA.

To confirm that the mda-7 mRNA that is transcribed following Ad.bpv infection can be efficiently translated into MDA-7 protein, Mia Paca-2 cells were infected with Ad.vec or Ad.bpv at a MOI of 100 pfu/cell. Cells were harvested after 3 days and total cell lysates were produced. The expression of MDA-7 and K-RAS proteins was detected by Western blot analysis using anti-MDA-7 and anti-K-RAS antibodies. As shown in FIG. 19, MDA-7 protein could not be detected in the control (uninfected) and Ad.vec infected cells. However, MDA-7 protein could be detected in Ad.bpv infected cells. The expression of K-RAS protein could be detected in the control and Ad.vec infected cells, but could not be detected in cells infected by Ad.bpv infected cells (data not shown). These results confirm the hypothesis that Ad.bpv infection would result in the efficient production of MDA-7 protein and downregulation of K-RAS protein.

The effect of Ad.bpv infection on the growth of pancreatic cancer cell lines was next tested. Mutant K-ras containing pancreatic cancer cell lines Panc-1, Mia Paca-2 and AsPc-3 and wild type K-ras containing cell line BxPc-3 were infected with Ad.vec, Ad.mda-7, Ad.AS.K-ras, combination of Ad.mda-7 and Ad.AS.K-ras and Ad.bpv. The infections were carried out at a MOI of 100 pfu/cell. The growth of the cells was monitored on day 1, 3, 5 and 7 post-infection by MTT assay. As shown in FIGS. 20A-D, control (uninfected), Ad.vec and Ad.mda-7 infected cells continued to grow at a similar rate in all cell lines. Infection with Ad.AS.K-ras alone resulted in about 20% reduction in cell number in Mut K-ras containing cell lines. The combination of Ad.mda-7 and Ad.AS.K-ras resulted in the complete inhibition of cell growth in Mut K-ras containing cell lines. Infection with Ad.bpv alone was as potent as the combination in inhibiting the growth of Mut K-ras containing cell lines. None of the infection protocols could inhibit the growth of the wild-type K-ras-containing BxPc-3 cells. These results indicate that Ad.bpv can be effectively used instead of the combination of Ad.mda-7 and Ad.AS.K-ras in inhibiting pancreatic cancer cell proliferation. The use of a single adenovirus vector in place of a combination of two adenovirus vectors is advantageous because it considerably reduces the potential toxicity associated with infection. Thus, Ad.bpv should be an efficacious tool for therapeutic purposes of pancreatic carcinoma.

Various publications and GenBank Database sequences are cited herein, the contents of which are incorporated by reference in their entireties.

I claim:

1. A viral vector comprising a nucleic acid encoding a MDA-7 protein having the sequence of SEQ ID NO:2 and a nucleic acid encoding an antisense ras nucleic acid, each operatively linked to a promoter element.

* * * * *